(12) United States Patent
Hlavinka

(10) Patent No.: US 8,895,679 B2
(45) Date of Patent: *Nov. 25, 2014

(54) CATALYST COMPOSITIONS AND METHODS OF MAKING AND USING SAME

(71) Applicant: Chevron Phillips Chemical Company LP, The Woodlands, TX (US)

(72) Inventor: Mark L. Hlavinka, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 77 days.

This patent is subject to a terminal disclaimer.

(21) Appl. No.: 13/660,857

(22) Filed: Oct. 25, 2012

(65) Prior Publication Data

US 2014/0121343 A1 May 1, 2014

(51) Int. Cl.
  *C08F 4/64* (2006.01)
  *C08F 4/52* (2006.01)
  *C08F 4/76* (2006.01)

(52) U.S. Cl.
  USPC ........... 526/161; 526/172; 526/160; 526/126; 526/127; 526/129; 526/130; 556/51; 502/103; 502/104; 502/118; 502/119; 502/120

(58) Field of Classification Search
  USPC .............. 556/51; 526/172, 161; 502/103, 104
  See application file for complete search history.

(56) References Cited

U.S. PATENT DOCUMENTS 3,161,629 A 12/1964 Gorsich
3,242,099 A 3/1966 Manyik et al.

(Continued)

FOREIGN PATENT DOCUMENTS

CN 103012196 4/2013
CN 103012196 A 4/2013

(Continued)

OTHER PUBLICATIONS

Maurya et al. Dalton Trans., 2006, 3561-3575.*

(Continued)

*Primary Examiner* — Rip A Lee
(74) *Attorney, Agent, or Firm* — Conley Rose, P.C.; Rodney B. Carroll; Cheryl L. Huseman

(57) ABSTRACT

An imine phenol compound having Structure I:

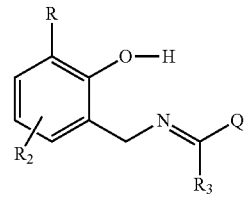

Structure I wherein O and N represent oxygen and nitrogen respectively; R comprises a halogen, a hydrocarbyl group, or a substituted hydrocarbyl group; $R^2$ and $R^3$ can each independently be hydrogen, a halogen, a hydrocarbyl group, or a substituted hydrocarbyl group; and Q is a donor group. A method comprising contacting a catalyst composition with a monomer under conditions suitable for the formation of a polymer wherein the catalyst composition comprises a metal salt complex of an imine (bis)phenolate compound, a solid oxide, and an optional metal alkyl and wherein the metal salt complex of an imine (bis)phenolate compound has Structure XIV

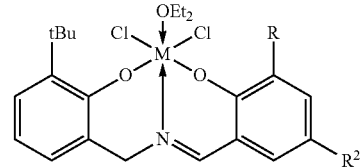

Structure XIV where M is titanium, zirconium, or hafnium; $OE_{t2}$ is ethoxide, R comprises a halogen, a hydrocarbyl group, or a substituted hydrocarbyl group; and $R^2$ comprises hydrogen, a halogen, a hydrocarbyl group, or a substituted hydrocarbyl group.

23 Claims, 7 Drawing Sheets

(('Bu)LZrCl₂(Et₂O))

(56) References Cited

U.S. PATENT DOCUMENTS

| | | |
|---|---|---|
| 3,248,179 A | 4/1966 | Norwood |
| 3,533,738 A | 10/1970 | Rundell et al. |
| 3,946,020 A | 3/1976 | Minato et al. |
| 4,060,480 A | 11/1977 | Reed et al. |
| 4,070,272 A | 1/1978 | Rausch |
| 4,077,904 A | 3/1978 | Noshay et al. |
| 4,101,445 A | 7/1978 | Levine et al. |
| 4,279,780 A | 7/1981 | Dombro |
| 4,452,910 A | 6/1984 | Hopkins et al. |
| 4,476,243 A | 10/1984 | Dombro |
| 4,501,885 A | 2/1985 | Sherk et al. |
| 4,526,942 A | 7/1985 | Chester et al. |
| 4,547,551 A | 10/1985 | Bailey et al. |
| 4,588,790 A | 5/1986 | Jenkins, III et al. |
| 4,596,862 A | 6/1986 | McDaniel et al. |
| 4,657,998 A | 4/1987 | Malpass |
| 4,659,685 A | 4/1987 | Coleman, III et al. |
| 4,788,171 A | 11/1988 | Klendworth |
| 4,794,096 A | 12/1988 | Ewen |
| 4,803,253 A | 2/1989 | McDaniel et al. |
| 4,806,513 A | 2/1989 | McDaniel et al. |
| 4,808,561 A | 2/1989 | Welborne, Jr. |
| 4,892,851 A | 1/1990 | Ewen et al. |
| 4,939,217 A | 7/1990 | Stricklen |
| 4,969,522 A | 11/1990 | Whitehurst et al. |
| 5,001,204 A | 3/1991 | Klendworth et al. |
| 5,010,152 A | 4/1991 | McDaniel et al. |
| 5,036,034 A | 7/1991 | Ewen |
| 5,037,911 A | 8/1991 | McDaniel et al. |
| 5,049,535 A | 9/1991 | Resconi et al. |
| 5,071,808 A | 12/1991 | Antberg et al. |
| 5,075,467 A | 12/1991 | Desobry |
| 5,085,705 A | 2/1992 | Withiam |
| 5,162,278 A | 11/1992 | Razavi |
| 5,171,798 A | 12/1992 | McDaniel et al. |
| 5,183,868 A | 2/1993 | Nordquest |
| 5,191,132 A | 3/1993 | Patsidis et al. |
| 5,210,352 A | 5/1993 | Alt et al. |
| 5,223,467 A | 6/1993 | Razavi |
| 5,321,105 A | 6/1994 | Rekers et al. |
| 5,332,707 A | 7/1994 | Karayannis et al. |
| 5,347,026 A | 9/1994 | Patsidis et al. |
| 5,352,749 A | 10/1994 | DeChellis et al. |
| 5,369,196 A | 11/1994 | Matsumoto et al. |
| 5,376,611 A | 12/1994 | Shveima |
| 5,399,636 A | 3/1995 | Alt et al. |
| 5,401,817 A | 3/1995 | Palackal et al. |
| 5,401,820 A | 3/1995 | McDaniel et al. |
| 5,416,228 A | 5/1995 | Ewen et al. |
| 5,420,320 A | 5/1995 | Zenk et al. |
| 5,434,116 A | 7/1995 | Sone et al. |
| 5,436,304 A | 7/1995 | Griffin et al. |
| 5,436,305 A | 7/1995 | Alt et al. |
| 5,439,995 A | 8/1995 | Bailly et al. |
| 5,444,134 A | 8/1995 | Matsumoto |
| 5,451,649 A | 9/1995 | Zenk et al. |
| 5,455,314 A | 10/1995 | Burns et al. |
| 5,461,127 A | 10/1995 | Naganuma et al. |
| 5,468,702 A | 11/1995 | Jejelowo |
| 5,483,014 A | 1/1996 | Turner et al. |
| 5,496,781 A | 3/1996 | Geerts et al. |
| 5,496,782 A | 3/1996 | Zandona |
| 5,498,581 A | 3/1996 | Welch et al. |
| 5,527,867 A | 6/1996 | Bergmeister |
| 5,534,473 A | 7/1996 | Welch et al. |
| 5,541,272 A | 7/1996 | Schmid et al. |
| 5,543,376 A | 8/1996 | Bergmeister |
| 5,554,795 A | 9/1996 | Frey et al. |
| 5,556,893 A | 9/1996 | Costa et al. |
| 5,563,284 A | 10/1996 | Frey et al. |
| 5,565,175 A | 10/1996 | Hottovy et al. |
| 5,565,592 A | 10/1996 | Patsidis et al. |
| 5,571,880 A | 11/1996 | Alt et al. |
| 5,575,979 A | 11/1996 | Hanson |
| 5,576,259 A | 11/1996 | Hasegawa et al. |
| 5,587,501 A | 12/1996 | Winter et al. |
| 5,594,078 A | 1/1997 | Welch et al. |
| 5,594,080 A | 1/1997 | Waymouth et al. |
| 5,612,271 A | 3/1997 | Zandona |
| 5,631,203 A | 5/1997 | Welch et al. |
| 5,631,335 A | 5/1997 | Alt et al. |
| 5,643,847 A | 7/1997 | Walzer, Jr. |
| 5,646,322 A | 7/1997 | van Beek et al. |
| 5,648,439 A | 7/1997 | Bergmeister et al. |
| 5,654,454 A | 8/1997 | Peifer et al. |
| 5,668,230 A | 9/1997 | Schertl et al. |
| 5,670,580 A | 9/1997 | Tazaki et al. |
| 5,700,748 A | 12/1997 | Murray |
| 5,703,181 A | 12/1997 | Tashiro et al. |
| 5,705,578 A | 1/1998 | Peifer et al. |
| 5,705,579 A | 1/1998 | Hawley et al. |
| 5,714,425 A | 2/1998 | Chabrand et al. |
| 5,714,555 A | 2/1998 | Chabrand et al. |
| 5,719,241 A | 2/1998 | Razavi et al. |
| 5,726,264 A | 3/1998 | Jung et al. |
| 5,739,220 A | 4/1998 | Shamshoum et al. |
| 5,780,659 A | 7/1998 | Schmid et al. |
| 5,807,938 A | 9/1998 | Kaneko et al. |
| 5,854,165 A | 12/1998 | Yabunouchi et al. |
| 5,854,363 A | 12/1998 | Jung et al. |
| 5,861,352 A | 1/1999 | Gila et al. |
| 5,866,497 A | 2/1999 | Murray |
| 5,883,036 A | 3/1999 | Fujie et al. |
| 5,886,202 A | 3/1999 | Jung et al. |
| 5,906,955 A | 5/1999 | Hamura et al. |
| 5,907,021 A | 5/1999 | Turner et al. |
| 5,919,983 A | 7/1999 | Rosen et al. |
| 5,942,459 A | 8/1999 | Sugano et al. |
| 6,034,187 A | 3/2000 | Maehama et al. |
| 6,096,677 A | 8/2000 | Wilson, Jr. |
| 6,107,230 A | 8/2000 | McDaniel et al. |
| 6,114,477 A | 9/2000 | Merrill et al. |
| 6,150,544 A | 11/2000 | Seki et al. |
| 6,165,929 A | 12/2000 | McDaniel et al. |
| 6,169,151 B1 | 1/2001 | Waymouth et al. |
| 6,174,981 B1 | 1/2001 | Bergmeister et al. |
| 6,180,736 B1 | 1/2001 | Muhle et al. |
| 6,187,880 B1 | 2/2001 | Welch et al. |
| 6,201,077 B1 | 3/2001 | Begmeister et al. |
| 6,204,346 B1 | 3/2001 | Bergmeister et al. |
| 6,225,425 B1 | 5/2001 | Dolle et al. |
| 6,239,059 B1 | 5/2001 | Saudemont et al. |
| 6,239,235 B1 | 5/2001 | Hottovy et al. |
| 6,262,191 B1 | 7/2001 | Hottovy et al. |
| 6,262,201 B1 | 7/2001 | Welch et al. |
| 6,268,447 B1 | 7/2001 | Murray et al. |
| 6,274,684 B1 | 8/2001 | Loveday et al. |
| 6,291,699 B1 | 9/2001 | Birmingham et al. |
| 6,294,494 B1 | 9/2001 | McDaniel et al. |
| 6,300,271 B1 | 10/2001 | McDaniel et al. |
| 6,300,451 B1 | 10/2001 | Mehta et al. |
| 6,316,553 B1 | 11/2001 | McDaniel et al. |
| 6,333,389 B2 * | 12/2001 | Whiteker et al. ............. 526/161 |
| 6,340,651 B1 | 1/2002 | Licht et al. |
| 6,340,652 B1 | 1/2002 | Sugano et al. |
| 6,355,594 B1 | 3/2002 | McDaniel et al. |
| 6,376,415 B1 | 4/2002 | McDaniel et al. |
| 6,388,017 B1 | 5/2002 | McDaniel et al. |
| 6,391,816 B1 | 5/2002 | McDaniel et al. |
| 6,395,666 B1 | 5/2002 | McDaniel et al. |
| 6,462,161 B1 | 10/2002 | Cady et al. |
| 6,469,188 B1 | 10/2002 | Miller et al. |
| 6,482,905 B1 | 11/2002 | Schmidt et al. |
| 6,489,263 B2 | 12/2002 | Murray et al. |
| 6,509,427 B1 | 1/2003 | Welch et al. |
| 6,515,086 B1 | 2/2003 | Razavi |
| 6,524,987 B1 | 2/2003 | Collins et al. |
| 6,531,565 B2 | 3/2003 | Kellum et al. |
| 6,541,413 B1 | 4/2003 | Razavi et al. |
| 6,548,441 B1 | 4/2003 | McDaniel et al. |
| 6,548,442 B1 | 4/2003 | McDaniel et al. |
| 6,573,344 B1 | 6/2003 | Hawley et al. |
| 6,576,583 B1 | 6/2003 | McDaniel et al. |
| 6,583,241 B1 | 6/2003 | Beach et al. |

(56) References Cited

U.S. PATENT DOCUMENTS

| | | |
|---|---|---|
| 6,613,712 B1 | 9/2003 | McDaniel et al. |
| 6,613,852 B2 | 9/2003 | McDaniel et al. |
| 6,632,894 B1 | 10/2003 | McDaniel et al. |
| 6,653,416 B2 | 11/2003 | McDaniel et al. |
| 6,667,274 B1 | 12/2003 | Hawley et al. |
| 6,686,490 B1 | 2/2004 | Kol et al. |
| 6,693,153 B2 | 2/2004 | Miller et al. |
| 6,750,302 B1 | 6/2004 | McDaniel et al. |
| 6,770,712 B2 | 8/2004 | Golze et al. |
| 6,831,141 B2 | 12/2004 | McDaniel et al. |
| 6,833,415 B2 | 12/2004 | Kendrick et al. |
| 6,897,176 B2 | 5/2005 | Nakayama et al. |
| 6,936,667 B2 | 8/2005 | Jensen et al. |
| 6,939,928 B1 | 9/2005 | Kawai et al. |
| 6,982,306 B2 | 1/2006 | Martin et al. |
| 6,984,603 B2 | 1/2006 | McDaniel et al. |
| 6,992,032 B2 | 1/2006 | McDaniel et al. |
| 6,998,441 B2 | 2/2006 | Golze et al. |
| 7,002,031 B2 | 2/2006 | Resconi et al. |
| 7,026,494 B1 | 4/2006 | Yang et al. |
| 7,041,617 B2 | 5/2006 | Jensen et al. |
| 7,064,225 B2 | 6/2006 | Thorn et al. |
| 7,094,857 B2 | 8/2006 | Sukhadia et al. |
| 7,109,277 B2 | 9/2006 | Hawley et al. |
| 7,119,153 B2 | 10/2006 | Jensen et al. |
| 7,125,821 B2 | 10/2006 | Xu et al. |
| 7,148,298 B2 | 12/2006 | Jensen et al. |
| 7,163,906 B2 | 1/2007 | McDaniel et al. |
| 7,199,073 B2 | 4/2007 | Martin et al. |
| 7,226,886 B2 | 6/2007 | Jayaratne et al. |
| 7,247,594 B2 | 7/2007 | Jayaratne et al. |
| 7,294,599 B2 | 11/2007 | Jensen et al. |
| 7,312,279 B2 | 12/2007 | Kwalk |
| 7,312,283 B2 | 12/2007 | Martin et al. |
| 7,345,113 B2 | 3/2008 | Van Dun et al. |
| 7,393,965 B2 | 7/2008 | Tohi et al. |
| 7,396,888 B2 | 7/2008 | Razavi |
| 7,449,527 B2 | 11/2008 | Razavi |
| 7,468,452 B1 | 12/2008 | Martin et al. |
| 7,470,758 B2 | 12/2008 | Jensen et al. |
| 7,479,529 B2 | 1/2009 | Wenzel et al. |
| 7,501,372 B2 | 3/2009 | Thorn et al. |
| 7,517,939 B2 | 4/2009 | Yang et al. |
| 7,521,572 B2 | 4/2009 | Jayaratne et al. |
| 7,534,842 B2 | 5/2009 | Jayaratne et al. |
| 7,576,163 B2 | 8/2009 | Yang et al. |
| 7,601,665 B2 | 10/2009 | McDaniel et al. |
| 7,619,047 B2 | 11/2009 | Yang et al. |
| 7,625,982 B2 | 12/2009 | Martin et al. |
| 7,629,284 B2 | 12/2009 | Jensen et al. |
| 7,632,907 B2 | 12/2009 | Sukhadia et al. |
| 7,652,160 B2 | 1/2010 | Yang et al. |
| 7,666,959 B2 | 2/2010 | Razavi |
| 7,696,280 B2 | 4/2010 | Krishnaswamy et al. |
| 7,732,542 B2 | 6/2010 | Yang et al. |
| 7,763,561 B2 | 7/2010 | McDaniel et al. |
| 7,790,820 B2 | 9/2010 | Jensen et al. |
| 7,842,763 B2 | 11/2010 | Jensen et al. |
| 7,847,009 B2 | 12/2010 | Wong et al. |
| 7,863,210 B2 | 1/2011 | Murray et al. |
| 7,884,163 B2 | 2/2011 | McDaniel et al. |
| 7,884,165 B2 | 2/2011 | McDaniel et al. |
| 7,906,603 B2 | 3/2011 | McDaniel et al. |
| 7,910,763 B2 | 3/2011 | Jayaratne et al. |
| 7,919,639 B2 | 4/2011 | Murray et al. |
| 7,951,881 B2 | 5/2011 | Sukhadia et al. |
| 7,960,487 B2 | 6/2011 | Yang et al. |
| 8,012,900 B2 | 9/2011 | Murray et al. |
| 8,048,679 B2 | 11/2011 | DesLauriers et al. |
| 8,080,681 B2 | 12/2011 | Murray et al. |
| 8,114,946 B2 | 2/2012 | Yang et al. |
| 8,119,553 B2 | 2/2012 | Yang et al. |
| 8,129,472 B2 | 3/2012 | Turner et al. |
| 8,138,113 B2 | 3/2012 | Yang et al. |
| 8,501,651 B2 | 8/2013 | Ding et al. |
| 8,536,391 B2 | 9/2013 | Small et al. |
| 2004/0059070 A1 | 3/2004 | Whitte et al. |
| 2004/0152591 A1 | 8/2004 | Jin et al. |
| 2005/0101772 A1 | 5/2005 | Schottek et al. |
| 2005/0148460 A1 | 7/2005 | Marin et al. |
| 2005/0203261 A1 | 9/2005 | Sukhadia et al. |
| 2005/0288461 A1 | 12/2005 | Jensen et al. |
| 2006/0189769 A1 | 8/2006 | Hoang et al. |
| 2007/0060726 A1 | 3/2007 | Razavi |
| 2007/0073013 A1 | 3/2007 | Razavi et al. |
| 2009/0240010 A1 | 9/2009 | McDaniel et al. |
| 2010/0179055 A1 | 7/2010 | Prades et al. |
| 2010/0221475 A1 | 9/2010 | Sukhadia et al. |
| 2010/0280199 A1 | 11/2010 | McDaniel et al. |
| 2011/0035193 A1 | 2/2011 | Deslauriers et al. |
| 2011/0082323 A1 | 4/2011 | Small et al. |
| 2012/0059134 A1 | 3/2012 | Yang et al. |
| 2013/0059100 A1 | 3/2013 | Hlavinka et al. |
| 2013/0059103 A1 | 3/2013 | Yang et al. |
| 2013/0059982 A1 | 3/2013 | Yu et al. |

FOREIGN PATENT DOCUMENTS

| | | |
|---|---|---|
| DE | 1959322 A1 | 7/1971 |
| EP | 0416928 A2 | 3/1991 |
| EP | 0416928 A3 | 11/1991 |
| EP | 0628574 A1 | 12/1994 |
| EP | 0416928 B1 | 3/1995 |
| EP | 0666267 B1 | 8/1995 |
| EP | 0729978 A1 | 9/1996 |
| EP | 0853086 A1 | 7/1998 |
| EP | 0881236 A1 | 12/1998 |
| EP | 1201711 A1 | 5/2002 |
| EP | 1276775 A1 | 1/2003 |
| EP | 1325899 A1 | 7/2003 |
| EP | 1405866 A1 | 4/2004 |
| EP | 1276775 B1 | 8/2004 |
| JP | 09059289 A | 3/1997 |
| WO | 9914219 A1 | 3/1999 |
| WO | 9948934 A1 | 9/1999 |
| WO | 9960033 A1 | 11/1999 |
| WO | 0024792 A1 | 5/2000 |
| WO | 00/37512 | 6/2000 |
| WO | 0037512 A2 | 6/2000 |
| WO | 0105852 A1 | 1/2001 |
| WO | 0123433 A1 | 4/2001 |
| WO | 0123434 A1 | 4/2001 |
| WO | 0141920 A1 | 6/2001 |
| WO | 0144309 A1 | 6/2001 |
| WO | 0158587 A1 | 8/2001 |
| WO | 0170827 A1 | 9/2001 |
| WO | 0170828 A1 | 9/2001 |
| WO | 0183498 A1 | 11/2001 |
| WO | 0190239 A1 | 11/2001 |
| WO | 02074854 A2 | 9/2002 |
| WO | 03008468 A2 | 1/2003 |
| WO | 03020821 A1 | 3/2003 |
| WO | 2004087770 A1 | 10/2004 |
| WO | 2005118654 A1 | 12/2005 |
| WO | 2006008127 A1 | 1/2006 |
| WO | 2007024773 A1 | 3/2007 |
| WO | 2007037836 A2 | 4/2007 |
| WO | 2007037836 A3 | 4/2007 |
| WO | 2007092753 A2 | 8/2007 |
| WO | 2007092753 A3 | 8/2007 |
| WO | 2007101053 A1 | 9/2007 |
| WO | 2008002969 A2 | 1/2008 |
| WO | 2008003020 A2 | 1/2008 |
| WO | 2009117128 A1 | 9/2009 |
| WO | 2010098827 A1 | 9/2010 |
| WO | 2014066602 A1 | 5/2014 |
| WO | 2014066618 A1 | 5/2014 |

OTHER PUBLICATIONS

Hultzsch, K. Chem. Ber. 1949, 82(1), 16-25.*

Ziguener, G.; Jellnick, K. Monatshefte für Chemie, 1959, 90(3), 297-305.*

(56) References Cited

OTHER PUBLICATIONS

Bird, R. Byron, et al., "Fluid Mechanics," Dynamics of Polymeric Liquids, vol. 1, Second Edition, 1987, cover page, publishing page, pp. xiii-xviii, and 171-172, John Wiley & Sons, Inc.

Cotton, F. Albert, et al., Advanced Inorganic Chemistry, Sixth Edition, cover page, title page, contents page and pp. ix-x, Mar. 30, 1999, John Wiley & Sons, Inc.

Hawley's Condensed Chemical Dictionary, Eleventh Edition, 1987, cover page, contents page, and pp. 862-863, Van Nostrand Reinhold Company, New York.

Hieber, C. A., et al., "Shear-Rate-Dependence Modeling of Polymer Melt Viscosity," Jul. 1992, pp. 931-938, vol. 32, No. 14, Polymer Engineering and Science.

Hieber, C. A., et al., "Some correlations involving the shear viscosity of polystyrene melts," 1989, pp. 321-332, vol. 28, No. 4, Rheologica Acta.

Hubert, L., et al., "Physical and Mechanical Properties of Polyethylene for Pipes in Relation to Molecular Architecture. II. Short-Term Creep of Isotropic and Drawn Materials," Journal of Applied Polymer Science, vol. 84, 2002, pp. 2308-2317, Wiley Periodicals, Inc.

Laurent, E., "Comprehensive Evaluation of the Long-Term Mechanical Properties of PE100 Resins Meeting the Requirements of Modern Installation Techniques," Plastics pipes XI, 2005, publishing page, pp. 63-73, Woodhead Publishing Limited.

McNaught, Alan D., et al., "Compendium of Chemical Terminology," International Union of Pure and Applied Chemistry, Second edition, 1997, Wiley-Blackwell.

Periodic table of the elements, Feb. 4, 1985, C&EN, p. 27.

Pinnavaia, Thomas J., "Intercalated Clay Catalysts," Apr. 22, 1983, vol. 220, No. 4595, pp. 365-371, Science.

Thomas, J. M., "Sheet Silicate Intercalates: New Agents for Unusual Chemical Conversions," Intercalation Chemistry, 1982, Chapter 3, pp. 55-99, Academic Press, Inc.

Filing receipt and specification for patent application entitled "Novel Catalyst Compositions and Methods of Making and Using Same," by Mark L. Hlavinka, et al., filed Oct. 25, 2012 as U.S. Appl. No. 13/660,850.

Chien, James C. W., et al., "Olefin Copolymerization with Metallocene Catalysts. III. Supported Metallocene/Methylaluminoxane Catalyst for Olefin Copolymerization," Journal of Polymer Science: Part A: Polymer Chemistry, 1991, pp. 1603-1607, vol. 29, John Wiley & Sons, Inc.

Kaminaka, Manabu, et al., "Polymerization of Propene with Catalyst Systems Composed of Al2O3- or MgCl2-Supported Et[IndH4]2ZrCl2 and AlR3 (R=CH3, C2H5)," Makromol. Chem., Rapid Commun., 1991, pp. 367-372, vol. 12, Hüthig & Wepf Verlag, Basel.

Kaminsky, Walter, et al., "High Melting Polypropenes by Silica-Supported Zirconocene Catalysts," Makromol. Chem., Rapid Commun., 1993, pp. 239-243, vol. 14, Hüthig & Wepf Verlag, Basel.

Kaminsky, Walter, et al., "Metallocenes for Polymer Catalysis," Advances in Polymer Science, 1997, pp. 143-187, vol. 127, Springer-Verlag Berlin Heidelberg.

Sacchi, Maria Carmela, et al., "Silica-Supported Metallocenes: Stereochemical Comparison Between Homogeneous and Heterogeneous Catalysis," Macromol. Rapid Commun., 1995, pp. 581-590, vol. 16, Hüthig & Wepf Verlag, Zug.

Soga, Kazuo, et al., "Highly Isospecific SiO2-Supported Zirconocene Catalyst Activated by Ordinary Alkylaluminiums," Macromol. Rapid Commun., 1994, pp. 139-143, vol. 15, Hüthig & Wepf Verlag, Basel.

Soga, Kazuo, et al., "Polymerization of Propene with the Heterogeneous Catalyst System Et[IndH4]2ZrCl2/MAO/SiO2 Combined with Trialkylaluminium," Makromol. Chem., Rapid Commun., 1992, pp. 221-224, vol. 13, Hüthig & Wepf Verlag, Basel.

Soga, Kazuo, et al., "Polymerization of Propene with Zirconocene-Containing Supported Catalysts Activated by Common Trialkylaluminiums," Makromol. Chem., 1993, pp. 1745-1755, vol. 194, Hüthig & Wepf Verlag, Basel.

Alt, Helmut G., et al., "ansa-Metallocenkomplexe des Typs (C13H8-SiR2-C9H6_nR'n)ZrCl2 (n=0, 1; R=Me, Ph, Alkenyl; R'=Alkyl, Alkenyl): Selbstimmobilisierende Katalysatorvorstufen für die Ethylenpolymerisation," Journal of Organometallic Chemistry, 1998, pp. 229-253, vol. 562, Elsevier Science S.A.

Alt, Helmut G., et al., "C1-Bridged fluorenylidene cyclopentadienylidene complexes of the type (C13H8-CR1R2-C5H3R)ZrCl2 (R1, R2=alkyl, phenyl, alkenyl; R=H, alkyl, alkenyl, substituted silyl) as catalyst precursors for the polymerization of ethylene and propylene," Journal of Organometallic Chemistry, 1998, pp. 87-112, vol. 568, Elsevier Science S.A.

Alt, Helmut G., et al., "C1-verbrückte Fluorenyliden—Indenylidenkomplexe des Typs (C13H8-CR2-C9H6_nR'n) ZrCl2 (n=0, 1; R=Me, Ph, Butenyl; R'=Alkyl, Alkenyl) als Metallocenkatalysatorvorstufen für die Ethylenpolymerisation," Journal of Organometallic Chemistry, 1998, pp. 153-181, vol. 562, Elsevier Science S.A.

Alt, Helmut G., et al., "C2-bridged metallocene dichloride complexes of the types (C13H8-CH2CHR-C9H6_nR'n) ZrCl2 and (C13H8-CH2CHR-C13H8)MCl2(n=0, 1; R=H, alkenyl; R'=alkenyl, benzyl; M=Zr, Hf) as self-immobilizing catalyst precursors for ethylene polymerization," Journal of Organometallic Chemistry, 1999, pp. 1-16, vol. 580, Elsevier Science S.A.

Alt, Helmut G., et al., "Syndiospezifische Polymerisation von Propylen: 2- and 2,7-substituierte Metallocenkomplex des Typs (C13H8_nRnCR'2C5H4)MCl2(n=1,2; R=Alkoxy, Alkyl, Aryl, Hal; R'=Me, Ph; M=Zr, Hf)," Journal of Organometallic Chemistry, 1996, pp. 39-54, vol. 522, Elsevier Science S.A.

Alt, Helmut G., et al., "Verbrückte Indenyliden—Cyclopentadienylidenkomplexe des Typs (C9H5CH2Ph-X-C5H4)MCl2 (X=CMe2, Sime2, M=Zr, Hf) als Metallocenkatalysatoren für die Ethylenpolymerisation. Die Molekülstrukfuren von (C9H5CH2Ph-CMe2-C5H4)MCl2 (M=Zr, Hf)," Journal of Organometallic Chemistry, 1998, pp. 111-121, vol. 558, Elsevier Science S.A.

Amor, José Ignacio, et al., "Synthesis of bis(tert-butyl)cyclopentadienyl derivatives of bitanium and zirconium. NMR spectra and dynamic behaviour of the base-free [Zr(1,3-tBu2-•5-C5H3)(CH2Ph)2]+ cation," Journal of Organometallic Chemistry, 1995, pp. 127-131, vol. 497, Elsevier Science S.A.

Arnett, Raymond L., et al., "Zero-Shear Viscosity of Some Ethyl Branched Paraffinic Model Polymers," J. Phys. Chem., 1980, pp. 649-652, vol. 84, No. 6, American Chemical Society.

Breslow, David S., et al., "Bis-(Cyclopentadienyl)-Titanium Dichloride-Alkylaluminum Complexes as Catalysts for the Polymerization of Ethylene," Journal of the American Chemical Society, Communications to the Editor, Sep. 20, 1957, pp. 5072-5073, vol. 79.

Collins, Scott, et al., "Polymerization of Propylene Using Supported, Chiral, ansa-Metallocene Catalysts: Production of Polypropylene with Narrow Molecular Weight Distributions," Macromolecules, 1992, pp. 1780-1785, vol. 25, No. 6, American Chemical Society.

Daniell, W., et al., "Enhanced surface acidity in mixed alumina-silicas: a low-temperature FTIR study," Applied Catalysis A: General, 2000, pp. 247-260, vol. 196, Elsevier Science B.V.

Das, P. K., "Computational Chemistry of Metallocene Catalyzed Olefin Polymerization," 21st Century Symp. S.W. Regional American Chemical Society Meeting, Oct. 25-28, 2003, pp. 2-12, Oklahoma.

Deppner, Matthias, "Substituted idenyl complexes of zirconium as catalysts for olefin polymerization," Dissertation, Feb. 1998, pp. 1-77 plus cover, information, and content pages, University of Bayreuth, Germany.

Erker, Gerhard, et al., "Convenient Route to Monocyclopentadienylzirconium (IV) Complexes," Inorg. Chem., 1982, pp. 1277-1278, vol. 21, American Chemical Soceity.

Filing receipt and specification for patent application entitled "Novel Polymer Compositions and Methods of Making and Using Same," by Mark L. Hlavinka, et al., filed Jan. 29, 2013 as U.S. Appl. No. 13/753,289.

Filing receipt and specification for patent application entitled "Novel Catalyst Compositions and Methods of Making and Using Same," by Mark L. Hlavinka, et al., filed Jan. 29, 2013 as U.S. Appl. No. 13/753,294.

(56) References Cited

OTHER PUBLICATIONS

Foreign communication from a related counterpart application—International Search Report and Written Opinion, PCT/US2007/062555, Aug. 2, 2007, 8 pages.
Foreign communication from a related counterpart application—International Preliminary Report on Patentability, PCT/US2007/062555, Aug. 26, 2008, 6 pages.
Foreign communication from a related counterpart application—International Search Report and Written Opinion, PCT/US2006/032542, Aug. 9, 2007, 20 pages.
Foreign communication from a related counterpart application—International Preliminary Report on Patentability, PCT/US2006/032542, Mar. 18, 2008, 14 pages.
Foreign communication from a related counterpart application—International Search Report and Written Opinion, PCT/US2007/061519, Sep. 12, 2007, 13 pages.
Foreign communication from a related counterpart application—International Preliminary Report on Patentability, PCT/US2007/061519, Aug. 5, 2008, 9 pages.
Foreign communication from a related counterpart application—International Search Report and Written Opinion, PCT/US2009/001741, Aug. 5, 2009, 8 pages.
Foreign communication from a related counterpart application—International Preliminary Report on Patentability, PCT/US2009/001741, Sep. 21, 2010, 6 pages.
Gladysz, J. A., et al., "Reactions of organocyclopropanes and spirocycles with metal atoms," XP-002424275, Chemical Abstracts Service, (Journal of the American Chemical Society, 1979, pp. 3388-3390, vol. 101, No. 12), 2 pages.
Hitchcock, Peter B., et al., "Ligand Redistribution Reactions as a Route to Cyclopentadienyl- or 1-aza-allylzirconium(IV) Trichlorides and the X-ray Structures of [{Zr(LL')Cl2(μ-Cl)}2] and [Zr(LL')2Cl2] [LL'=N(R)C(But)CHR, R=SiMe3]," Polyhedron, 1995, pp. 2745-2752, vol. 14, No. 19, Elsevier Science Ltd.
Jany, Gerhard, et al., "para-Fluoro benzyl substituted bis(indenyl) metallocenes as catalyst precursors in ethene polymerization," Journal of Organometallic Chemistry, 1998, pp. 173-178, vol. 553, Elsevier Science S.A.
Janzen, J., et al., "Diagnosing long-chain branching in polyethylenes," Journal of Molecular Structure, 1999, pp. 569-584 plus comments and information pages, vol. 485-486, Elsevier Science B.V.
Jung, Michael, "ansa Metallocene complexes of zirconium as catalysts for the olefin polymerization," Dissertation, 1997, pp. 1-143 and A-1 to A-64 plus cover, information, and content pages, University of Bayreuth, Germany.
Kajigaeshi, Shoji, et al., "Selective Preparation of Fluorene Derivatives Using the t-Butyl Function as a Positional Protective Group," Bull. Chem. Soc. Jpn., Jan. 1986, pp. 97-103, vol. 59, No. 1, The Chemical Society of Japan.
Kokko, Esa, et al., "Influence of the Catalyst and Polymerization Conditions on the Long-Chain Branching of Metallocene-Catalyzed Polyethenes," Journal of Polymer Science: Part A: Polymer Chemistry, 2000, pp. 376-388, vol. 38, John Wiley & Sons, Inc.
Kolodka, E., et al., "Long-chain branching in slurry polymerization of ethylene with zirconocene dichloride/modified methylaluminoxane," Polymer, 2000, pp. 3985-3991, vol. 41, Elsevier Science Ltd.
Köppl, Alexander, "Aluminoxane based immobilized cocatalysts for heterogeneous olefin polymerization," Dissertation, updated Dec. 13, 1997, pp. 1-160 plus cover, information, and content pages, University of Bayreuth, Germany.
Köppl, Alexander, et al., "Heterogeneous metallocene catalysts for ethlene polymerization," Journal of Molecular Catalysis A: Chemical, 2001, pp. 23-32, vol. 165, Elsevier Science B.V.
Kravchenko, Raisa, et al., "Propylene Polymerization with Chiral and Archiral Unbridged 2-Arylindene Metallocenes," Organometallics, 1997, pp. 3635-3639, vol. 16, No. 16, American Chemical Society.
Li, Hongbo, et al., Coordination Copolymerization of Severely Encumbered Isoalkenes with Ethylene: Enhanced Enchainment Mediated by Binuclear Catalysts and Cocatalysts, J. Am. Chem. Soc., 2005, pp. 14756-14768, vol. 127, No. 42, American Chemical Society.
Licht, Erik, "Metallacyclic zirconocene complexes as catalysts for homogeneous and heterogeneous olefin polymerization," Dissertation, pp. 1-178 plus cover, information, and content pages, updated May 14, 1998, University of Bayreuth, Germany.
Licht, Erik H., et al., "ω-Phenylalkyl-substituted zirconocene dichloride complexes as catalyst precursors for homogeneous ethylene polymerization," Journal of Organometallic Chemistry, 2000, pp. 275-287, vol. 599, Elsevier Science, S.A.
Licht, Andrea I., et al., "Synthesis of novel metallacyclic zirconocene complexes from ω-alkenyl-functionalized zirconocene dichloride complexes and their use in the α-olefin polymerization," Journal of Organometallic Chemistry, 2002, pp. 134-148, vol. 648, Elsevier Science B.V.
Llinás, Gerardo Hidalgo, et al., "(C5Me5)SiMe3 as a mild and effective reagent for transfer of the C5Me5 ring: an improved route to monopentamethylcyclopentadienyl trihalides of the group 4 elements," Journal of Organometallic Chemistry, 1988, pp. 37-40, vol. 304, Elsevier Sequoia S.A.
Lund, Eric C., et al., "Rapid and Efficient Procedures for the Synthesis of Monocyclopentadienyl Complexes of Hafnium and Zirconium," Organometallics, 1990, pp. 2426-2427, vol. 9, No. 9, American Chemical Society.
Malmberg, Anneli, et al., "Long-Chain Branching in Metallocene-Catalyzed Polyethylenes Investigated by Low Oscillatory Shear and Uniaxial Extensional Rheometry," Macromolecules, 2002, pp. 1038-1048, vol. 35, No. 3, American Chemical Society.
Marks, Tobin J., "Surface-Bound Metal Hydrocarbyls. Organometallic Connections between Heterogeneous and Homogeneous Catalysis," Accounts of Chemical Research, Feb. 1992, pp. 57-65, vol. 25, No. 2, American Chemical Society.
Martín, Avelino, et al., "Molecular structure of trichloro(•5-pentamethylcyclopentadienyl)zirconium(IV)," Journal of Organometallic Chemistry, 1994, pp. C10-C11, vol. 480, Elsevier Science S.A.
Naga, N., et al., "Stereochemical control in propylene polymerization with non-bridged metallocene dichloride/methylaluminoxane," Polymer, 1998, pp. 2703-2708, vol. 39, No. 13, Elsevier Science Ltd.
Natta, Giulio, et al., "A Crystallizable Organometallic Complex Containing Titanium and Aluminum," Journal of the American Chemical Society, Communications to the Editor, Jun. 5, 1957, pp. 2975-2976, vol. 79.
Negishi, E.-I., "Product Class 11: Organometallic Complexes of Zirconium and Hafnium," Science of Synthesis, XP-001243520, 2003, pp. 681-775.
Office Action dated Apr. 4, 2011 (10 pages), U.S. Appl. No. 12/814,589, filed Jun. 14, 2010.
Office Action dated Oct. 7, 2010 (10 pages), U.S. Appl. No. 12/814,589, filed Jun. 14, 2010.
Peifer, Bernd, "Self-immobilizing Metallocene Catalysts for the Polymerization of Olefins," PhD. Dissertation, 1995, 132 pages, University of Bayreuth, Germany.
Foreign communication from a related counterpart application—International Search Report, PCT/US2013/066583, Jan. 22, 2014, 3 pages.
Office Action dated Mar. 27, 2014 (65 pages), U.S. Appl. No. 13/660,850, filed Oct. 25, 2012.
Office Action dated Jun. 9, 2014 (51 pages), U.S. Appl. No. 13/753,289, filed Jan. 29, 2013.
Foreign communication from a related counterpart application—International Search Report, PCT/US2013/066550, Jan. 22, 2014, 4 pages.
Hultzsch, Kurt, "Studien auf dem Gebiet der Phenol-Formaldehyd-Harze, XIV. Mittel!: Über die Ammoniak-Kondensation und die Reaktion von Phenolen mit Hexamethylentetramin (Phenol-formaldehyde resins. XIV. The ammonia condensation and the reaction of phenols with hexamethylenetetramine)," XP009175438, Chemische Berichte, vol. 82, No. 1, Jan. 1, 1949, pp. 16-25.
Zigeuner G., et al., "Über die Struktur der künstlichen Harze VIII. Mitt.: Zur Darstellung von 3,5-disubstituierten 2-Hydroxybenzaldehyden (Structure of synthetic resins. VIII. The

(56) References Cited

OTHER PUBLICATIONS preparation of 3,5-disubstituted 2-hydroxybenzaldehydes) ," XP009175444, Monatshefte fur Chemie, Jan. 1, 1959, pp. 297-305, vol. 90, No. 3, Springer Verlag.

Foreign communication from a related counterpart application—Invitation to Pay Additional Fees, PCT/US2014/012689, Apr. 3, 2014, 5 pages.

Foreign communication from a related counterpart application—International Search Report, PCT/US2014/012723, Apr. 14, 2014, 3 pages.

Zigeuner, G., et al., "Structure of Synthetic Resins. VIII. The preparation of 3,5-disubstituted 2-hydroxybenzaldehydes," Monatshefte Fur Chemie, Springer Verlag Wien, at. vol. 90, No. 3, Jan. 1, 1959, pp. 297-305.

Hultzsch, K, "The ammonia condensation and the reaction of phenols with hexamethylenetetramine", Chemische Berichte, VCH, DE, vol. 82, No. 1, Jan. 1, 1949, pp. 16-25.

International Application PCT/US2013/066550 Search Report, Jan. 22, 2014.

Podzimek, Stepan, "A review of the analysis of branched polymers by SEC-MALS," Jan. 2002, 5 pages, American Laboratory.

Poli, Rinaldo, "Monocyclopentadienyl Halide Complexes of the d- and f-Block Elements," XP-002422576, Chem. Rev., 1991, pp. 509-551, vol. 91, No. 4, American Chemical Society.

Renaut, P., et al., "Cyclopentadienylhafnium Trichloride, Its Synthesis and Use to Prepare a Chiral Hafnium Compound," Journal of Organometallic Chemistry, 1977, pp. C35-C36, vol. 127, Elsevier Sequoia S.A., Lausanne.

Sandman, Daniel J., et al., "5,6:11,12-Bis(ditelluro)tetracene: Synthesis, Molecular, and Supramolecular Properties," Organometallics, 1982, pp. 739-742, vol. 1, No. 5, American Chemical Society.

Schumann, Herbert, et al., "Synthesis, characterization, and catalytic properties of bis[alkylindenyl]-, bis [alkenylindenyl]- and [alkenylindenyl(cyclopentadienyl)]zirconium dichloride complexes," Journal of Organometallic Chemistry, 2001, pp. 31-40, vol. 636, Elseiver Science B.V.

Shida, M., et al., "Correlation of Low Density Polyethylene Rheological Measurements with Optical and Processing Properties," Polymer Engineering and Science, Nov. 1977, pp. 769-774 plus cover page, vol. 17, No. 11, The Society of Plastics Engineers, Inc.

Sitzmann, Helmut, et al., "Titan-, Zirconium- und Hafniumkomplexe mit 1, 2, 4-Tri-tert-butyl-cyclopentadienyl-Liganden," Chem. Ber., 1994, pp. 3-9, vol. 127, VCH Verlagsgesellschaft mbH, Weinheim.

Soga, Kazuo, et al., "Activation of SiO2-supported zirconocene catalysts by common trialkylaluminiums," Makromol. Chem., 1993; pp. 3499-3504, vol. 194, Hüthig & Wepf Verlag, Basel.

Stone, Keith J., et al., "An Exceptionally Simple and Efficient Method for the Preparation of a Wide Variety of Fulvenes," The Journal of Organic Chemistry, Jun. 1, 1984, pp. 1849-1853, vol. 49, No. 11, American Chemical Society.

Sukhadia, Ashish M., "The Complex Effects of Long Chain Branching on the Blown Film Performance of LLDPE Resins," Antec Annual Technical Conference, Conference Proceedings, vol. II—Materials, pp. 1481-1486 plus cover page, May 5-9, 2002, California, Society of Plastics Engineers.

Villar, Marcelo A., et al., "Rheological characterization of molten ethylene-$\alpha$-olefin copolymers synthesized with Et[Ind]2ZrCl2MAO catalyst," Polymer, 2001, pp. 9269-9279, vol. 42, Elsevier Science Ltd.

Walter, Philipp, et al., "Influence of zirconocene structure and propene content on melt rheology of polyethene and ethene propene copolymers," Polymer Bulletin, 2001, pp. 205-213, vol. 46, Springer-Verlag.

Wengrovius, Jeffrey H., et al., "Attempts to Prepare Alkylidene Zirconium Complexes by Hydrogen Atom Abstraction," Journal of Organometallic Chemistry, 1981, pp. 319-327, vol. 205, Elsevier Sequoia S.A., Lausanne.

Winter, Charles H., et al., "Cyclopentadienylmetal Trichloride Formation versus Metallocene Dichloride Formation in the Reactions of Silylated Cyclopentadienes with Zirconium and Hafnium Chlorides. Crystal Structure of (1,3-Bis(trimethylsilyl)cyclopentadienyl)titanium Trichloride," Organometallics, 1991, pp. 210-214, vol. 10, No. 1, American Chemical Society.

Zenk, Roland, "Tailor-made bridged metallocene dichloride complexes as catalyst precursors for the stereospecific homogeneous polymerization of propylene," Dissertation, 1994, 186 pages, University of Bayreuth, Germany.

Zhang, Yong, et al., "Some Mixed Cyclopentadienyl-Indenyl Zirconium Complexes with PhCH2 or PhCH2CH2 Substituents in Ethylene Polymerization," Journal of Polymer Science: Part A: Polymer Chemistry, 2005, pp. 1261-1269, vol. 43, Wiley Periodicals, Inc.

* cited by examiner

Figure 1 (('Bu)LZrCl₂(Et₂O)

CATALYST COMPOSITIONS AND METHODS OF MAKING AND USING SAME

CROSS REFERENCE TO RELATED APPLICATIONS

Not applicable.

STATEMENT REGARDING FEDERALLY SPONSORED RESEARCH OR DEVELOPMENT

Not applicable.

BACKGROUND

The present disclosure generally relates to catalyst systems and polymer compositions. Particularly, the present disclosure relates to novel catalyst compositions for the production of high-density polymer compositions.

FIELD

Polyolefins are plastic materials useful for making a wide variety of valued products due to their combination of features such as stiffness, ductility, barrier properties, temperature resistance, optical properties, availability, and low cost. In particular, polyethylene (PE) is one of the largest volume polymers consumed in the world. It is a versatile polymer that offers high performance relative to other polymers and alternative materials such as glass or metal. An important PE product is piping. There exists an ongoing need for improved catalyst systems for the production of polymeric compositions.

BRIEF SUMMARY

Disclosed herein is an imine bis(phenol) compound having Structure I:

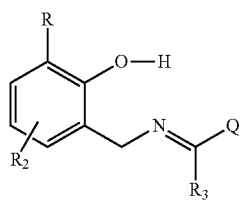

Structure I wherein O and N represent oxygen and nitrogen, respectively, R comprises a halogen, a hydrocarbyl group, or a substituted hydrocarbyl group, $R^2$ and $R^3$ can each independently be hydrogen, a halogen, a hydrocarbyl group, or a substituted hydrocarbyl group, and Q is a donor group.

Also disclosed herein is a metal salt complex of an imine (bis)phenolate compound having Structure V:

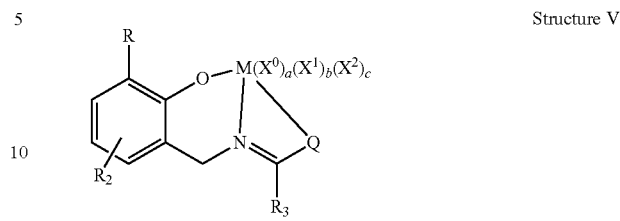

Structure V wherein O and N represent oxygen and nitrogen, respectively, R comprises a halogen, a hydrocarbyl group, or a substituted hydrocarbyl group, $R^2$ and $R^3$ can each independently be hydrogen, a halogen, a hydrocarbyl group, or a substituted hydrocarbyl group, Q is a donor group, M is a group III to group 12 transition metal or lanthanide metal having an oxidation state equal to b+2c+2, $X^0$ is a neutral ligand, a is 0, 1, or 2, $X^1$ is a monoanionic ligand, b is 0, 1, 2, 3, or 4, $X^2$ is a dianionic ligand, and c is 0, 1, or 2.

Further disclosed herein is a method comprising contacting a catalyst composition with a monomer under conditions suitable for the formation of a polymer wherein the catalyst composition comprises a metal salt complex of an imine (bis)phenolate compound, a solid oxide, and an optional metal alkyl and wherein the metal salt complex of an imine (bis)phenolate compound has Structure XIV:

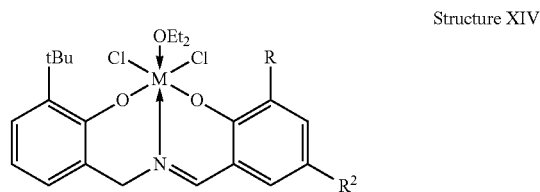

Structure XIV where M is titanium, zirconium, or hafnium, $OEt_2$ is ethoxide, R comprises a halogen, a hydrocarbyl group, or a substituted hydrocarbyl group, and $R^2$ comprises hydrogen, a halogen, a hydrocarbyl group, or a substituted hydrocarbyl group.

DETAILED DESCRIPTION

Figure 1:
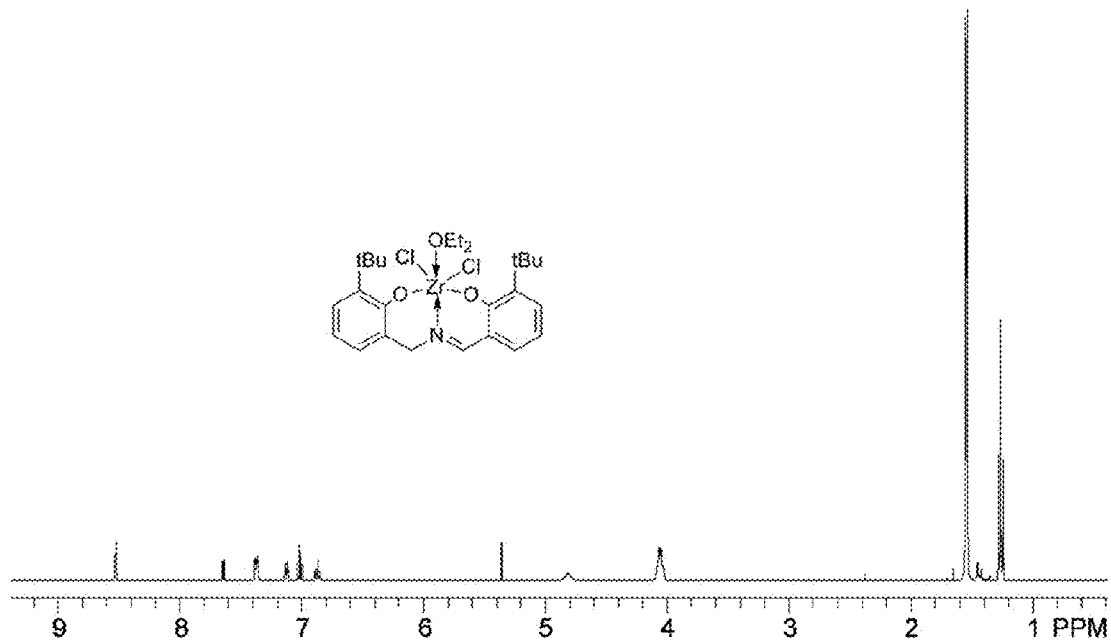
FIG. 1 is an NMR spectra of a metal salt complex of an imine (bis)phenolate compound.

Disclosed herein are novel catalyst and polymer compositions and methods of making and using same. In an embodiment, the catalyst composition comprises an imine phenol compound, alternatively an imine (bis)phenol compound, alternatively a metal salt complex comprising an imine phenol compound or alternatively, a metal salt complex comprising an imine (bis)phenol compound. In an embodiment, a method of polymerizing comprises contacting an olefin monomer with an imine phenol compound of the type described herein under conditions suitable for the formation of polymer and recovering the polymer. A polymer of the type disclosed herein may be characterized by a high-density and improved processing characteristics. In an embodiment, the polymer comprises a high-density polymer having improved barrier properties. These aspects of this disclosure are further described herein.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the table are indicated using the numbering scheme indicated in the version of the periodic table of elements published in *Chemical and Engineering News,* 63(5), 27, 1985. In some instances a group of elements may be indicated using a common name assigned to the group; for example alkali earth metals (or alkali metals) for Group 1 elements, alkaline earth metals (or alkaline metals) for Group 2 elements, transition metals for Group 3-12 elements, and halogens for Group 17 elements.

A chemical "group" is described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure that a substituent, ligand, or other chemical moiety may constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "substituted" when used to describe a group, for example, when referring to a substituted analog of a particular group, is intended to describe any non-hydrogen moiety that formally replaces a hydrogen in that group, and is intended to be non-limiting. A group or groups may also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

Unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms, and the like. Moreover, other identifiers or qualifying terms may be utilized to indicate the presence or absence of a particular substituent, a particular regiochemistry and/or stereochemistry, or the presence or absence of a branched underlying structure or backbone.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. In one aspect, the hydrogen atom(s) removed to form the "organyl group," "organylene group," or "organic group" may be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—C≡N), a carbamoyl group (—C(O)NH$_2$), an N-hydrocarbylcarbamoyl group (—C(O)NHR), or N,N'-dihydrocarbylcarbamoyl group (—C(O)NR$_2$), among other possibilities. In another aspect, the hydrogen atom(s) removed to form the "organyl group," "organylene group," or "organic group" may be attached to a carbon atom not belonging to, and remote from, a functional group, for example, —CH$_2$C(O)CH$_3$, —CH$_2$NR$_2$, and the like. An "organyl group," "organylene group," or "organic group" may be aliphatic, inclusive of being cyclic or acyclic, or may be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" may be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or may be linear or branched unless otherwise specified. Primary, secondary, and tertiary alkyl group are derived by removal of a hydrogen atom from a primary, secondary, tertiary carbon atom, respectively, of an alkane. The n-alkyl group may be derived by removal of a hydrogen atom from a terminal carbon atom of a linear alkane. The groups $RCH_2(R{\neq}H)$, $R_2CH(R{\neq}H)$, and $R_3C$ $(R{\neq}H)$ are primary, secondary, and tertiary alkyl groups, respectively.

A "halide" has its usual meaning; therefore, examples of halides include fluoride, chloride, bromide, and iodide.

Within this disclosure the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be reference using comprising or some other alternative language. For example, a reference to a phenyl group comprising a substituent at the 4 position refers to a group having a non-hydrogen atom at the 4 position and hydrogen or any non-hydrogen group at the 2, 3, 5, and 6 positions.

Embodiments disclosed herein the may provide the materials listed as suitable for satisfying a particular feature of the embodiment delimited by the term "or." For example, a particular feature of the subject matter may be disclosed as follows: Feature X can be A, B, or C. It is also contemplated that for each feature the statement can also be phrased as a listing of alternatives such that the statement "Feature X is A, alternatively B, or alternatively C" is also an embodiment of the present disclosure whether or not the statement is explicitly recited.

In an embodiment, the imine phenol compound can have Structure I:

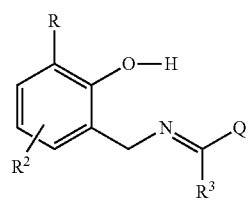

Structure I where O and N represent oxygen and nitrogen respectively and Q represents a donor group.

One or more of R, $R^2$, and $R^3$, may each be the same or different and may be selected from the embodiments described herein. R can be a halogen, a hydrocarbyl group, or a substituted hydrocarbyl group. In an embodiment R is not hydrogen. $R^2$ and $R^3$ can each independently be hydrogen, a halogen, a hydrocarbyl group, or a substituted hydrocarbyl group. These substituents are described in more detail herein.

Referring to Structure I, generally, R, $R^2$ and $R^3$ can each independently be a hydrocarbyl group. In an embodiment, R, $R^2$ and $R^3$ can each independently be a $C_1$ to $C_{30}$ hydrocarbyl group; a $C_1$ to $C_{20}$ hydrocarbyl group; a $C_1$ to $C_{15}$ hydrocarbyl group; a $C_1$ to $C_{10}$ hydrocarbyl group; or a $C_1$ to $C_5$ hydrocarbyl group. In yet other embodiments, R, $R^2$ and $R^3$ can each independently be a $C_3$ to $C_{30}$ aromatic group; a $C_3$ to $C_{20}$ aromatic group; a $C_3$ to $C_{15}$ aromatic group; or a $C_3$ to $C_{10}$ aromatic group.

In an aspect, R, $R^2$ and $R^3$ can each independently be a $C_1$ to $C_{30}$ alkyl group, a $C_4$ to $C_{30}$ cycloalkyl group, a $C_4$ to $C_{30}$ substituted cycloalkyl group, a $C_3$ to $C_{30}$ aliphatic heterocyclic group, a $C_3$ to $C_{30}$ substituted aliphatic heterocyclic group, a $C_6$ to $C_{30}$ aryl group, a $C_6$ to $C_{30}$ substituted aryl group, a $C_7$ to $C_{30}$ aralkyl group, a $C_7$ to $C_{30}$ substituted aralkyl group, a $C_3$ to $C_{30}$ heteroaryl group, or a $C_3$ to $C_{30}$ substituted heteroaryl group. In an embodiment, R, $R^2$ and $R^3$ can each independently be a $C_1$ to $C_{15}$ alkyl group, a $C_4$ to $C_{20}$ cycloalkyl group, a $C_4$ to $C_{20}$ substituted cycloalkyl group, a $C_3$ to $C_{20}$ aliphatic heterocyclic group, a $C_3$ to $C_{20}$ substituted aliphatic heterocyclic group, a $C_6$ to $C_{20}$ aryl group, a $C_6$ to $C_{20}$ substituted aryl group, a $C_7$ to $C_{20}$ aralkyl group, a $C_7$ to $C_{20}$ substituted aralkyl group, a $C_3$ to $C_{20}$ heteroaryl group, or a $C_3$ to $C_{20}$ substituted heteroaryl group. In other embodiments, R, $R^2$ and $R^3$ can each independently be a $C_1$ to $C_{10}$ alkyl group, a $C_4$ to $C_{15}$ cycloalkyl group, a $C_4$ to $C_{15}$ substituted cycloalkyl group, a $C_3$ to $C_{15}$ aliphatic heterocyclic group, a $C_3$ to $C_{15}$ substituted aliphatic heterocyclic group, a $C_6$ to $C_{15}$ aryl group, a $C_6$ to $C_{15}$ substituted aryl group, a $C_7$ to $C_{15}$ aralkyl group, a $C_7$ to $C_{15}$ substituted aralkyl group, a $C_3$ to $C_{15}$ heteroaryl group, or a $C_3$ to $C_{15}$ substituted heteroaryl group. In further embodiments, R, $R^2$ and $R^3$ can each independently be $C_1$ to $C_5$ alkyl group.

In an embodiment, R, $R^2$ and $R^3$ can each independently be a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, or a nonadecyl group. In some embodiments, the alkyl groups which can be utilized as R, $R^2$ and $R^3$ can each independently be substituted. Each substituent of a substituted alkyl group independently can be a halogen or a hydrocarboxy group; alternatively, a halogen; or alternatively, a hydrocarboxy group. Halogens and hydrocarboxy groups that can be utilized as substituents are independently disclosed herein and can be utilized without limitation to further describe the substituted alkyl group which can be utilized as R, $R^2$ and/or $R^3$.

In an embodiment, R, $R^2$ and $R^3$ can each independently be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, R, $R^2$ and $R^3$ can each independently be a cyclopentyl group, a substituted cyclopentyl group, a cyclohexyl group, or a substituted cyclohexyl group.

In an embodiment, each substituent for a substituted cycloalkyl group (general or specific) that can be utilized as R, $R^2$ and $R^3$ can each independently be a halogen, a hydrocarbyl group, or a hydrocarboxy group. In some embodiments, each substituent for a substituted cycloalkyl group (general or specific) that can be utilized as R, $R^2$ and $R^3$ can each independently be a halogen, an alkyl group, or an alkoxy group. Halogens, hydrocarbyl groups, hydrocarboxy groups, alkyl group, and alkoxy groups that can be utilized as substituents are independently disclosed herein and can be utilized without limitation to further describe the substituents for a substituted cycloalkyl group (general or specific) that can be utilized as R, $R^2$ and/or $R^3$.

In an aspect, R, $R^2$ and $R^3$ can each independently have Structure II:

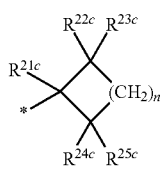

Structure II wherein the undesignated valency (*) represents the point at which the substituent (i.e., R, $R^2$ or $R^3$) attaches to the imine phenol compound of Structure I. Generally, $R^{21c}$, $R^{23c}$, $R^{24c}$, and $R^{25c}$ independently can be hydrogen or a non-hydrogen substituent, and n can be an integer from 1 to 5.

In an embodiment wherein R, $R^2$ and $R^3$ has Structure II, $R^{21c}$, $R^{23c}$, $R^{24c}$, and $R^{25c}$ can be hydrogen and $R^{22c}$ can be any non-hydrogen substituent disclosed herein; or alternatively, $R^{21c}$, $R^{23c}$, and $R^{25c}$ can be hydrogen and $R^{22c}$ and $R^{24c}$ independently can be any non-hydrogen substituent disclosed herein. In an embodiment, n can be an integer from 1 to 4; or alternatively, from 2 to 4. In other embodiments, n can be 2 or 3; alternatively, 2; or alternatively, 3.

In an embodiment, $R^{21c}$, $R^{22c}$, $R^{23c}$, $R^{24c}$, and $R^{25c}$ independently can be hydrogen, a halogen, a hydrocarbyl group, or a hydrocarboxy group; alternatively, hydrogen, a halogen, or a hydrocarbyl group. In some embodiments, $R^{21c}$, $R^{22c}$, $R^{23c}$, $R^{24c}$, and $R^{25c}$ independently can be hydrogen, a halogen, an alkyl group, or an alkoxy group. Halogens, hydrocarbyl groups, hydrocarboxy groups, alkyl group, and alkoxy groups that can be utilized as substituents are independently disclosed herein and can be utilized without limitation to further describe the R, $R^2$ or $R^3$ group having Structure II.

In an embodiment, R, $R^2$ and $R^3$ can each independently be a phenyl group or a substituted phenyl group. In an embodiment the substituted phenyl group can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group.

In an embodiment, each substituent for a substituted phenyl group independently can be a halogen, a hydrocarbyl group, or a hydrocarboxy group. In some embodiments, each substituent for a substituted phenyl group independently can be a halogen, an alkyl group, or an alkoxy group. Halogens, hydrocarbyl groups, hydrocarboxy groups, alkyl groups, and alkoxy groups that can be utilized as substituents are independently disclosed herein and can be utilized without limitation to further describe the substituents for the substituted phenyl group.

In an aspect, R, $R^2$ and $R^3$ can each independently have Structure III:

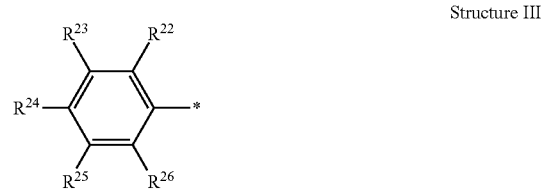

Structure III wherein the undesignated valency (*) represents the point at which the substituent (i.e., R, $R^2$ or $R^3$) attaches to the imine phenol compound of Structure I. Generally, $R^{22}$, $R^{23}$, $R^{24}$, $R^{25}$, and $R^{26}$ independently can be hydrogen or a non-hydrogen substituent. In an embodiment wherein R, $R^2$ or $R^3$ has Structure III, $R^{22}$, $R^{23}$, $R^{24}$, $R^{25}$, and $R^{26}$ can be hydrogen, $R^{23}$, $R^{24}$, $R^{25}$, and $R^{26}$ can be hydrogen and $R^{22}$ can be a non-hydrogen substituent, $R^{22}$, $R^{24}$, $R^{25}$, and $R^{26}$ can be hydrogen and $R^{23}$ can be a non-hydrogen substituent, $R^{22}$, $R^{23}$, $R^{25}$, and $R^{26}$ can be hydrogen and $R^{24}$ can be a non-hydrogen substituent, $R^{23}$, $R^{25}$, and $R^{26}$ can be hydrogen and $R^{22}$ and $R^{24}$ can be non-hydrogen substituents, $R^{23}$, $R^{24}$, and $R^{25}$ can be hydrogen and $R^{22}$ and $R^{26}$ can be non-hydrogen substituents, $R^{22}$, $R^{24}$, and $R^{26}$ can be hydrogen and $R^{23}$ and $R^{25}$ can be non-hydrogen substituents, or $R^{23}$ and $R^{25}$ can be hydrogen and $R^{22}$, $R^{24}$, and $R^{26}$ can be non-hydrogen substituents. In some embodiments wherein R, $R^2$ or $R^3$ has Structure III, $R^{23}$, $R^{24}$, $R^{25}$, and $R^{26}$ can be hydrogen and $R^{22}$ can be a non-hydrogen substituent, $R^{22}$, $R^{23}$, $R^{25}$, and $R^{26}$ can be hydrogen and $R^{24}$ can be a non-hydrogen substituent, $R^{23}$, $R^{25}$, and $R^{26}$ can be hydrogen and $R^{22}$ and $R^{24}$ can be non-hydrogen substituents, $R^{23}$, $R^{24}$, and $R^{25}$ can be hydrogen and $R^{22}$ and $R^{26}$ can be non-hydrogen substituents, or $R^{23}$ and $R^{25}$ can be hydrogen and $R^{22}$, $R^{24}$, and $R^{26}$ can be non-hydrogen substituents; alternatively, $R^{23}$, $R^{24}$, $R^{25}$, and $R^{26}$ can be hydrogen and $R^{22}$ can be a non-hydrogen substituent, $R^{22}$, $R^{23}$, $R^{25}$, and $R^{26}$ can be hydrogen and $R^{24}$ can be a non-hydrogen substituent, $R^{23}$, $R^{25}$, and $R^{26}$ can be hydrogen and $R^{22}$ and $R^{24}$ can be non-hydrogen substituents, or $R^{23}$, $R^{24}$, and $R^{25}$ can be hydrogen and $R^{22}$ and $R^{26}$ can be non-hydrogen substituents; alternatively, $R^{22}$, $R^{24}$, $R^{25}$, and $R^{26}$ can be hydrogen and $R^{23}$ can be a non-hydrogen substituent, $R^{24}$, and $R^{26}$ can be hydrogen and $R^{23}$ and $R^{25}$ can be non-hydrogen substituents; alternatively, $R^{23}$, $R^{24}$, $R^{25}$, and $R^{26}$ can be hydrogen and $R^{22}$ can be a non-hydrogen substituent, or $R^{22}$, $R^{23}$, $R^{25}$ and $R^{26}$ can be hydrogen and $R^{24}$ can be a non-hydrogen substituent; alternatively, $R^{23}$, $R^{25}$, and $R^{26}$ can be hydrogen and $R^{22}$ and $R^{24}$ can be non-hydrogen substituents, $R^{23}$, $R^{24}$, and $R^{25}$ can be hydrogen and $R^{22}$ and $R^{26}$ can be non-hydrogen substituents, or $R^{23}$ and $R^{25}$ can be hydrogen and $R^{22}$, $R^{24}$, and $R^{26}$ can be non-hydrogen substituents; or alternatively, $R^{23}$, $R^{25}$, and $R^{26}$ can be hydrogen and $R^{22}$ and $R^{24}$ can be non-hydrogen substituents, or $R^{23}$, $R^{24}$, and $R^{25}$ can be hydrogen and $R^{22}$ and $R^{26}$ can be non-hydrogen substituents. In other embodiments wherein R, $R^2$ or $R^3$ has Structure III, $R^{22}$, $R^{23}$, $R^{24}$, $R^{25}$, and $R^{26}$ can be hydrogen; alternatively, $R^{23}$, $R^{24}$, $R^{25}$, and $R^{26}$ can be hydrogen and $R^{22}$ can be a non-hydrogen substituent; alternatively, $R^{22}$, $R^{24}$, $R^{25}$, and $R^{26}$ can be hydrogen and $R^{23}$ can be a non-hydrogen substituent; alternatively, $R^{22}$, $R^{23}$, $R^{25}$, and $R^{26}$ can be hydrogen and $R^{24}$ can be a non-hydrogen substituent; alternatively, $R^{23}$, $R^{25}$, and $R^{26}$ can be hydrogen and $R^{22}$ and $R^{24}$ can be non-hydrogen substituents; alternatively, $R^{23}$, $R^{24}$, and $R^{25}$ can be hydrogen and $R^{22}$ and $R^{26}$ can be non-hydrogen substituents; alternatively, $R^{22}$, $R^{24}$, and $R^{26}$ can be hydrogen and $R^{23}$ and $R^{25}$ and can be non-hydrogen substituents; or alternatively, $R^{23}$ and $R^{25}$ can be hydrogen and $R^{22}$, $R^{24}$, and $R^{26}$ can be non-hydrogen substituents.

In an embodiment, the non-hydrogen substituents that can be utilized as $R^{22}$, $R^{23}$, $R^{24}$, $R^{25}$, and $R^{26}$ in the R, $R^2$ or $R^3$ group having Structure III independently can be a halogen, a hydrocarbyl group, or a hydrocarboxy group; alternatively, a halogen or a hydrocarbyl group. In some embodiments, the non-hydrogen substituents that can be utilized as $R^{22}$, $R^{23}$, $R^{24}$, $R^{25}$, and $R^{26}$ in the R, $R^2$ or $R^3$ group having Structure III independently can be a halogen, an alkyl group, or an alkoxy group. Halogens, hydrocarbyl groups, hydrocarboxy groups, alkyl groups, and alkoxy groups that can be utilized as substituents are independently disclosed herein and can be utilized without limitation to further describe the R, $R^2$ and/or $R^3$ group having Structure III.

In an aspect, R, $R^2$ and $R^3$ can each independently be a benzyl group, a substituted benzyl group, a 1-phenyleth-1-yl group, a substituted 1-phenyleth-1-yl, a 2-phenyleth-1-yl group, or a substituted 2-phenyleth-1-yl group. In an embodiment, R, $R^2$ and $R^3$ can each independently be a benzyl group, or a substituted benzyl group; alternatively, a 1-phenyleth-1-yl group or a substituted 1-phenyleth-1-yl; alternatively, a 2-phenyleth-1-yl group or a substituted 2-phenyleth-1-yl group; or alternatively, a benzyl group, a 1-phenyleth-1-yl group, or a 2-phenyleth-1-yl group. In some embodiments, R, $R^2$ and $R^3$ can each independently be a benzyl group; alternatively, a substituted benzyl group; alternatively, a 1-phenyleth-1-yl group; alternatively, a substituted 1-phenyleth-1-yl; alternatively, a 2-phenyleth-1-yl group; or alternatively, a substituted 2-phenyleth-1-yl group.

In an embodiment, each substituent for a substituted benzyl group, a 1-phenyleth-1-yl group, or a 2-phenyleth-1-yl group (general or specific) that can be utilized as R, $R^2$ and/or $R^3$ can be a halogen, a hydrocarbyl group, or a hydrocarboxy group. In some embodiments, each substituent for a substituted benzyl group, 1-phenyleth-1-yl group, or a 2-phenyleth-1-yl group (general or specific) that can be utilized as R, $R^2$ and/or $R^3$ independently can be halogen, an alkyl group, or an alkoxy group. Halogens, hydrocarbyl groups, hydrocarboxy groups, alkyl groups, and alkoxy groups that can be utilized as substituents are independently disclosed herein and can be utilized without limitation to further describe the substituents for the substituted benzyl group, 1-phenyleth-1-yl group, or a 2-phenyleth-1-yl group (general or specific) that can be utilized as R, $R^2$ and/or $R^3$.

In an aspect, R, $R^2$ and $R^3$ can each independently be a pyridinyl group, a substituted pyridinyl group, a furyl group, a substituted furyl group, a thienyl group, or a substituted thienyl group.

In an embodiment, the pyridinyl (or substituted pyridinyl) R, $R^2$ and/or $R^3$ can be a pyridin-2-yl group, a substituted pyridin-2-yl group, a pyridin-3-yl group, a substituted pyridin-3-yl group, a pyridin-4-yl group, or a substituted pyridin-4-yl group; alternatively, a pyridin-2-yl group, a pyridin-3-yl group, or a pyridin-4-yl group. In some embodiments, the pyridinyl (or substituted pyridinyl) R, $R^2$ and/or $R^3$ group can be a pyridin-2-yl group or a substituted pyridin-2-yl group; alternatively, a pyridin-3-yl group or a substituted pyridin-3-yl group; alternatively, a pyridin-4-yl group or a substituted pyridin-4-yl group; alternatively, a pyridin-2-yl group; alternatively, a substituted pyridin-2-yl group; alternatively, a pyridin-3-yl group; alternatively, a substituted pyridin-3-yl group; alternatively, a pyridin-4-yl group; or alternatively, a substituted pyridin-4-yl group. In an embodiment, the substituted pyridinyl R, $R^2$ and/or $R^3$ group can be a 2-substituted pyridin-3-yl group, a 4-substituted pyridin-3-yl group, a 5-substituted pyridin-3-yl group, a 6-substituted pyridin-3-yl group, a 2,4-disubstituted pyridin-3-yl group, a 2,6-disubstituted pyridin-3-yl group, or a 2,4,6-trisubstituted pyridin-3-yl group; alternatively, a 2-substituted pyridin-3-yl group, a 4-substituted pyridin-3-yl group, or a 6-substituted pyridin-3-yl group; alternatively, a 2,4-disubstituted pyridin-3-yl group or a 2,6-disubstituted pyridin-3-yl group; alternatively, a 2-substituted pyridin-3-yl group; alternatively, a 4-substituted pyridin-3-yl group; alternatively, a 5-substituted pyridin-3-yl group; alternatively, a 6-substituted pyridin-3-yl group; alternatively, a 2,4-disubstituted pyridin-3-yl group; alternatively, a 2,6-disubstituted pyridin-3-yl group; or alternatively, a 2,4,6-trisubstituted pyridin-3-yl group.

In an embodiment, the furyl (or substituted furyl) R, $R^2$ and/or $R^3$ group can be a fur-2-yl group, a substituted fur-2-yl group, a fur-3-yl group, or a substituted fur-3-yl group. In an embodiment, the substituted furyl R, $R^2$ and/or $R^3$ group can be a 2-substituted fur-3-yl group, a 4-substituted fur-3-yl group, or a 2,4-disubstituted fur-3-yl group.

In an embodiment, the thienyl (or substituted thienyl) R, $R^2$ and/or $R^3$ group can be a thien-2-yl group, a substituted thien-2-yl group, a thien-3-yl group, or a substituted thien-3-yl group. In some embodiments, the thienyl (or substituted thienyl) R, $R^2$ and/or $R^3$ group can be a thien-2-yl group or a substituted thien-2-yl group. In an embodiment, the substituted thienyl R, $R^2$ and/or $R^3$ group can be a 2-substituted thien-3-yl group, a 4-substituted thien-3-yl group, or a 2,4-disubstituted thien-3-yl group.

In an embodiment, each substituent for a substituted pyridinyl, furyl, or thienyl groups (general or specific) that can be utilized as R, $R^2$ and/or $R^3$ can each independently be a halogen, a hydrocarbyl group, or a hydrocarboxy group. In some embodiments, each substituent for a substituted pyridinyl, furyl, and/or or thienyl group (general or specific) that can be utilized as R, $R^2$ and $R^3$ each independently can be a halogen, an alkyl group, or an alkoxy group; alternatively, a halogen or an alkyl group; alternatively, a halogen or an alkoxy group; alternatively, an alkyl group or an alkoxy group; alternatively, a halogen; alternatively, an alkyl group; or alternatively, an alkoxy group. Halogens, hydrocarbyl groups, hydrocarboxy groups, alkyl groups, and alkoxy groups that can be utilized as substituents are independently disclosed herein and can be utilized without limitation to further describe the substituents for the substituted pyridinyl, furyl, and/or thienyl groups (general or specific) that can be utilized as R, $R^2$ and/or $R^3$.

In a non-limiting embodiment, R, $R^2$ and/or $R^3$ can each independently be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group. In another non-limiting embodiment, R, $R^2$ and $R^3$ can each independently be a phenyl group, a 2-alkoxyphenyl group, a 3-alkoxyphenyl group, a 4-alkoxyphenyl group, or 3,5-dialkoxyphenyl group. In other non-limiting embodiments, R, $R^2$ and $R^3$ can each independently be a phenyl group, a 2-halophenyl group, a 3-halophenyl group, a 4-halophenyl group, a 2,6-dihalophenylgroup, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group;

alternatively, a 2,6-dihalophenyl group; or alternatively, a 3,5-dihalophenyl group. Halides, alkyl group substituents, and alkoxy group substituents are independently described herein and can be utilized, without limitation, to further describe the alkylphenyl, dialkylphenyl, trialkylphenyl, alkoxyphenyl, dialkoxyphenyl, halophenyl, or dihalophenyl groups that can be utilized for R, $R^2$ and/or $R^3$. Generally, the halides, alkyl substituents, or alkoxy substituents of a dialkyl, trialkyl phenyl, dialkoxyphenyl, or dihalophenyl groups can be the same; or alternatively, the halo, alkyl substituents, or alkoxy substituents of alkylphenyl, dialkylphenyl, trialkylphenyl, dialkoxyphenyl, or dihalophenyl groups can be different.

In a non-limiting embodiment, R, $R^2$ and $R^3$ can each independently be a 2-methylphenyl group, a 2-ethylphenyl group, a 2-isopropylphenyl group, a 2-tert-butylphenyl group, a 4-methylphenyl group, a 4-ethylphenyl group, a 4-isopropylphenyl group, or a 4-tert-butylphenyl group; alternatively, a 2-methylphenyl group, a 2-ethylphenyl group, a 2-isopropylphenyl group, or a 2-tert-butylphenyl group; alternatively, a 4-methylphenyl group, a 4-ethylphenyl group, a 4-isopropylphenyl group, or a 4-tert-butylphenyl group; alternatively, a 2-methylphenyl group; alternatively, a 2-ethylphenyl group; alternatively, a 2-isopropylphenyl group; alternatively, a 2-tert-butylphenyl group; alternatively, a 4-methylphenyl group; alternatively, a 4-ethylphenyl group; alternatively, a 4-isopropylphenyl group; or alternatively, a 4-tert-butylphenyl group. In another non-limiting embodiment, R, $R^2$ and $R^3$ can each independently be a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; alternatively, a 4-methoxyphenyl group, a 4-ethoxyphenyl group, a 4-isopropoxyphenyl group, or a 4-tert-butoxyphenyl group; alternatively, a 2-methoxyphenyl group; alternatively, a 2-ethoxyphenyl group; alternatively, a 2-isopropoxyphenyl group; alternatively, a 2-tert-butoxyphenyl group; alternatively, a 4-methoxyphenyl group; alternatively, a 4-ethoxyphenyl group; alternatively, a 4-isopropoxyphenyl group; or alternatively, a 4-tert-butoxyphenyl group. In other non-limiting embodiments, R, $R^2$ and $R^3$ can each independently be a 2-fluorophenyl group, a 2-chlorophenyl group, a 3-fluorophenyl group, a 3-chlorophenyl group, a 4-fluorophenyl group, a 4-chlorophenyl group, a 3,5-difluorophenyl group, or a 3,5-dichlorophenyl group; alternatively, a 2-fluorophenyl group or a 2-chlorophenyl group; alternatively, a 3-fluorophenyl group or a 3-chlorophenyl group; alternatively, a 4-fluorophenyl group or a 4-chlorophenyl group; alternatively, a 3,5-difluorophenyl group or a 3,5-dichlorophenyl group; alternatively, a 3-fluorophenyl group, a 3-chlorophenyl group, a 3,5-difluorophenyl group or a 3,5-dichlorophenyl group; alternatively, a 3-fluorophenyl group or a 3,5-difluorophenyl group; alternatively, a 2-fluorophenyl group; alternatively, a 2-chlorophenyl group; alternatively, a 3-fluorophenyl group; alternatively, a 3-chlorophenyl group; alternatively, a 4-fluorophenyl group; alternatively, a 4-chlorophenyl; alternatively, a 3,5-difluorophenyl group; or alternatively, a 3,5-dichlorophenyl group.

In an embodiment, Q is a donor group which can have Structure (IIQ), (IIIQ) or (IVQ):

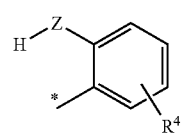

Structure IIQ

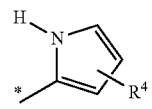

Structure IIIQ

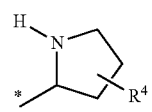

Structure IVQ where N represents nitrogen, Z can be oxygen or sulfur and $R^4$ can be hydrogen, a halogen, a hydrocarbyl group, or a substituted hydrocarbyl group and wherein the undesignated valency (*) represents the point at which the donor group attaches to the imine phenol compound of Structure I. Generally $R^4$ can be any of the halogens, hydrocarbyl groups, or substituted hydrocarbyl groups described herein (e.g., in the description of groups suitable for use as $R^2$ and/or $R^3$).

In an embodiment, the catalyst composition comprises a metal salt complex, alternatively a metal-salt complex of an imine bis(phenol) compound, alternatively a metal salt complex of an imine bis(phenol) compound which can have Structure V.

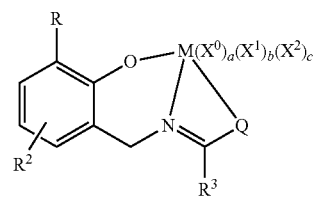

Structure V

In Structure V, O and N represent oxygen and nitrogen respectively; Q represents a donor group which can have Structure (VI), (VII) or (VIII) and wherein the undesignated valency (*) represents the point at which the donor group attaches to the imine phenol compound of Structure V,

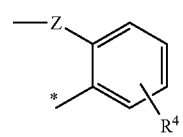

Structure VI

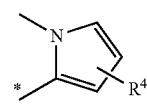

Structure VII

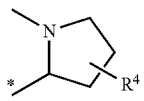

Structure VIII and M is a Group 3 to Group 12 transition metal or lanthanide. Referring to Structure V, $X^0$ can be a neutral ligand and a have a value of 0, 1, or 2; $X^1$ can be a monoanionic ligand, and b have a value of 0, 1, 2, 3, or 4; and $X^2$ can be a dianionic ligand, and c have a value of 0, 1, or 2.

In an embodiment, R, $R^2$, $R^3$, $R^4$, and Q of Structure V corresponds to R, $R^2$, $R^3$, $R^4$, and Q of Structure I respectively such that the groups, features and aspects utilized to describe $R^2$, $R^3$, $R^4$, and Q of Structure I may be used to describe the corresponding R, $R^2$, $R^3$, $R^4$, and Q of Structure V. One or more of R, $R^2$, $R^3$, and $R^4$ may each be the same or different.

Generally the metal atom of the metal salt complex of the imine bis(phenol) compound (e.g., M in Structure V) can be any metal atom. In an aspect, the metal atom can be a transition metal or a lanthanide. In an embodiment, suitable metal salts can comprise, or consist essentially of, a Group 3-12 transition metal; alternatively, a Group 4-10 transition metal; alternatively, a Group 6-9 transition metal; alternatively, a Group 7-8 transition metal; alternatively, a Group 4 transition metal; alternatively, a Group 5 transition metal alternatively, a Group 6 transition metal; alternatively, a Group 7 transition metal; alternatively, a Group 8 transition metal; alternatively, a Group 9 transition metal; or alternatively, a Group 10 transition metal. In some embodiments, the metal salt can comprise titanium, zirconium, hafnium, vanadium, niobium, tantalum, chromium, molybdenum, tungsten, manganese, iron, cobalt, nickel, palladium, platinum, copper, or zinc. Alternatively M is a Group 4 transition metal. Alternatively, M is titanium. Alternatively, M is zirconium. Alternatively, M is hafnium.

Generally, the metal atom of the metal can have any positive oxidation state available to the metal atom. In an embodiment, the oxidation state of M is equal to (b+2c+2). In an embodiment, the metal can have an oxidation state of from +2 to +6; alternatively, from +2 to +4; or alternatively, from +2 to +3. In some embodiments, the metal can have an oxidation state of +1; alternatively, +2; alternatively, +3; or alternatively, +4. For example, the most common oxidation state for Ti, Zr, and Hf can be +4; therefore, c can be equal to zero and b can be equal to 2 (two monoanionic ligands), or b can be equal to zero and c can be equal to 1 (one dianionic ligand). The most common oxidation state for V and Ta can be +5; therefore, for instance, b can be equal to one (one monoanionic ligand) and c can be equal to 1 (one dianionic ligand).

Referring to Structure V, $X^0$ can be a neutral ligand, and the integer a in Structure V can be 0, 1 or 2. In an aspect, suitable neutral ligands can include sigma-donor solvents that contain an atom (or atoms) that can coordinate to the metal atom in Structure V. Examples of suitable coordinating atoms include, but are not limited to, O, N, S, and P, or combinations of these atoms. The neutral ligand can be unsubstituted or can be substituted. Substituent groups are independently described herein and can be utilized, without limitation to further describe a neutral ligand which can be utilized as $X^0$ in Structure V. In some aspects, the neutral ligand can be a Lewis base. When the integer a is equal to 2, it is contemplated that the two neutral ligands can be the same or different and the descriptions set forth herein apply to each ligand independently.

In an aspect, $X^0$, can be an ether, a thioether, an amine, a nitrile, or a phosphine. In another aspect, $X^0$, can be an acyclic ether, a cyclic ether, an acyclic thioether, a cyclic thioether, a nitrile, an acyclic amine, a cyclic amine, an acyclic phosphine, a cyclic phosphine, or combinations thereof. In other aspects, $X^0$, can be an acyclic ether or a cyclic ether; alternatively, an acyclic thioether or a cyclic thioether; alternatively, an acyclic amine or a cyclic amine; alternatively, an acyclic phosphine or a cyclic phosphine; alternatively, an acyclic ether; alternatively, a cyclic ether; alternatively, an acyclic thioether; alternatively, a cyclic thioether; alternatively, a nitrile; alternatively, an acyclic amine; alternatively, a cyclic amine; alternatively, an acyclic phosphine; or alternatively, a cyclic phosphine. Further, $X^0$ can include any substituted analogs of any acyclic ether, cyclic ether, acyclic thioether, cyclic thioether, nitrile, acyclic amine, cyclic amine, acyclic phosphine, or cyclic phosphine, as disclosed herein.

In an aspect, $X^0$ can be a nitrile having the formula $R^{1q}C\equiv N$, an ether having the formula $R^{2q}-O-R^{3q}$, a thioether having the formula $R^{4q}-S-R^{5q}$, an amine having the formula $NR^{6q}R^{7q}R_{8q}$, $NHR^{6q}R^{7q}$, or $NH_2R^{6q}$, or a phosphine having the formula $PR^{9q}R^{10q}R^{11}$, $PHR^{9q}R^{10q}$, or $PH_2R^{9q}$; alternatively, a nitrile having the formula $R^{1q}C\equiv N$, an ether having the formula $R^{2q}-O-R^{3q}$, a thioether having the formula $R^{4q}-S-R^{5q}$, an amine having the formula $NR^{6q}R^{7q}R^{8q}$, or a phosphine having the formula $PR^{9q}R^{10q}R^{11q}$; or alternatively, a nitrile having the formula $R^{1q}C\equiv N$, an ether having the formula $R^{2q}-O-R^{3q}$, a thioether having the formula $R^{4q}-S-R^{5q}$, an amine having the formula $NR^{6q}R^{7q}R^{8q}$, or a phosphine having the formula $PR^{9q}R^{10q}R^{11q}$. In an aspect, $X^0$ can be a nitrile having the formula $R^{1q}C\equiv N$; alternatively, an ether having the formula $R^{2q}-O-R^{3q}$; alternatively, a thioether having the formula $R^{4a}-S-R^{5a}$; alternatively, an amine having the formula $NR^{6q}R^{7q}R^{8q}$, $NHR^{6q}R^{7q}$, or $NH_2R^{6q}$; alternatively, a phosphine having the formula $PR^{9q}R^{10q}R^{11q}$, $PHR^{9q}R^{10q}$, or $PH_2R^{9q}$; or alternatively, a phosphine having the formula $PR^{9q}R^{10q}R^{11q}$.

In an aspect, $R^{1q}$ of the nitrile having the formula $R^{1q}C\equiv N$, $R^{2q}$ and $R^{3q}$ of the ether having formula $R^{2q}-O-R^{3q}$, $R^{4q}$ and $R^{5q}$ of the thioether having the formula $R^{4q}-SR^{5q}$, $R^{6q}$, $R^{7q}$, and $R^{8q}$ of the amine having the formula $NR^{6q}R^{7q}R^{8q}$, $NHR^{6q}R^{7q}$, or $NH_2R^{6q}$, and $R^{9q}$, $R^{10q}$, and $R^{11q}$ of the phosphine having the formula $PR^{9q}R^{10q}R^{11q}$, $PHR^{9q}R^{10q}$, or $PH_2R^{9q}$, independently can be a $C_1$ to $C_{18}$ hydrocarbyl group; alternatively, a $C_1$ to $C_{15}$ hydrocarbyl group; alternatively, a $C_1$ to $C_{12}$ hydrocarbyl group; alternatively, a $C_1$ to $C_8$ hydrocarbyl group; or alternatively, a $C_1$ to $C_6$ hydrocarbyl group. It should also be noted that $R^{2q}$ and $R^{3q}$ of the ether having formula $R^{2q}-O-R^{3q}$, $R^{4q}$ and $R^{5q}$ of the thioether having the formula $R^{4q}-S-R^{5q}$, any two of $R^{6q}$, $R^{7q}$, and $R^{8q}$ of the amine having the formula $NR^{6q}R^{7q}R^{8q}$ or $NHR^{6q}R^{7q}$, and/or any two of $R^{9q}$, $R^{10q}$, and $R^{11q}$ of the phosphine having the formula $PR^{9q}R^{10q}R^{11q}$ or $PHR^{9q}R^{10q}$ can be joined to form a ring containing the ether oxygen atom, the thioether sulfur atom, the amine nitrogen atom, or the phosphine phosphorus atom to form a cyclic ether, thioether, amine, or phosphine, respectively, as described herein in regards to cyclic ethers, thioethers, amines, and phosphines.

In an aspect, $R^{1q}$ of the nitrile having the formula $R^{1q}C\equiv N$, $R^{2q}$ and $R^{3q}$ of the ether having formula $R_{2q}-O-R^{3q}$, $R^{4q}$ and $R^{5q}$ of the thioether having the formula $R^{4q}-S-R^{5q}$, $R^{6q}$, $R^{7q}$, and $R^{8q}$ of the amine having the formula $NR^{6q}R^{7q}R^{8q}$, $NHR^{6q}R^{7q}$, or $NH_2R^{6q}$, and $R^{9q}$, $R^{10q}$, and $R^{11q}$ of the phosphine having the formula $PR^{9g}R^{10q}R^{11q}$, $PHR^{9q}R^{10q}$, or $PH_2R^{9q}$, independently be any hydrocarbyl group disclosed herein. The hydrocarbyl group can be, for instance, any alkyl group, cycloalkyl group, aryl group, or aralkyl group disclosed herein.

In another aspect $X^0$, in Structure V independently can be a $C_2$-$C_{30}$ ether, a $C_2$-$C_{30}$ thioether, a $C_2$-$C_{20}$ nitrile, a $C_1$-$C_{30}$ amine, or a $C_1$-$C_{30}$ phosphine; alternatively, a $C_2$-$C_{18}$ ether; alternatively, a $C_2$-$C_{18}$ thioether; alternatively, a $C_2$-$C_{12}$ nitrile; alternatively, a $C_1$-$C_{18}$ amine; or alternatively, a $C_1$-$C_{18}$ phosphine. In some aspects, each neutral ligand independently can be a $C_2$-$C_{12}$ ether, a $C_2$-$C_{12}$ thioether, a $C_2$-$C_8$ nitrile, a $C_1$-$C_{12}$ amine, or a $C_1$-$C_{12}$ phosphine; alternatively, a $C_2$-$C_{10}$ ether; alternatively, a $C_2$-$C_{10}$ thioether; alternatively, a $C_2$-$C_6$ nitrile; alternatively, a $C_1$-$C_8$ amine; or alternatively, a $C_1$-$C_8$ phosphine.

Suitable ethers which can be utilized as $X^0$, either alone or in combination, can include, but are not limited to, dimethyl ether, diethyl ether, dipropyl ether, dibutyl ether, methyl ethyl ether, methyl propyl ether, methyl butyl ether, diphenyl ether, ditolyl ether, tetrahydrofuran, 2-methyltetrahydrofuran, 2,5-dimethyltetrahydrofuran, 2,3-dihydrofuran, 2,5-dihydrofuran, furan, benzofuran, isobenzofuran, dibenzofuran, tetrahydropyran, 3,4-dihydro-2H-pyran, 3,6-dihydro-2H-pyran, 2H-pyran, 4H-pyran, 1,3-dioxane, 1,4-dioxane, morpholine, and the like, including substituted derivatives thereof.

Suitable thioethers which can be utilized as $X^0$, either alone or in combination, can include, but are not limited to, dimethyl thioether, diethyl thioether, dipropyl thioether, dibutyl thioether, methyl ethyl thioether, methyl propyl thioether, methyl butyl thioether, diphenyl thioether, ditolyl thioether, thiophene, benzothiophene, tetrahydrothiophene, thiane, and the like, including substituted derivatives thereof.

Suitable nitriles which can be utilized as $X^0$, either alone or in combination, can include, but are not limited to, acetonitrile, propionitrile, butyronitrile, benzonitrile, 4-methylbenzonitrile, and the like, including substituted derivatives thereof.

Suitable amines which can be utilized as $X^0$, either alone or in combination, can include, but are not limited to, methyl amine, ethyl amine, propyl amine, butyl amine, dimethyl amine, diethyl amine, dipropyl amine, dibutyl amine, trimethyl amine, triethyl amine, tripropyl amine, tributyl amine, aniline, diphenylamine, triphenylamine, tolylamine, xylylamine, ditolylamine, pyridine, quinoline, pyrrole, indole, 2-methylpyridine, 3-methylpyridine, 4-methylpyridine, 2,5-dimethylpyrrole, 2,5-diethylpyrrole, 2,5-dipropylpyrrole, 2,5-dibutylpyrrole, 2,4-dimethylpyrrole, 2,4-diethylpyrrole, 2,4-dipropylpyrrole, 2,4-dibutylpyrrole, 3,4-dimethylpyrrole, 3,4-diethylpyrrole, 3,4-dipropylpyrrole, 3,4-dibutylpyrrole, 2-methylpyrrole, 2-ethylpyrrole, 2-propylpyrrole, 2-butylpyrrole, 3-methylpyrrole, 3-ethylpyrrole, 3-propylpyrrole, 3-butylpyrrole, 3-ethyl-2,4-dimethylpyrrole, 2,3,4,5-tetramethylpyrrole, 2,3,4,5-tetraethylpyrrole, and the like, including substituted derivatives thereof. Suitable amines can be primary amines, secondary amines, or tertiary amines.

Suitable phosphines which can be utilized as $X^0$, either alone or in combination, can include, but are not limited to, trimethylphosphine, triethylphosphine, tripropylphosphine, tributylphosphine, phenylphosphine, tolylphosphine, diphenylphosphine, ditolylphosphine, triphenylphosphine, tritolylphosphine, methyldiphenylphosphine, dimethylphenylphosphine, ethyldiphenylphosphine, diethylphenylphosphine, and the like, including substituted derivatives thereof.

In an aspect, $X^0$ can be azetidine, oxetane, thietane, dioxetane, dithietane, tetrahydropyrrole, dihydropyrrole, pyrrole, indole, isoindole, tetrahydrofuran, 2-methyltetrahydrofuran, 2,5-dimethyltetrahydrofuran, dihydrofuran, furan, benzofuran, isobenzofuran, tetrahydrothiophene, dihydrothiophene, thiophene, benzothiophene, isobenzothiophene, imidazolidine, pyrazole, imidazole, oxazolidine, oxazole, isoxazole, thiazolidine, thiazole, isothiazole, benzothiazole, dioxolane, dithiolane, triazole, dithiazole, piperidine, pyridine, dimethyl amine, diethyl amine, tetrahydropyran, dihydropyran, pyran, thiane, piperazine, diazine, oxazine, thiazine, dithiane, dioxane, dioxin, triazine, triazinane, trioxane, oxepin, azepine, thiepin, diazepine, morpholine, quinoline, tetrahydroquinone, bicyclo[3.3.1]tetrasiloxane, or acetonitrile; alternatively, azetidine, oxetane, thietane, dioxetane, dithietane, tetrahydropyrrole, tetrahydrofuran, 2-methyltetrahydrofuran, 2,5-dimethyltetrahydrofuran, tetrahydrothiophene, imidazolidine, oxazolidine, oxazole, thiazolidine, thiazole, dioxolane, dithiolane, piperidine, tetrahydropyran, pyran, thiane, piperazine, oxazine, thiazine, dithiane, dioxane, dioxin, triazinane, trioxane, azepine, thiepin, diazepine, morpholine, 1,2-thiazole, or bicyclo[3.3.1]tetrasiloxane; alternatively, tetrahydropyrrole, tetrahydrofuran, 2-methyltetrahydrofuran, 2,5-dimethyltetrahydrofuran, tetrahydrothiophene, oxazolidine, thiazolidine, dioxolane, dithiolane, dithiazole, piperidine, tetrahydropyran, pyran, thiane, piperazine, dithiane, dioxane, dioxin, trioxane, or morpholine; alternatively, tetrahydrofuran, 2-methyltetrahydrofuran, 2,5-dimethyltetrahydrofuran, tetrahydrothiophene, dioxolane, dithiolane, tetrahydropyran, pyran, thiane, dithiane, dioxane, dioxin, or trioxane; alternatively, tetrahydrofuran, dioxolane, tetrahydropyran, dioxane, or trioxane; alternatively, pyrrole, furan, pyrazole, imidazole, oxazole, isoxazole, thiazole, isothiazole, triazole, pyridine, dimethyl amine, diethyl amine, diazine, triazine, or quinoline; alternatively, pyrrole, furan, imidazole, oxazole, thiazole, triazole, pyridine, dimethyl amine, diethyl amine, diazine, or triazine; or alternatively, furan, oxazole, thiazole, triazole, pyridine, diazine, or triazine. In some aspects, $X^0$ can be azetidine; alternatively, oxetane; alternatively, thietane; alternatively, dioxetane; alternatively, dithietane; alternatively, tetrahydropyrrole; alternatively, dihydropyrrole, alternatively, pyrrole; alternatively, indole; alternatively, isoindole; alternatively, tetrahydrofuran; alternatively, 2-methyltetrahydrofuran; alternatively, 2,5-dimethyltetrahydrofuran; alternatively, dihydropyrrole; alternatively, furan; alternatively, benzofuran; alternatively, isobenzofuran; alternatively, tetrahydrothiophene; alternatively, dihydrothiophene; alternatively, thiophene; alternatively, benzothiophene; alternatively, isobenzothiophene; alternatively, imidazolidine; alternatively, pyrazole; alternatively, imidazole; alternatively, oxazolidine; alternatively, oxazole; alternatively, isoxazole; alternatively, thiazolidine; alternatively, thiazole; alternatively, benzothiazole; alternatively, isothiazole; alternatively, dioxolane; alternatively, dithiolane; alternatively, triazole; alternatively, dithiazole; alternatively, piperidine; alternatively, pyridine; alternatively, dimethyl amine; alternatively, diethyl amine; alternatively, tetrahydropyran; alternatively, dihydropyran; alternatively, pyran; alternatively, thiane; alternatively, piperazine; alternatively, diazine; alternatively, oxazine; alternatively, thiazine; alternatively, dithiane; alternatively, dioxane; alternatively, dioxin; alternatively, triazine; alternatively, triazinane; alternatively, trioxane; alternatively, oxepin; alternatively, azepine; alternatively, thiepin; alternatively, diazepine; alternatively, morpholine; alternatively, quinoline; alternatively, tetrahydroquinone; alternatively, bicyclo[3.3.1]tetrasiloxane; or alternatively, acetonitrile. In another aspect, $X^0$ can be azetidine, tetrahydropyrrole, dihydropyrrole, pyrrole, indole, isoindole, imidazolidine, pyrazole, imidazole, oxazolidine, oxazole, isoxazole, thiazolidine, thiazole, isothiazole, triazole, benzotriazole, dithiazole, piperidine, pyridine, dimethyl amine, diethyl amine, piperazine, diazine, oxazine, thiazine, triazine, azepine, diazepine, morpholine, quinoline, or tetrahydroisoquinoline. In another aspect, $X^0$ can be thietane, dithietane, tetrahydrothiophene, dihydrothiophene, thiophene, benzothiophene, isobenzothiophene, thiazolidine, thiazole, isothiazole, dithiolane, dithiazole, thiane, thiazine, dithiane, or thiepin. In another aspect, $X^0$ can be tetrahydrofuran, furan, methyltetrahydrofuran, dihydrofuran, tetrahydropyran, 2,3-dihydropyran, 1,3-dioxane, 1,4-dioxane, morpholine, N-methylmorpholine, acetonitrile, propionitrile, butyronitrile, benzonitrile, pyridine, ammonia, methyl amine, ethyl amine, dimethyl amine, diethyl amine, trimethyl amine, triethyl amine, trimethylphosphine, triethylphosphine, triphenylphosphine, tri-n-butylphosphine, methyl isocyanide, n-butyl isocyanide, phenyl isocyanide, $SMe_2$, thiophene, or tetrahydrothiophene. In another aspect, $X^0$ can be tetrahydrofuran, methyltetrahydrofuran, tetrahydropyran, 1,4-dioxane, acetonitrile, pyridine, dimethyl amine, diethyl amine, ammonia, trimethyl amine, triethyl amine, trimethylphosphine, triethylphosphine, triphenylphosphine, $SMe_2$, or tetrahydrothiophene; alternatively, tetrahydrofuran, methyltetrahydrofuran, tetrahydropyran, or 1,4-dioxane; alternatively, ammonia, trimethylamine, or triethylamine; or alternatively, trimethylphosphine, triethylphosphine, or triphenylphosphine. Yet, in another aspect, $X^0$ can be tetrahydrofuran, acetonitrile, pyridine, ammonia, dimethyl amine, diethyl amine, trimethyl amine, trimethylphosphine, or triphenylphosphine; alternatively, tetrahydrofuran, acetonitrile, pyridine, dimethyl amine, diethyl amine, trimethyl amine, trimethylphosphine, or triphenylphosphine; alternatively, tetrahydrofuran, acetonitrile, dimethyl amine, diethyl amine, or pyridine; alternatively, tetrahydrofuran; alternatively, acetonitrile; alternatively, dimethyl amine; alternatively, diethyl amine; or alternatively, pyridine.

$X^1$ in Structure V can be a monoanionic ligand, and the integer b in Structure V can be 0, 1, 2, 3, or 4. $X^1$ can be a hydrogen (hydride), a halide, a $C_1$ to $C_{18}$ hydrocarbyl group, a hydrocarbyloxide group, a hydrocarbylamino group, a hydrocarbylsilyl group, or a hydrocarbylaminosilyl group. If b is greater than 1, each $X^1$ group of Structure V, can be the same or a different. In an embodiment b is greater than 1 and each $X^1$ can independently be a hydrogen (hydride), a halide, a $C_1$ to $C_{18}$ hydrocarbyl group, a hydrocarbyloxide group, a hydrocarbylamino group, a hydrocarbylsilyl group, or a hydrocarbylaminosilyl group In one aspect, $X^1$ can be hydrogen, a halide (e.g., F, Cl, Br, or I), a $C_1$ to $C_{18}$ hydrocarbyl group, a hydrocarbyloxide group, a hydrocarbylamino group, a hydrocarbylsilyl group, or a hydrocarbylaminosilyl group. In another aspect, $X^1$ can be hydrogen, a halide, a $C_1$ to $C_{12}$ hydrocarbyl group, a hydrocarbyloxide group, a hydrocarbylamino group, a hydrocarbylsilyl group, or a hydrocarbylaminosilyl group. In yet another aspect, $X^1$ can be hydrogen, a halide, a $C_1$ to $C_{10}$ hydrocarbyl group, a hydrocarbyloxide group, a hydrocarbylamino group, a hydrocarbylsilyl group, or a hydrocarbylaminosilyl group. In still another aspect, $X^1$ can be hydrogen, a halide, a $C_1$ to $C_8$ hydrocarbyl group, a hydrocarbyloxide group, a hydrocarbylamino group, a hydrocarbylsilyl group, or a hydrocarbylaminosilyl group.

The hydrocarbyl group which can be $X^1$ in Structure V can be any $C_1$ to $C_{18}$ hydrocarbyl group, any $C_1$ to $C_{12}$ hydrocarbyl group, any $C_1$ to $C_{10}$ hydrocarbyl group, or any $C_1$ to $C_8$ hydrocarbyl group disclosed herein. A hydrocarbyloxide group is used generically herein to include, for instance, alkoxy, aryloxy, and -(alkyl or aryl)-O-(alkyl or aryl) groups, and these groups can comprise up to about 18 carbon atoms (e.g., $C_1$ to $C_{18}$, $C_1$ to $C_{12}$, $C_1$ to $C_{10}$, or $C_1$ to $C_8$ hydrocarbyloxide groups). Illustrative and non-limiting examples of hydrocarbyloxide groups can include methoxy, ethoxy, propoxy, butoxy, phenoxy, substituted phenoxy, acetylacetonate (acac), and the like. The term hydrocarbylamino group is used generically herein to refer collectively to, for instance, alkylamino, arylamino, dialkylamino, diarylamino, and -(alkyl or aryl)-N-(alkyl or aryl) groups, and the like. Unless otherwise specified, the hydrocarbylamino groups which can be $X^1$ in Structure V can comprise up to about 18 carbon atoms (e.g., $C_1$ to $C_{18}$, $C_1$ to $C_{12}$, $C_1$ to $C_{10}$, or $C_1$ to $C_8$ hydrocarbylamino groups). The hydrocarbylsilyl group which can be $X^1$ in Structure V can be any $C_1$ to $C_{18}$ hydrocarbylsilyl group, any $C_1$ to $C_{12}$ hydrocarbylsilyl group, any $C_1$ to $C_{10}$ hydrocarbylsilyl group, or any $C_1$ to $C_8$ hydrocarbylsilyl group, disclosed herein. A hydrocarbylaminosilyl group is used herein to refer to groups containing at least one hydrocarbon moiety, at least one nitrogen atom, and at least one silicon atom. Illustrative and non-limiting examples of hydrocarbylaminosilyl groups which can be $X^1$ can include, but are not limited to —$N(SiMe_3)_2$, —$N(SiEt_3)_2$, and the like. Unless otherwise specified, the hydrocarbylaminosilyl groups which can be $X^1$ can comprise up to about 18 carbon atoms (e.g., $C_1$ to $C_{18}$, $C_1$ to $C_{12}$, $C_1$ to $C_{10}$, or $C_1$ to $C_8$ hydrocarbylaminosilyl groups).

In accordance with an aspect of this disclosure, $X^1$ in Structure V can be a halide; alternatively, a $C_1$ to $C_{18}$ hydrocarbyl group; alternatively, a $C_1$ to $C_{18}$ hydrocarbyloxide group; alternatively, a $C_1$ to $C_{18}$ hydrocarbylamino group; alternatively, a $C_1$ to $C_{18}$ hydrocarbylsilyl group; or alternatively, a $C_1$ to $C_{18}$ hydrocarbylaminosilyl group. In accordance with another aspect, $X^1$ can be hydrogen; alternatively, F; alternatively, Cl; alternatively, Br; alternatively, I; alternatively, a $C_1$ to $C_{18}$ hydrocarbyl group; alternatively, a $C_1$ to $C_{18}$ hydrocarbyloxide group; alternatively, a $C_1$ to $C_{18}$ hydrocarbylamino group; alternatively, a $C_1$ to $C_{18}$ hydrocarbylsilyl group; or alternatively, a $C_1$ to $C_{18}$ hydrocarbylaminosilyl group. In accordance with yet another aspect, or at least one $X^1$ can be hydrogen, a halide, methyl, phenyl, benzyl, an alkoxy, an aryloxy, acetylacetonate, an alkylamino, a dialkylamino, a trihydrocarbylsilyl, or a hydrocarbylaminosilyl; alternatively, hydrogen, a halide, methyl, phenyl, or benzyl; alternatively, an alkoxy, an aryloxy, or acetylacetonate; alternatively, an alkylamino or a dialkylamino; alternatively, a trihydrocarbylsilyl or hydrocarbylaminosilyl; alternatively, hydrogen or a halide; alternatively, methyl, phenyl, benzyl, an alkoxy, an aryloxy, acetylacetonate, an alkylamino, or a dialkylamino; alternatively, hydrogen; alternatively, a halide; alternatively, methyl; alternatively, phenyl; alternatively, benzyl; alternatively, an alkoxy; alternatively, an aryloxy; alternatively, acetylacetonate; alternatively, an alkylamino; alternatively, a dialkylamino; alternatively, a trihydrocarbylsilyl; or alternatively, a hydrocarbylaminosilyl. In these and other aspects, the alkoxy, aryloxy, alkylamino, dialkylamino, trihydrocarbylsilyl, and hydrocarbylaminosilyl can be a $C_1$ to $C_{18}$, a $C_1$ to $C_{12}$, a $C_1$ to $C_{10}$, or a $C_1$ to $C_8$ alkoxy, aryloxy, alkylamino, dialkylamino, trihydrocarbylsilyl, or hydrocarbylaminosilyl.

$X^2$ in Structure V can be a dianionic ligand, and the integer c in Structure V can be either 0, 1, or 2. In one aspect, $X^2$ can be =O, =$NR^{2A}$, or =$CR^{2B}R^{2C}$. In another aspect, $X^2$ can be =O; alternatively, $X^2$ can be =$NR^{2A}$; or alternatively, $X^2$ can be =$CR^{2B}R^{2C}$. Independently, $R^{2A}$, $R^{2B}$, and $R^{2C}$ can be hydrogen or any $C_1$ to $C_{18}$ hydrocarbyl group disclosed herein; alternatively, hydrogen or any $C_1$ to $C_{12}$ hydrocarbyl group disclosed herein; alternatively, hydrogen or any $C_1$ to $C_{10}$ hydrocarbyl group disclosed herein; or alternatively, hydrogen or any $C_1$ to $C_8$ hydrocarbyl group disclosed herein. As an example, $R^{2A}$, $R^{2B}$, and $R^{2C}$ can each independently be hydrogen or any $C_1$ to $C_{12}$, $C_1$ to $C_8$, or any $C_1$ to $C_6$ alkyl group disclosed herein.

In an embodiment an imine (bis)phenol compound suitable for use in the present disclosure comprises a compound having Structure IX:

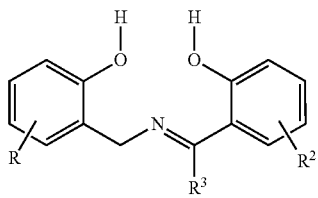

Structure IX where the groups utilized to describe R, $R^2$, and $R^3$ of Structure I may be utilized to describe R, $R^2$, and $R^3$ respectively of Structure IX.

In an embodiment, an imine bis(phenol) compound suitable for use in the present disclosure comprises a compound having Structure X:

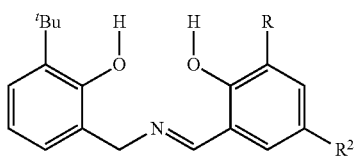

Structure X where the groups utilized to describe R and $R^2$ of Structure I may be utilized to describe R and $R^2$ respectively of Structure X. In an embodiment of Structure X, R is a t-butyl group and $R^2$ is hydrogen. Alternatively R and $R^2$ are t-butyl groups, alternatively R is a methyl group and $R^2$ is hydrogen, alternatively R and $R^2$ are chloride, alternatively R is adamantyl and $R^2$ is methyl, alternatively R is methoxy and $R^2$ is hydrogen, or alternatively R and $R^2$ are hydrogen.

In an embodiment an imine phenol compound suitable for use in the present disclosure comprises a compound having Structure XI:

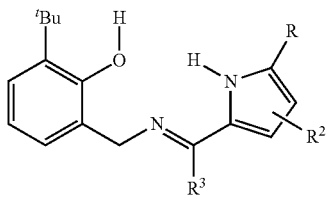

Structure XI where the groups utilized to describe R, $R^2$, and $R^3$ of Structure I may be utilized to describe R, $R^2$, and $R^3$ respectively of Structure XI.

In an embodiment, an imine phenol compound suitable for use in the present disclosure comprises a compound having Structure XII:

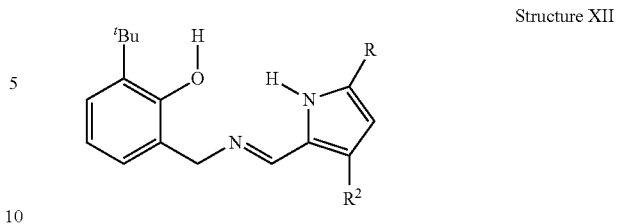

Structure XII where the groups utilized to describe R and $R^2$ of Structure I may be utilized to describe R and $R^2$ respectively of Structure XII. In an embodiment of Structure XII, R and $R^2$ are methyl groups, or alternatively R and $R^2$ are hydrogen.

In an embodiment, a metal salt complex of an imine (bis) phenol compound suitable for use in the present disclosure comprises a compound having Structure XIII:

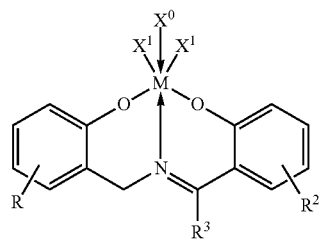

Structure XIII where M is titanium, zirconium, or hafnium and R, $R^2$, $R^3$, $X^0$, and $X^1$ are of the type described herein. In an embodiment of Structure XIII, M is zirconium and R is a t-butyl group. Alternatively, M is hafnium and R is a t-butyl group; alternatively, M is zirconium and R and $R^2$ are t-butyl groups, alternatively M is zirconium and R is a methyl group, alternatively M is zirconium and R and $R^2$ are chloride, or alternatively M is zirconium, R is adamantyl and $R^2$ is methyl.

In an embodiment, a metal salt complex of an imine bis (phenol) compound suitable for use in the present disclosure comprises a compound having Structure XIV where $OEt_2$ represents ethoxide:

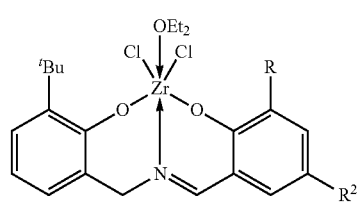

Structure XIV where the groups utilized to describe R and $R^2$ of Structure I may be utilized to describe R and $R^2$ respectively of Structure XIV.

In an embodiment, a metal salt complex of an imine bis (phenol) compound suitable for use in the present disclosure comprises a compound having Structure XV where OEt represents ethoxy:

Structure XV

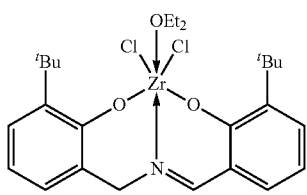

In an embodiment, a metal salt complex of an imine bis(phenol) compound suitable for use in the present disclosure comprises a compound having any of Structures XVI, XVII, XVIII, XIX, XX, or XXI where $X^1$ is of the type disclosed herein:

Structure XVI

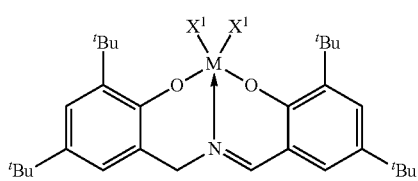

Structure XVII

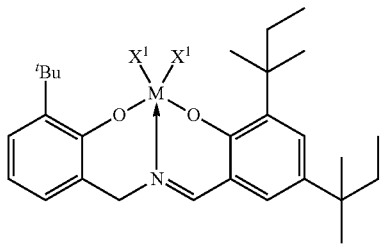

Structure XVIII

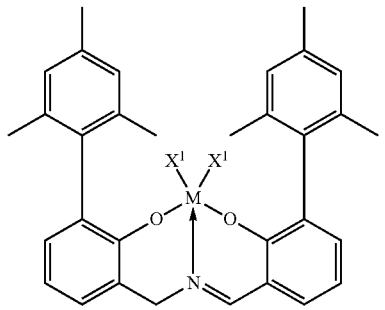

Structure XIX

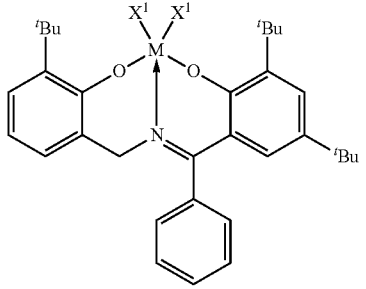

Structure XX

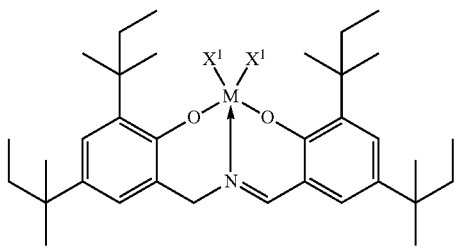

Structure XXI

In an embodiment, the catalyst composition further comprises a chemically-treated solid oxide which may function as an activator-support. Alternatively, the chemically-treated solid oxide can comprise a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, or any combination thereof.

Generally, chemically-treated solid oxides exhibit enhanced acidity as compared to the corresponding untreated solid oxide compound. The chemically-treated solid oxide also functions as a catalyst activator as compared to the corresponding untreated solid oxide. While the chemically-treated solid oxide activates the transition-metal salt complex in the absence of co-catalysts, co-catalysts may also be included in the catalyst composition. The activation function of the activator-support is evident in the enhanced activity of catalyst composition as a whole, as compared to a catalyst composition containing the corresponding untreated solid oxide. However, it is believed that the chemically-treated solid oxide can function as an activator, even in the absence of an organoaluminum compound, aluminoxanes, organoboron or organoborate compounds, ionizing ionic compounds, and the like.

The chemically-treated solid oxide can comprise a solid oxide treated with an electron-withdrawing anion. While not intending to be bound by the following statement, it is believed that treatment of the solid oxide with an electron-withdrawing component augments or enhances the acidity of the oxide. Thus, either the activator-support exhibits Lewis or Brønsted acidity that is typically greater than the Lewis or Brønsted acid strength of the untreated solid oxide, or the activator-support has a greater number of acid sites than the untreated solid oxide, or both. One method to quantify the acidity of the chemically-treated and untreated solid oxide materials is by comparing the polymerization activities of the treated and untreated oxides under acid catalyzed reactions.

Chemically-treated solid oxides of this disclosure are formed generally from an inorganic solid oxide that exhibits Lewis acidic or Brønsted acidic behavior and has a relatively high porosity. The solid oxide is chemically-treated with an electron-withdrawing component, typically an electron-withdrawing anion, to form an activator-support.

According to one aspect of the present disclosure, the solid oxide used to prepare the chemically-treated solid oxide has a pore volume greater than about 0.1 cc/g. According to another aspect of the present disclosure, the solid oxide has a pore volume greater than about 0.5 cc/g. According to yet another aspect of the present disclosure, the solid oxide has a pore volume greater than about 1.0 cc/g.

In another aspect, the solid oxide has a surface area of from about 100 m$^2$/g to about 1000 m$^2$/g. In yet another aspect, the solid oxide has a surface area of from about 200 m$^2$/g to about 800 m$^2$/g. In still another aspect of the present disclosure, the solid oxide has a surface area of from about 250 m$^2$/g to about 600 m$^2$/g.

The chemically-treated solid oxide can comprise a solid inorganic oxide comprising oxygen and one or more elements selected from Group 2, 3, 4, 5, 6, 7, 8, 9, 10, 11, 12, 13, 14, or of the periodic table, or comprising oxygen and one or more elements selected from the lanthanide or actinide elements (See: Hawley's Condensed Chemical Dictionary, 11th Ed., John Wiley & Sons, 1995; Cotton, F. A., Wilkinson, G., Murillo, C. A., and Bochmann, M., Advanced Inorganic Chemistry, 6th Ed., Wiley-Interscience, 1999). For example, the inorganic oxide can comprise oxygen and an element, or elements, selected from Al, B, Be, Bi, Cd, Co, Cr, Cu, Fe, Ga, La, Mn, Mo, Ni, Sb, Si, Sn, Sr, Th, Ti, V, W, P, Y, Zn, and Zr.

Suitable examples of solid oxide materials or compounds that can be used to form the chemically-treated solid oxide include, but are not limited to, $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof. For example, the solid oxide can comprise silica, alumina, silica-alumina, silica-coated alumina, aluminum phosphate, aluminophosphate, heteropolytungstate, titania, zirconia, magnesia, boria, zinc oxide, mixed oxides thereof, or any combination thereof.

The solid oxide of this disclosure encompasses oxide materials such as alumina, "mixed oxide" compounds thereof such as silica-alumina, and combinations and mixtures thereof. The mixed oxide compounds such as silica-alumina can be single or multiple chemical phases with more than one metal combined with oxygen to form a solid oxide compound. Examples of mixed oxides that can be used in the activator-support of the present disclosure include, but are not limited to, silica-alumina, silica-titania, silica-zirconia, zeolites, various clay minerals, alumina-titania, alumina-zirconia, zinc-aluminate, alumina-boria, silica-boria, aluminophosphate-silica, titania-zirconia, and the like. The solid oxide of this disclosure also encompasses oxide materials such as silica-coated alumina, as described in U.S. Pat. No. 7,884,163, the disclosure of which is incorporated herein by reference in its entirety.

The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect of the present disclosure, the electron-withdrawing component is an electron-withdrawing anion derived from a salt, an acid, or other compound, such as a volatile organic compound, that serves as a source or precursor for that anion. Examples of electron-withdrawing anions include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, and the like, including mixtures and combinations thereof. In addition, other ionic or non-ionic compounds that serve as sources for these electron-withdrawing anions also can be employed in the present disclosure. It is contemplated that the electron-withdrawing anion can be, or can comprise, fluoride, chloride, bromide, phosphate, triflate, bisulfate, or sulfate, and the like, or any combination thereof, in some aspects of this disclosure. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or any combination thereof.

Thus, for example, the activator-support (e.g., chemically-treated solid oxide) used in the catalyst compositions can be, or can comprise, fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof. In one aspect, the activator-support can be, or can comprise, fluorided alumina, sulfated alumina, fluorided silica-alumina, sulfated silica-alumina, fluorided silica-coated alumina, sulfated silica-coated alumina, phosphated silica-coated alumina, and the like, or any combination thereof. In another aspect, the activator-support comprises fluorided alumina; alternatively, comprises chlorided alumina; alternatively, comprises sulfated alumina; alternatively, comprises fluorided silica-alumina; alternatively, comprises sulfated silica-alumina; alternatively, comprises fluorided silica-zirconia; alternatively, comprises chlorided silica-zirconia; or alternatively, comprises fluorided silica-coated alumina.

When the electron-withdrawing component comprises a salt of an electron-withdrawing anion, the counterion or cation of that salt can be selected from any cation that allows the salt to revert or decompose back to the acid during calcining. Factors that dictate the suitability of the particular salt to serve as a source for the electron-withdrawing anion include, but are not limited to, the solubility of the salt in the desired solvent, the lack of adverse reactivity of the cation, ion-pairing effects between the cation and anion, hygroscopic properties imparted to the salt by the cation, and the like, and thermal stability of the anion. Examples of suitable cations in the salt of the electron-withdrawing anion include, but are not limited to, ammonium, trialkyl ammonium, tetraalkyl ammonium, tetraalkyl phosphonium, $H^+$, $[H(OEt_2)_2]^+$, and the like.

Further, combinations of one or more different electron-withdrawing anions, in varying proportions, can be used to tailor the specific acidity of the activator-support to the desired level. Combinations of electron-withdrawing components can be contacted with the oxide material simultaneously or individually, and in any order that affords the desired chemically-treated solid oxide acidity. For example, one aspect of this disclosure is employing two or more electron-withdrawing anion source compounds in two or more separate contacting steps.

Thus, one example of such a process by which a chemically-treated solid oxide is prepared is as follows: a selected solid oxide, or combination of solid oxides, is contacted with a first electron-withdrawing anion source compound to form a first mixture; this first mixture is calcined and then contacted with a second electron-withdrawing anion source compound to form a second mixture; the second mixture is then calcined to form a treated solid oxide. In such a process, the first and second electron-withdrawing anion source compounds can be either the same or different compounds.

According to another aspect of the present disclosure, the chemically-treated solid oxide comprises a solid inorganic oxide material, a mixed oxide material, or a combination of inorganic oxide materials, that is chemically-treated with an electron-withdrawing component, and optionally treated with a metal source, including metal salts, metal ions, or other metal-containing compounds. Nonlimiting examples of the metal or metal ion include zinc, nickel, vanadium, titanium, silver, copper, gallium, tin, tungsten, molybdenum, zirconium, and the like, or combinations thereof. Examples of chemically-treated solid oxides that contain a metal or metal ion include, but are not limited to, chlorided zinc-impregnated alumina, fluorided titanium-impregnated alumina, fluorided zinc-impregnated alumina, chlorided zinc-impregnated silica-alumina, fluorided zinc-impregnated silica-alumina, sulfated zinc-impregnated alumina, chlorided zinc aluminate, fluorided zinc aluminate, sulfated zinc aluminate, silica-coated alumina treated with hexafluorotitanic acid, silica-coated alumina treated with zinc and then fluorided, and the like, or any combination thereof.

Any method of impregnating the solid oxide material with a metal can be used. The method by which the oxide is contacted with a metal source, typically a salt or metal-containing compound, can include, but is not limited to, gelling, co-gelling, impregnation of one compound onto another, and the like. If desired, the metal-containing compound is added to or impregnated into the solid oxide in solution form, and subsequently converted into the supported metal upon calcining. Accordingly, the solid inorganic oxide can further comprise a metal selected from zinc, titanium, nickel, vanadium, silver, copper, gallium, tin, tungsten, molybdenum, and the like, or combinations of these metals. For example, zinc is often used to impregnate the solid oxide because it can provide improved catalyst activity at a low cost.

The solid oxide can be treated with metal salts or metal-containing compounds before, after, or at the same time that the solid oxide is treated with the electron-withdrawing anion. Following any contacting method, the contacted mixture of solid compound, electron-withdrawing anion, and the metal ion is typically calcined. Alternatively, a solid oxide material, an electron-withdrawing anion source, and the metal salt or metal-containing compound are contacted and calcined simultaneously.

Various processes are used to form the chemically-treated solid oxide useful in the present disclosure. The chemically-treated solid oxide can comprise the contact product of one or more solid oxides with one or more electron-withdrawing anion sources. It is not required that the solid oxide be calcined prior to contacting the electron-withdrawing anion source. The contact product typically is calcined either during or after the solid oxide is contacted with the electron-withdrawing anion source. The solid oxide can be calcined or uncalcined. Various processes to prepare solid oxide activator-supports that can be employed in this disclosure have been reported. For example, such methods are described in U.S. Pat. Nos. 6,107,230; 6,165,929; 6,294,494; 6,300,271; 6,316,553; 6,355,594; 6,376,415; 6,388,017; 6,391,816; 6,395,666; 6,524,987; 6,548,441; 6,548,442; 6,576,583; 6,613,712; 6,632,894; 6,667,274; and 6,750,302; the disclosures of which are incorporated herein by reference in their entirety.

According to one aspect of the present disclosure, the solid oxide material is chemically-treated by contacting it with an electron-withdrawing component, typically an electron-withdrawing anion source. Further, the solid oxide material optionally is chemically treated with a metal ion, and then calcined to form a metal-containing or metal-impregnated chemically-treated solid oxide. According to another aspect of the present disclosure, the solid oxide material and electron-withdrawing anion source are contacted and calcined simultaneously.

The method by which the oxide is contacted with the electron-withdrawing component, typically a salt or an acid of an electron-withdrawing anion, can include, but is not limited to, gelling, co-gelling, impregnation of one compound onto another, and the like. Thus, following any contacting method, the contacted mixture of the solid oxide, electron-withdrawing anion, and optional metal ion, is calcined.

The solid oxide activator-support (i.e., chemically-treated solid oxide) thus can be produced by a process comprising:
1) contacting a solid oxide (or solid oxides) with an electron-withdrawing anion source compound (or compounds) to form a first mixture; and
2) calcining the first mixture to form the solid oxide activator-support.

According to another aspect of the present disclosure, the solid oxide activator-support (chemically-treated solid oxide) is produced by a process comprising:
1) contacting a solid oxide (or solid oxides) with a first electron-withdrawing anion source compound to form a first mixture;
2) calcining the first mixture to produce a calcined first mixture;
3) contacting the calcined first mixture with a second electron-withdrawing anion source compound to form a second mixture; and
4) calcining the second mixture to form the solid oxide activator-support.

According to yet another aspect of the present disclosure, the chemically-treated solid oxide is produced or formed by contacting the solid oxide with the electron-withdrawing anion source compound, where the solid oxide compound is calcined before, during, or after contacting the electron-withdrawing anion source, and where there is a substantial absence of aluminoxanes, organoboron or organoborate compounds, and ionizing ionic compounds.

Calcining of the treated solid oxide generally is conducted in an ambient atmosphere, typically in a dry ambient atmosphere, at a temperature from about 200° C. to about 900° C., and for a time of about 1 minute to about 100 hours. Calcining can be conducted at a temperature of from about 300° C. to about 800° C., or alternatively, at a temperature of from about 400° C. to about 700° C. Calcining can be conducted for about 30 minutes to about 50 hours, or for about 1 hour to about 15 hours. Thus, for example, calcining can be carried out for about 1 to about 10 hours at a temperature of from about 350° C. to about 550° C. Any suitable ambient atmosphere can be employed during calcining. Generally, calcining is conducted in an oxidizing atmosphere, such as air. Alternatively, an inert atmosphere, such as nitrogen or argon, or a reducing atmosphere, such as hydrogen or carbon monoxide, can be used.

According to one aspect of the present disclosure, the solid oxide material is treated with a source of halide ion, sulfate ion, or a combination of anions, optionally treated with a metal ion, and then calcined to provide the chemically-treated solid oxide in the form of a particulate solid. For example, the solid oxide material can be treated with a source of sulfate (termed a "sulfating agent"), a source of chloride ion (termed a "chloriding agent"), a source of fluoride ion (termed a "fluoriding agent"), or a combination thereof, and calcined to provide the solid oxide activator. Useful acidic activator-supports include, but are not limited to, bromided alumina, chlorided alumina, fluorided alumina, sulfated alumina, bromided silica-alumina, chlorided silica-alumina, fluorided silica-alumina, sulfated silica-alumina, bromided silica-zirconia, chlorided silica-zirconia, fluorided silica-zirconia, sulfated silica-zirconia, fluorided silica-titania, alumina treated with hexafluorotitanic acid, silica-coated alumina treated with hexafluorotitanic acid, silica-alumina treated with hexafluorozirconic acid, silica-alumina treated with trifluoroacetic acid, fluorided boria-alumina, silica treated with tetrafluoroboric acid, alumina treated with tetrafluoroboric acid, alumina treated with hexafluorophosphoric acid, a pillared clay, such as a pillared montmorillonite, optionally treated with fluoride, chloride, or sulfate; phosphated alumina or other aluminophosphates optionally treated with sulfate, fluoride, or chloride; or any combination of the above. Further, any of these activator-supports optionally can be treated with a metal ion.

The chemically-treated solid oxide can comprise a fluorided solid oxide in the form of a particulate solid. The fluorided solid oxide can be formed by contacting a solid oxide with a fluoriding agent. The fluoride ion can be added to the oxide by forming a slurry of the oxide in a suitable solvent such as alcohol or water including, but not limited to, the one to three carbon alcohols because of their volatility and low surface tension. Examples of suitable fluoriding agents include, but are not limited to, hydrofluoric acid (HF), ammonium fluoride ($NH_4F$), ammonium bifluoride ($NH_4HF_2$), ammonium tetrafluoroborate ($NH_4BF_4$), ammonium silicofluoride (hexafluorosilicate) (($NH_4)_2SiF_6$), ammonium hexafluorophosphate ($NH_4 PF_6$), hexafluorotitanic acid ($H_2TiF_6$), ammonium hexafluorotitanic acid (($NH_4)_2TiF_6$), hexafluorozirconic acid ($H_2ZrF_6$), $AlF_3$, $NH_4AlF_4$, analogs thereof, and combinations thereof. Triflic acid and ammonium triflate also can be employed. For example, ammonium bifluoride ($NH_4HF_2$) can be used as the fluoriding agent, due to its ease of use and availability.

If desired, the solid oxide is treated with a fluoriding agent during the calcining step. Any fluoriding agent capable of thoroughly contacting the solid oxide during the calcining step can be used. For example, in addition to those fluoriding agents described previously, volatile organic fluoriding agents can be used. Examples of volatile organic fluoriding agents useful in this aspect of the disclosure include, but are not limited to, freons, perfluorohexane, perfluorobenzene, fluoromethane, trifluoroethanol, and the like, and combinations thereof. Calcining temperatures generally must be high enough to decompose the compound and release fluoride. Gaseous hydrogen fluoride (HF) or fluorine ($F_2$) itself also can be used with the solid oxide if fluorided while calcining. Silicon tetrafluoride ($SiF_4$) and compounds containing tetrafluoroborate ($BF_4^-$) also can be employed. One convenient method of contacting the solid oxide with the fluoriding agent is to vaporize a fluoriding agent into a gas stream used to fluidize the solid oxide during calcination.

Similarly, in another aspect of this disclosure, the chemically-treated solid oxide comprises a chlorided solid oxide in the form of a particulate solid. The chlorided solid oxide is formed by contacting a solid oxide with a chloriding agent. The chloride ion can be added to the oxide by forming a slurry of the oxide in a suitable solvent. The solid oxide can be treated with a chloriding agent during the calcining step. Any chloriding agent capable of serving as a source of chloride and thoroughly contacting the oxide during the calcining step can be used, such as $SiCl_4$, $SiMe_2Cl_2$, $TiCl_4$, $BCl_3$, and the like, including mixtures thereof. Volatile organic chloriding agents can be used. Examples of suitable volatile organic chloriding agents include, but are not limited to, certain freons, perchlorobenzene, chloromethane, dichloromethane, chloroform, carbon tetrachloride, trichloroethanol, and the like, or any combination thereof. Gaseous hydrogen chloride or chlorine itself also can be used with the solid oxide during calcining. One convenient method of contacting the oxide with the chloriding agent is to vaporize a chloriding agent into a gas stream used to fluidize the solid oxide during calcination.

The amount of fluoride or chloride ion present before calcining the solid oxide generally is from about 1 to about 50% by weight, where the weight percent is based on the weight of the solid oxide, for example, silica-alumina, before calcining. According to another aspect of this disclosure, the amount of fluoride or chloride ion present before calcining the solid oxide is from about 1 to about 25% by weight, and according to another aspect of this disclosure, from about 2 to about 20% by weight. According to yet another aspect of this disclosure, the amount of fluoride or chloride ion present before calcining the solid oxide is from about 4 to about 10% by weight. Once impregnated with halide, the halided oxide can be dried by any suitable method including, but not limited to, suction filtration followed by evaporation, drying under vacuum, spray drying, and the like, although it is also possible to initiate the calcining step immediately without drying the impregnated solid oxide.

The silica-alumina used to prepare the treated silica-alumina typically has a pore volume greater than about 0.5 cc/g. According to one aspect of the present disclosure, the pore volume is greater than about 0.8 cc/g, and according to another aspect of the present disclosure, greater than about 1.0 cc/g. Further, the silica-alumina generally has a surface area greater than about 100 $m^2$/g. According to another aspect of this disclosure, the surface area is greater than about 250 $m^2$/g. Yet, in another aspect, the surface area is greater than about 350 $m^2$/g.

The silica-alumina utilized in the present disclosure typically has an alumina content from about 5 to about 95% by weight. According to one aspect of this disclosure, the alumina content of the silica-alumina is from about 5 to about 50%, or from about 8% to about 30%, alumina by weight. In another aspect, high alumina content silica-alumina compounds can employed, in which the alumina content of these silica-alumina compounds typically ranges from about 60% to about 90%, or from about 65% to about 80%, alumina by weight. According to yet another aspect of this disclosure, the solid oxide component comprises alumina without silica, and according to another aspect of this disclosure, the solid oxide component comprises silica without alumina.

The sulfated solid oxide comprises sulfate and a solid oxide component, such as alumina or silica-alumina, in the form of a particulate solid. Optionally, the sulfated oxide is treated further with a metal ion such that the calcined sulfated oxide comprises a metal. According to one aspect of the present disclosure, the sulfated solid oxide comprises sulfate and alumina. In some instances, the sulfated alumina is formed by a process wherein the alumina is treated with a sulfate source, for example, sulfuric acid or a sulfate salt such as ammonium sulfate. This process is generally performed by forming a slurry of the alumina in a suitable solvent, such as alcohol or water, in which the desired concentration of the sulfating agent has been added. Suitable organic solvents include, but are not limited to, the one to three carbon alcohols because of their volatility and low surface tension.

According to one aspect of this disclosure, the amount of sulfate ion present before calcining is from about 0.5 to about 100 parts by weight sulfate ion to about 100 parts by weight solid oxide. According to another aspect of this disclosure, the amount of sulfate ion present before calcining is from about 1 to about 50 parts by weight sulfate ion to about 100 parts by weight solid oxide, and according to still another aspect of this disclosure, from about 5 to about 30 parts by weight sulfate ion to about 100 parts by weight solid oxide.

These weight ratios are based on the weight of the solid oxide before calcining. Once impregnated with sulfate, the sulfated oxide can be dried by any suitable method including, but not limited to, suction filtration followed by evaporation, drying under vacuum, spray drying, and the like, although it is also possible to initiate the calcining step immediately.

According to another aspect of the present disclosure, the activator-support used in preparing the catalyst compositions of this disclosure comprises an ion-exchangeable activator-support, including but not limited to silicate and aluminosilicate compounds or minerals, either with layered or non-layered structures, and combinations thereof. In another aspect of this disclosure, ion-exchangeable, layered aluminosilicates such as pillared clays are used as activator-supports. When the acidic activator-support comprises an ion-exchangeable activator-support, it can optionally be treated with at least one electron-withdrawing anion such as those disclosed herein, though typically the ion-exchangeable activator-support is not treated with an electron-withdrawing anion.

According to another aspect of the present disclosure, the activator-support of this disclosure comprises clay minerals having exchangeable cations and layers capable of expanding. Typical clay mineral activator-supports include, but are not limited to, ion-exchangeable, layered aluminosilicates such as pillared clays. Although the term "support" is used, it is not meant to be construed as an inert component of the catalyst composition, but rather is to be considered an active part of the catalyst composition, because of its intimate association with the transition-metal salt complex component.

According to another aspect of the present disclosure, the clay materials of this disclosure encompass materials either in their natural state or that have been treated with various ions by wetting, ion exchange, or pillaring. Typically, the clay material activator-support of this disclosure comprises clays that have been ion exchanged with large cations, including polynuclear, highly charged metal complex cations. However, the clay material activator-supports of this disclosure also encompass clays that have been ion exchanged with simple salts, including, but not limited to, salts of Al(III), Fe(II), Fe(III), and Zn(II) with ligands such as halide, acetate, sulfate, nitrate, or nitrite.

According to another aspect of the present disclosure, the activator-support comprises a pillared clay. The term "pillared clay" is used to refer to clay materials that have been ion exchanged with large, typically polynuclear, highly charged metal complex cations. Examples of such ions include, but are not limited to, Keggin ions which can have charges such as 7+, various polyoxometallates, and other large ions. Thus, the term pillaring refers to a simple exchange reaction in which the exchangeable cations of a clay material are replaced with large, highly charged ions, such as Keggin ions. These polymeric cations are then immobilized within the interlayers of the clay and when calcined are converted to metal oxide "pillars," effectively supporting the clay layers as column-like structures. Thus, once the clay is dried and calcined to produce the supporting pillars between clay layers, the expanded lattice structure is maintained and the porosity is enhanced. The resulting pores can vary in shape and size as a function of the pillaring material and the parent clay material used. Examples of pillaring and pillared clays are found in: T. J. Pinnavaia, Science 220 (4595), 365-371 (1983); J. M. Thomas, Intercalation Chemistry, (S. Whittington and A. Jacobson, eds.) Ch. 3, pp. 55-99, Academic Press, Inc., (1972); U.S. Pat. Nos. 4,452,910; 5,376,611; and 4,060,480; the disclosures of which are incorporated herein by reference in their entirety.

The pillaring process utilizes clay minerals having exchangeable cations and layers capable of expanding. Any pillared clay that can enhance the polymerization of olefins in the catalyst composition of the present disclosure can be used. Therefore, suitable clay minerals for pillaring include, but are not limited to, allophanes; smectites, both dioctahedral (Al) and tri-octahedral (Mg) and derivatives thereof such as montmorillonites (bentonites), nontronites, hectorites, or laponites; halloysites; vermiculites; micas; fluoromicas; chlorites; mixed-layer clays; the fibrous clays including but not limited to sepiolites, attapulgites, and palygorskites; a serpentine clay; illite; laponite; saponite; and any combination thereof. In one aspect, the pillared clay activator-support comprises bentonite or montmorillonite. The principal component of bentonite is montmorillonite.

The pillared clay can be pretreated if desired. For example, a pillared bentonite is pretreated by drying at about 300° C. under an inert atmosphere, typically dry nitrogen, for about 3 hours, before being added to the polymerization reactor. Although an exemplary pretreatment is described herein, it should be understood that the preheating can be carried out at many other temperatures and times, including any combination of temperature and time steps, all of which are encompassed by this disclosure.

The activator-support used to prepare the catalyst compositions of the present disclosure can be combined with other inorganic support materials, including, but not limited to, zeolites, inorganic oxides, phosphated inorganic oxides, and the like. In one aspect, typical support materials that are used include, but are not limited to, silica, silica-alumina, alumina, titania, zirconia, magnesia, boria, thoria, aluminophosphate, aluminum phosphate, silica-titania, coprecipitated silica/titania, mixtures thereof, or any combination thereof. In an embodiment, the activator-support comprises a sulfated solid oxide activator support (S-SSA).

The process of making these activator-supports may include precipitation, co-precipitation, impregnation, gelation, pore-gelation, calcining (at up to 900° C.), spray-drying, flash-drying, rotary drying and calcining, milling, sieving, and similar operations.

In an embodiment, the catalyst composition optionally comprises a metal alkyl or a metalloid alkyl which may function as a cocatalyst. Generally, the metal alkyl compound which can be utilized in the catalyst system of this disclosure can be any heteroleptic or homoleptic metal alkyl compound. In an embodiment, the metal alkyl can comprise, consist essentially of, or consist of, a non-halide metal alkyl, a metal alkyl halide, or any combination thereof; alternatively, a non-halide metal alkyl; or alternatively, a metal alkyl halide.

In an embodiment, the metal of the metal alkyl can comprise, consist essentially of, or consist of, a group 1, 2, 11, 12, 13, or 14 metal; or alternatively, a group 13 or 14 metal; or alternatively, a group 13 metal. In some embodiments, the metal of the metal alkyl (non-halide metal alkyl or metal alkyl halide) can be lithium, sodium, potassium, rubidium, cesium, beryllium, magnesium, calcium, strontium, barium, zinc, cadmium, boron, aluminum, or tin; alternatively, lithium, sodium, potassium, magnesium, calcium, zinc, boron, aluminum, or tin; alternatively, lithium, sodium, or potassium; alternatively, magnesium, calcium; alternatively, lithium; alternatively, sodium; alternatively, potassium; alternatively, magnesium; alternatively, calcium; alternatively, zinc; alternatively, boron; alternatively, aluminum; or alternatively, tin. In some embodiments, the metal alkyl (non-halide metal alkyl or metal alkyl halide) can comprise, consist essentially of, or consist of, a lithium alkyl, a sodium alkyl, a magnesium alkyl, a boron alkyl, a zinc alkyl, or an aluminum alkyl. In some embodiments, the metal alkyl (non-halide metal alkyl or metal alkyl halide) can comprise, consist essentially of, or consist of, an aluminum alkyl.

In an embodiment, the aluminum alkyl can be a trialkylaluminum, an alkylaluminum halide, an alkylaluminum alkoxide, an aluminoxane, or any combination thereof. In some embodiments, the aluminum alkyl can be a trialkylaluminum, an alkylaluminum halide, an aluminoxane, or any combination thereof; or alternatively, a trialkylaluminum, an aluminoxane, or any combination thereof. In other embodiments, the aluminum alkyl can be a trialkylaluminum; alternatively, an alkylaluminum halide; alternatively, an alkylaluminum alkoxide; or alternatively, an aluminoxane.

In a non-limiting embodiment, the aluminoxane can have a repeating unit characterized by the Formula I:

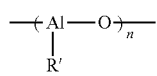

Formula I wherein R' is a linear or branched alkyl group. Alkyl groups for metal alkyls have been independently described herein and can be utilized without limitation to further describe the aluminoxanes having Formula I. Generally, n of Formula I is greater than 1; or alternatively, greater than 2. In an embodiment, n can range from 2 to 15; or alternatively, range from 3 to 10. In an aspect, each halide of any metal alkyl halide disclosed herein can independently be fluoride, chloride, bromide, or iodide; alternatively, chloride, bromide, or iodide. In an embodiment, each halide of any metal alkyl halide disclosed herein can be fluoride; alternatively, chloride; alternatively, bromide; or alternatively, iodide.

In an aspect, the alkyl group of any metal alkyl disclosed herein (non-halide metal alkyl or metal alkyl halide) can each independently be a $C_1$ to $C_{20}$ alkyl group; alternatively, a $C_1$ to $C_{10}$ alkyl group; or alternatively, a $C_1$ to $C_6$ alkyl group. In an embodiment, the alkyl group(s) can each independently be a methyl group, an ethyl group, a propyl group, a butyl group, a pentyl group, a hexyl group, a heptyl group, or an octyl group; alternatively, a methyl group, an ethyl group, a butyl group, a hexyl group, or an octyl group. In some embodiments, the alkyl group can each independently be a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, the alkoxide group of any metal alkyl alkoxide disclosed herein can each independently be a $C_1$ to $C_{20}$ alkoxy group; alternatively, a $C_1$ to $C_{10}$ alkoxy group; or alternatively, a $C_1$ to $C_6$ alkoxy group. In an embodiment, each alkoxide group of any metal alkyl alkoxide disclosed herein can each independently be a methoxy group, an ethoxy group, a propoxy group, a butoxy group, a pentoxy group, a hexoxy group, a heptoxy group, or an octoxy group; alternatively, a methoxy group, an ethoxy group, a butoxy group, a hexoxy group, or an octoxy group. In some embodiments, each alkoxide group of any metal alkyl alkoxide disclosed herein can each independently be a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting embodiment, useful metal alkyls can include methyl lithium, n-butyl lithium, sec-butyl lithium, tert-butyl lithium, diethyl magnesium, di-n-butylmagnesium, ethylmagnesium chloride, n-butylmagnesium chloride, and diethyl zinc.

In a non-limiting embodiment, useful trialkylaluminum compounds can include trimethylaluminum, triethylaluminum, tripropylaluminum, tributylaluminum, trihexylaluminum, trioctylaluminum, or mixtures thereof. In some non-limiting embodiments, trialkylaluminum compounds can include trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting embodiments, useful trialkylaluminum compounds can include trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting embodiment, useful alkylaluminum halides can include diethylaluminum chloride, diethylaluminum bromide, ethylaluminum dichloride, ethylaluminum sesquichloride, and mixtures thereof. In some non-limiting embodiments, useful alkylaluminum halides can include diethylaluminum chloride, ethylaluminum dichloride, ethylaluminum sesquichloride, and mixtures thereof. In other non-limiting embodiments, useful alkylaluminum halides can include diethylaluminum chloride; alternatively, diethylaluminum bromide; alternatively, ethylaluminum dichloride; or alternatively, ethylaluminum sesquichloride.

In a non-limiting embodiment, useful aluminoxanes can include methylaluminoxane (MAO), ethylaluminoxane, modified methylaluminoxane (MMAO), n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, or mixtures thereof. In some non-limiting embodiments, useful aluminoxanes can include methylaluminoxane (MAO), modified methylaluminoxane (MMAO), isobutyl aluminoxane, t-butyl aluminoxane, or mixtures thereof. In other non-limiting embodiments, useful aluminoxanes can include methylaluminoxane (MAO); alternatively, ethylaluminoxane; alternatively, modified methylaluminoxane (MMAO); alternatively, n-propylaluminoxane; alternatively, iso-propylaluminoxane; alternatively, n-butylaluminoxane; alternatively, sec-butylaluminoxane; alternatively, iso-butylaluminoxane; alternatively, t-butyl aluminoxane; alternatively, 1-pentylaluminoxane; alternatively, 2-pentylaluminoxane; alternatively, 3-pentylaluminoxane; alternatively, iso-pentylaluminoxane; or alternatively, neopentylaluminoxane.

In an embodiment, the metal alkyl comprises comprise an organoboron compound or an organoborate compound. Organoboron or organoborate compounds include neutral boron compounds, borate salts, and the like, or combinations thereof. For example, fluoroorgano boron compounds and fluoroorgano borate compounds are contemplated.

Any fluoroorgano boron or fluoroorgano borate compound can be utilized with the present disclosure. Examples of fluoroorgano borate compounds that can be used in the present disclosure include, but are not limited to, fluorinated aryl borates such as N,N-dimethylanilinium tetrakis(pentafluorophenyl)borate, triphenylcarbenium tetrakis(pentafluorophenyl)borate, lithium tetrakis(pentafluorophenyl)borate, N,N-dimethylanilinium tetrakis[3,5-bis(trifluoro-methyl)phenyl]borate, triphenylcarbenium tetrakis[3,5-bis(trifluoromethyl)phenyl]borate, and the like, or mixtures thereof. Examples of fluoroorgano boron compounds that can be used in the present disclosure include, but are not limited to, tris (pentafluorophenyl)boron, tris[3,5-bis(trifluoromethyl)phenyl]boron, and the like, or mixtures thereof. Although not intending to be bound by the following theory, these examples of fluoroorgano borate and fluoroorgano boron compounds, and related compounds, are thought to form "weakly-coordinating" anions when combined with organometal compounds, as disclosed in U.S. Pat. No. 5,919,983, the disclosure of which is incorporated herein by reference in its entirety. Applicants also contemplate the use of diboron, or bis-boron, compounds or other bifunctional compounds containing two or more boron atoms in the chemical structure, such as disclosed in J. Am. Chem. Soc., 2005, 127, pp. 14756-14768, the content of which is incorporated herein by reference in its entirety.

In one aspect, the weight ratio of the treated solid oxide component to the transition metal salt complex may be from about 10,000:1 to about 1:1. In another aspect, the weight ratio of the treated solid oxide component to the transition metal salt complex in the catalyst composition may be from about 1000:1 to about 10:1, an in yet another aspect, from about 500:1 to about 20:1. These weight ratios are based on the combined weights of cocatalyst (e.g., organoaluminum, treated oxide) and transition metal salt complex used to prepare the catalyst composition, regardless of the order of contacting the catalyst components.

In an embodiment, catalyst compositions of the type disclosed herein display a catalytic activity in a polymerization reaction ranging from about 1 g PE/g cat·h to about 1,000,000 kg PE/g cat·h, alternatively from about 1 kg PE/g cat·h to about 100,000 kg PE/g cat·h, or alternatively from about 10 kg PE/g cat·h to about 10,000 kg PE/g cat·h. Catalyst system activity is defined as grams of a product produced per gram of the transition metal salt complex utilized in the catalyst system over the first 45 minutes of a reaction beginning from the time when the complete catalyst system is contacted with the olefin. Catalyst system activity can be stated in terms of various products of an olefin oligomerization or polymerization.

In an embodiment, a catalyst composition of the type described herein may function in the polymerization of olefins. In an embodiment, a monomer (e.g., ethylene) is polymerized using the methodologies disclosed herein to produce a polymer. The polymer may comprise a homopolymer, a copolymer, and/or combinations thereof. In an embodiment, the polymer is a copolymer comprising ethylene and one or more comonomers such as, for example, alpha olefins. Examples of suitable comonomers include, but are not limited to, unsaturated hydrocarbons having from 3 to 20 carbon atoms such as propylene, 1-butene, 1-pentene, 1-hexene, 3-methyl-1-butene, 4-methyl-1-pentene, 1-heptene, 1-octene, 1-nonene, 1-decene, and mixtures thereof. In an embodiment, the comonomer is 1-hexene. In an embodiment, the commoner may be present in the polymer in an amount of equal to or less than about 0.5 mol. %, alternatively less than about 0.4 mol. %, alternatively less than about 0.3 mol. % or alternatively less than about 0.2 mol. %.

In an embodiment, a catalyst system of the type disclosed herein is used to prepare a polymer by any olefin polymerization method, using various types of polymerization reactors. As used herein, "polymerization reactor" includes any reactor capable of polymerizing olefin monomers to produce homopolymers and/or copolymers. Homopolymers and/or copolymers produced in the reactor may be referred to as resin and/or polymers. The various types of reactors include, but are not limited to those that may be referred to as batch, slurry, gas-phase, solution, high pressure, tubular, autoclave, or other reactor and/or reactors. Gas phase reactors may comprise fluidized bed reactors or staged horizontal reactors. Slurry reactors may comprise vertical and/or horizontal loops. High pressure reactors may comprise autoclave and/or tubular reactors. Reactor types may include batch and/or continuous processes. Continuous processes may use intermittent and/or continuous product discharge or transfer. Processes may also include partial or full direct recycle of un-reacted monomer, un-reacted comonomer, catalyst and/or co-catalysts, diluents, and/or other materials of the polymerization process. Polymerization reactor systems of the present disclosure may comprise one type of reactor in a system or multiple reactors of the same or different type, operated in any suitable configuration. Production of polymers in multiple reactors may include several stages in at least two separate polymerization reactors interconnected by a transfer system making it possible to transfer the polymers resulting from the first polymerization reactor into the second reactor. Alternatively, polymerization in multiple reactors may include the transfer, either manual or automatic, of polymer from one reactor to subsequent reactor or reactors for additional polymerization. Alternatively, multi-stage or multi-step polymerization may take place in a single reactor, wherein the conditions are changed such that a different polymerization reaction takes place.

The desired polymerization conditions in one of the reactors may be the same as or different from the operating conditions of any other reactors involved in the overall process of producing the polymer of the present disclosure. Multiple reactor systems may include any combination including, but not limited to multiple loop reactors, multiple gas phase reactors, a combination of loop and gas phase reactors, multiple high pressure reactors or a combination of high pressure with loop and/or gas reactors. The multiple reactors may be operated in series or in parallel. In an embodiment, any arrangement and/or any combination of reactors may be employed to produce the polymer of the present disclosure According to one embodiment, the polymerization reactor system may comprise at least one loop slurry reactor. Such reactors are commonplace, and may comprise vertical or horizontal loops. Monomer, diluent, catalyst system, and optionally any comonomer may be continuously fed to a loop slurry reactor, where polymerization occurs. Generally, continuous processes may comprise the continuous introduction of a monomer, a catalyst, and/or a diluent into a polymerization reactor and the continuous removal from this reactor of a suspension comprising polymer particles and the diluent. Reactor effluent may be flashed to remove the liquids that comprise the diluent from the solid polymer, monomer and/or comonomer. Various technologies may be used for this separation step including but not limited to, flashing that may include any combination of heat addition and pressure reduction; separation by cyclonic action in either a cyclone or hydrocyclone; separation by centrifugation; or other appropriate method of separation.

Typical slurry polymerization processes (also known as particle-form processes) are disclosed in U.S. Pat. Nos. 3,248,179, 4,501,885, 5,565,175, 5,575,979, 6,239,235, 6,262,191 and 6,833,415, for example; each of which are herein incorporated by reference in their entirety.

Suitable diluents used in slurry polymerization include, but are not limited to, the monomer being polymerized and hydrocarbons that are liquids under reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used. An example is polymerization of propylene monomer as disclosed in U.S. Pat. No. 5,455,314, which is incorporated by reference herein in its entirety.

According to yet another embodiment, the polymerization reactor may comprise at least one gas phase reactor. Such systems may employ a continuous recycle stream containing one or more monomers continuously cycled through a fluidized bed in the presence of the catalyst under polymerization conditions. A recycle stream may be withdrawn from the fluidized bed and recycled back into the reactor. Simultaneously, polymer product may be withdrawn from the reactor and new or fresh monomer may be added to replace the polymerized monomer. Such gas phase reactors may comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 4,588,790, 5,352,749, and 5,436,304, each of which is incorporated by reference in its entirety herein.

According to still another embodiment, a high pressure polymerization reactor may comprise a tubular reactor or an autoclave reactor. Tubular reactors may have several zones where fresh monomer, initiators, or catalysts are added. Monomer may be entrained in an inert gaseous stream and introduced at one zone of the reactor. Initiators, catalysts, and/or catalyst components may be entrained in a gaseous stream and introduced at another zone of the reactor. The gas streams may be intermixed for polymerization. Heat and pressure may be employed appropriately to obtain optimal polymerization reaction conditions.

According to yet another embodiment, the polymerization reactor may comprise a solution polymerization reactor wherein the monomer is contacted with the catalyst composition by suitable stirring or other means. A carrier comprising an organic diluent or excess monomer may be employed. If desired, the monomer may be brought in the vapor phase into contact with the catalytic reaction product, in the presence or absence of liquid material. The polymerization zone is maintained at temperatures and pressures that will result in the formation of a solution of the polymer in a reaction medium. Agitation may be employed to obtain better temperature control and to maintain uniform polymerization mixtures throughout the polymerization zone. Adequate means are utilized for dissipating the exothermic heat of polymerization.

Polymerization reactors suitable for the present disclosure may further comprise any combination of at least one raw material feed system, at least one feed system for catalyst or catalyst components, and/or at least one polymer recovery system. Suitable reactor systems for the present invention may further comprise systems for feedstock purification, catalyst storage and preparation, extrusion, reactor cooling, polymer recovery, fractionation, recycle, storage, loadout, laboratory analysis, and process control.

Conditions that are controlled for polymerization efficiency and to provide polymer properties include, but are not limited to temperature, pressure, type and quantity of catalyst or co-catalyst, and the concentrations of various reactants. Polymerization temperature can affect catalyst productivity, polymer molecular weight and molecular weight distribution. Suitable polymerization temperatures may be any temperature below the de-polymerization temperature, according to the Gibbs Free Energy Equation. Typically, this includes from about 60° C. to about 280° C., for example, and/or from about 70° C. to about 110° C., depending upon the type of polymerization reactor and/or polymerization process.

Suitable pressures will also vary according to the reactor and polymerization process. The pressure for liquid phase polymerization in a loop reactor is typically less than 1000 psig. Pressure for gas phase polymerization is usually at about 200-500 psig. High pressure polymerization in tubular or autoclave reactors is generally run at about 20,000 to 75,000 psig. Polymerization reactors can also be operated in a supercritical region occurring at generally higher temperatures and pressures. Operation above the critical point of a pressure/temperature diagram (supercritical phase) may offer advantages.

The concentration of various reactants can be controlled to produce polymers with certain physical and mechanical properties. The proposed end-use product that will be formed by the polymer and the method of forming that product may be varied to determine the desired final product properties. Mechanical properties include, but are not limited to tensile strength, flexural modulus, impact resistance, creep, stress relaxation and hardness tests. Physical properties include, but are not limited to density, molecular weight, molecular weight distribution, melting temperature, glass transition temperature, temperature melt of crystallization, density, stereoregularity, crack growth, short chain branching, long chain branching and rheological measurements.

The concentrations of monomer, co-monomer, hydrogen, co-catalyst, modifiers, and electron donors are generally important in producing specific polymer properties. Comonomer may be used to control product density. Hydrogen may be used to control product molecular weight. Co-catalysts may be used to alkylate, scavenge poisons and/or control molecular weight. The concentration of poisons may be minimized, as poisons may impact the reactions and/or otherwise affect polymer product properties. Modifiers may be used to control product properties and electron donors may affect stereoregularity.

In an embodiment, a catalyst composition comprises a transition metal salt characterized by Structure VI, a sulfated solid oxide of the type disclosed herein and an alkylaluminum complex of the type disclosed herein. The catalyst composition can be contacted with a monomer (e.g., ethylene and optional comonomer) under conditions suitable for the formation of a polymer (e.g., polyethylene).

In an embodiment, a monomer (e.g., ethylene) may be polymerized using the methodologies disclosed herein to produce a polymer of the type disclosed herein. The polymer may comprise a homopolymer. In an embodiment, the polymer is a homopolymer. It is to be understood that an inconsequential amount of comonomer may be present in the polymers disclosed herein and the polymer still be considered a homopolymer. Herein an inconsequential amount of a comonomer refers to an amount that does not substantively affect the properties of the polymer disclosed herein. For example a comonomer can be present in an amount of less than about 1.0 wt. %, 0.5 wt. %, 0.1 wt. %, or 0.01 wt. % based on the total weight of polymer.

The polymer may include other additives. Examples of additives include, but are not limited to, antistatic agents, colorants, stabilizers, nucleators, surface modifiers, pigments, slip agents, antiblocks, tackafiers, polymer processing aids, and combinations thereof. Such additives may be used singularly or in combination and may be included in the polymer before, during, or after preparation of the polymer as described herein. Such additives may be added via any suitable technique, for example during an extrusion or compounding step such as during pelletization or subsequent processing into an end use article.

In an embodiment, a polymer of the type described herein is characterized by a density that can be described according to equation (1)

$$\rho > a - b \log M \qquad (1)$$

where "$\rho$" is a density of the polymer in g/cc, and "log M" is a log of the weight-average molecular weight of the polymer and coefficients "a" and "b" may be determined by a least square fit to a data set of log M and measured density values. In an embodiment "a" has a value of 1.0407, and "b" has a value of 0.0145 where the weight-average molecular weight of the polymer (e.g., PE) is from about 50 kg/mol to about 1000 kg/mol. In another embodiment "a" has a value of 1.0417, and "b" has a value of 0.0145 where the weight-average molecular weight of the polymer (e.g., PE) is from about 20 kg/mol to about 2000 kg/mol. In another embodiment "a" has a value of 1.0427, and "b" has a value of 0.0145 where the weight-average molecular weight of the polymer (e.g., PE) is from about 10 kg/mol to about 5000 kg/mol. In an embodiment, a polymer of the type disclosed herein has a density of greater than about 0.94 g/cc, alternatively greater than about 0.95 g/cc or alternatively greater than about 0.955 g/cc.

In an embodiment, a polymer of the type described herein may be of any modality. Herein, the "modality" of a polymer refers to the form of its molecular weight distribution curve, i.e. the appearance of the graph of the polymer weight fraction as a function of its molecular weight. The polymer weight fraction refers to the weight fraction of molecules of a given size. A polymer having a molecular weight distribution curve showing a single peak may be referred to as a unimodal polymer, a polymer having curve showing two distinct peaks may be referred to as bimodal polymer, a polymer having a curve showing three distinct peaks may be referred to as trimodal polymer, a polymer having a curve showing two or more peaks may be referred to as multimodal, etc. Polymer modality may be determined using any suitable methodology such as those described in the examples sections herein.

In an embodiment, a polymer of the type described herein may have a weight average molecular weight ($M_w$) of from about 10 kg/mol to about 5,000 kg/mol, alternatively of from about 20 kg/mol to about 2,000 kg/mol, or alternatively of from about 50 kg/mol to about 1,000 kg/mol. The weight average molecular weight describes the molecular weight distribution of a polymer and is calculated according to Equation 2:

$$M_w = \frac{\Sigma_i N_i M_i^2}{\Sigma_i N_i M_i} \qquad (2)$$

where $N_i$ is the number of molecules of molecular weight $M_i$.

A polymer of the type described herein may be characterized by number average molecular weight ($M_n$) of from about 1 kg/mol to about 1,000 kg/mol, alternatively from about 2 kg/mol to about 500 kg/mol or alternatively from about 3 kg/mol to about 100 kg/mol. The number average molecular weight is the common average of the molecular weights of the individual polymers and may be calculated according to Equation 3:

$$M_n = \frac{\Sigma_i N_i M_i}{\Sigma_i N_i} \qquad (3)$$

where $N_i$ is the number of molecules of molecular weight $M_i$.

A polymer of the type described herein may be characterized by molecular weight distribution (MWD) of greater than about 5, alternatively greater than about 10, alternatively, greater than about 12, or alternatively, greater than about 15. The MWD is the ratio of the $M_w$ to $M_n$, which is also referred to as the polydispersity index (PDI) or more simply as polydispersity.

A polymer of the type described herein may be further characterized by a ratio of z-average molecular weight ($M_z$) to $M_w$ ($M_z/M_w$) of greater than about 4, alternatively, greater than about 5, or alternatively, greater than about 6. The z-average molecular weight is a higher order molecular weight average which is calculated according to Equation 4:

$$M_z = \frac{\Sigma_i N_i M_i^3}{\Sigma_i N_i M_i^2} \qquad (4)$$

where $N_i$ is the amount of substance of species i and $M_i$ is the molecular weight of species i. The ratio of $M_z/M_w$ is another indication of the breadth of the MWD of a polymer.

In an embodiment, a polymer of the type described herein has a melt index, MI, of from about 0.0001 g/10 min. to about 10,000 g/10 min., alternatively from about 0.001 g/10 min. to about 1000 g/10 min. or alternatively from about 0.01 g/10 min. to about 100 g/min. The melt index (MI) refers to the amount of a polymer which can be forced through an extrusion rheometer orifice of 0.0825 inch diameter when subjected to a force of 2160 grams in ten minutes at 190° C., as determined in accordance with ASTM D 1238.

In an embodiment, a polymer of the type described herein has a high load melt index, HLMI, in a range from about 0.1 g/10 min. to about 100,000 g/10 min., alternatively from about 0.5 g/10 min. to about 10,000 g/10 min., or alternatively from about 1 g/10 min. to about 1000 g/10 min. The high load melt index (HLMI) refers to the rate a polymer which can be forced through an extrusion rheometer orifice of 0.0824 inch diameter when subjected to a force of 21,600 grams at 190° C. in accordance with ASTM D 1238.

In an embodiment, a polymer of the type disclosed herein has a Carreau Yasuda 'a' parameter, CY-a (a-eta), in the range of from about 0.05 to about 0.5, alternatively from about 0.1 to about 0.4, or alternatively from about 0.15 to about 0.3. The Carreau Yasuda 'a' parameter (CY-a) is defined as the rheological breath parameter. Rheological breadth refers to the breadth of the transition region between Newtonian and power-law type shear rate for a polymer or the frequency dependence of the viscosity of the polymer. The rheological breadth is a function of the relaxation time distribution of a polymer resin, which in turn is a function of the resin molecular structure or architecture. The CY-a parameter may be obtained by assuming the Cox-Merz rule and calculated by fitting flow curves generated in linear-viscoelastic dynamic oscillatory frequency sweep experiments with a modified Carreau-Yasuda (CY) model, which is represented by Equation (5):

$$E = E_o[1 + (T_\xi \dot{\gamma})^a]^{\frac{n-1}{a}} \quad (5)$$

where
E=viscosity (Pa·s)
$\dot{\gamma}$=shear rate (1/s)
a=rheological breadth parameter
$T_\xi$=relaxation time (s) [describes the location in time of the transition region]
$E_o$=zero shear viscosity (Pa·s) [defines the Newtonian plateau]
n=power law constant [defines the final slope of the high shear rate region]

To facilitate model fitting, the power law constant n is held at a constant value. Details of the significance and interpretation of the CY model and derived parameters may be found in: C. A. Hieber and H. H. Chiang, *Rheol. Acta*, 28, 321 (1989); C. A. Hieber and H. H. Chiang, *Polym. Eng. Sci.*, 32, 931 (1992); and R. B. Bird, R. C. Armstrong and O. Hasseger, *Dynamics of Polymeric Liquids, Volume 1, Fluid Mechanics*, 2nd Edition, John Wiley & Sons (1987), each of which is incorporated by reference herein in its entirety.

In an embodiment, a polymer of the type described herein may have a zero-shear viscosity ($\eta_0$) of greater than about 1000 Pa-s, alternatively greater than about 2000 Pa-s, or alternatively greater than about 5000 Pa-s. In an embodiment, a polymer of the type described herein having a melt index of about 2 may have a zero shear viscosity greater than about 5,000 Pa-s, alternatively, greater than about 10,000 Pa-s, or alternatively, greater than about 15,000 Pa-s.

In an embodiment, a polymer of the type described herein having an HLMI of about 7 g/10 min. may have a zero shear viscosity of greater than about 50,000 Pa-s, alternatively, greater than about 100,000 Pa-s, alternatively, greater than about 500,000 Pa-s. In an alternative embodiment, a polymer of the type described herein having an HLMI of about 1 g/10 min. may have a zero shear viscosity of greater than about 100,000 Pa-s, alternatively, greater than about 500,000 Pa-s, or alternatively, greater than about 1,000,000 Pa-s.

In an embodiment, a polymer of the type described herein having a $M_w$ of about 250 kg/mol may have a zero shear viscosity of greater than about 50,000 Pa-s, alternatively, greater than about 100,000 Pa-s, alternatively, greater than about 500,000 Pa-s. In an alternative embodiment, a polymer of the type described herein having a $M_w$ of about 175 kg/mol may have a zero shear viscosity of greater than about 25,000 Pa-s, alternatively, greater than about 50,000 Pa-s, or alternatively, greater than about 100,000 Pa-s. In an alternative embodiment, a polymer of the type described herein having a $M_w$ of about 125 kg/mol may have a zero shear viscosity of greater than about 8,000 Pa-s, alternatively, greater than about 10,000 Pa-s, or alternatively, greater than about 15,000 Pa-s.

In an embodiment, a polymer of the type disclosed herein has a density of greater than about 0.960 g/cc, alternatively greater than about 0.962 g/cc or alternatively greater than about 0.966 g/cc. Polymers of the type disclosed herein having a density of greater than about 0.960 g/cc, alternatively greater than about 0.962 g/cc or alternatively greater than about 0.966 g/cc may display improved barrier properties. Such polymers are designated polymer compositions having improved barrier properties, PCIB.

In an embodiment, a PCIB of the type described herein may be of any modality. In an embodiment, a PCIB of the type described herein may have a $M_w$ of less than about 145 kg/mol, alternatively, less than about 135 kg/mol or alternatively, less than about 125 kg/mol. Alternatively the $M_w$ may range from about 50 kg/mol to about 145 kg/mol, alternatively from about 75 kg/mol to about 135 kg/mol or alternatively from about 90 kg/mol to about 125 kg/mol.

A PCIB of the type described herein may be characterized by a $M_n$ of from about 1 kg/mol to about 20 kg/mol, alternatively from about 2 kg/mol to about 10 kg/mol or alternatively from about 3 kg/mol to about 8 kg/mol.

A PCIB of the type described herein may be characterized by a MWD of greater than about 7, alternatively greater than about 10, alternatively, greater than about 12, or alternatively, greater than about 15.

A PCIB of the type described herein may be further characterized by a $M_z/M_w$ of greater than about 5, alternatively, greater than about 6, alternatively, greater than about 7.

In an embodiment, a PCIB of the type described herein has a MI of greater than about 0.8 g/10 min., alternatively greater than about 1.5 g/10 min., or alternatively greater than about 1.8 g/10 min. as determined in accordance with ASTM D 1238.

In an embodiment, a PCIB of the type described herein may have a HLMI of greater than about 10 g/10 min., alternatively greater than about 25 g/10 min. or alternatively greater than about 50 g/10 min. as determined in accordance with ASTM D 1238.

In an embodiment, a PCIB of the type disclosed herein has a CY-a in the range of from about 0.05 to about 0.45, alternatively from about 0.1 to about 0.4, or alternatively from about 0.15 to about 0.3.

In an embodiment, a PCIB of the type described herein may have a zero-shear viscosity ($\eta_0$) of from about 1,000 Pa-s to 65,000 Pa-s, alternatively from about 2,000 Pa-s to about 50,000 Pa-s, or alternatively from about 5,000 to 30,000 Pa-s.

PCIBs of the type disclosed herein may be formed into articles of manufacture or end-use articles using techniques known in the art such as extrusion, blow molding, injection molding, fiber spinning, thermoforming, and casting. Polymers of the type disclosed herein may display an improved processability.

In an embodiment, PCIBs of the type described herein disclosed are fabricated into a film. The films of this disclosure may be produced by any suitable method and under any suitable condition for the production of films. In an embodiment, the polymers are formed into films through a blown film process. In a blown film process, plastic melt is extruded through an annular slit die, usually vertically, to form a thin walled tube. Air may then be introduced via a hole in the center of the die to blow up the tube like a balloon. Mounted on top of the die, a high-speed air ring blows onto the hot film to cool it. The tube of film then continues upwards, continually cooling, until it passes through nip rolls where the tube is flattened to create what is known as a lay-flat tube of film. This lay-flat or collapsed tube is then taken back down the extrusion tower via more rollers. On higher output lines, the air inside the bubble is also exchanged. This is known as Internal Bubble Cooling (IBC).

The lay-flat film is then either kept as such or the edges of the lay-flat are slit off to produce two flat film sheets and wound up onto reels. Typically, the expansion ratio between die and blown tube of film would be 1.5 to 4 times the die diameter. The drawdown between the melt wall thickness and the cooled film thickness occurs in both radial and longitudinal directions and is easily controlled by changing the volume of air inside the bubble and by altering the haul off speed. The films formed from polymer resins of this disclosure (e.g., polyethylene) may be of any thickness desired by the user. Alternatively, the PCIBs of this disclosure may be formed into films having a thickness of from about 0.1 mils to about 5 mils, alternatively from about 0.2 mils to about 1.5 mils, alternatively from about 0.3 mils to about 1.0 mils.

In an embodiment, PCIBs of the type disclosed herein display improvements in processing such that the pressure required to extrude the polymer is reduced when compared to a polymer of the same molecular weight prepared using a metallocene catalyst. For example, the extrusion pressure may be reduced by greater than about 25%, alternatively greater than about 30% or alternatively greater than about 35%.

In an embodiment, films formed from PCIBs of this disclosure may display enhanced barrier properties. For example said films may display reduced moisture vapor transmission rates (MVTR) and reduced oxygen transmission rates (OTR). In an embodiment, film produced from polymers of this disclosure have an MVTR of less than or equal to about 0.5 grams-mil per 100 square inch per day (g-mil/100 in$^2$/day), alternatively, less than or equal to about 0.37 g-mil/100 in$^2$/day, alternatively, less than or equal to about 0.32 g-mil/100 in$^2$/day as measured in accordance with ASTM F 1249. The MVTR measures passage of gaseous $H_2O$ through a barrier. The MVTR may also be referred to as the water vapor transmission rate (WVTR). Typically, the MVTR is measured in a special chamber, divided vertically by the substrate/barrier material. A dry atmosphere is in one chamber, and a moist atmosphere is in the other. A 24-hour test is run to see how much moisture passes through the substrate/barrier from the "wet" chamber to the "dry" chamber under conditions which can specify any one of five combinations of temperature and humidity in the "wet" chamber.

The films produced from PCIBs of this disclosure may be used in the formation of any variety of end-use articles. For example, the polymer may be extruded into a sheet, which is then thermoformed into an end use article such as a container, a cup, a tray, a pallet, a toy, or a component of another product. Other nonlimiting examples of end-use articles which may be produced from the films of this disclosure include merchandise bags, t-shirt bags, trash can liners, grocery sacks, produce bags, food packaging for contents such as cereals, crackers, cheese, meat, etc., shrink wrap and, other items as known to one of ordinary skill in the art. In an embodiment the polymers disclosed herein (e.g., polyethylene) may be formed into films which can be useful in food packaging.

The following are additional enumerated embodiments of the concepts disclosed herein.

A first embodiment which is an imine bis(phenol) compound having Structure I:

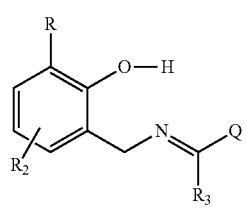

Structure I wherein O and N represent oxygen and nitrogen respectively; R comprises a halogen, a hydrocarbyl group, or a substituted hydrocarbyl group; $R^2$ and $R^3$ can each independently be hydrogen, a halogen, a hydrocarbyl group, or a substituted hydrocarbyl group; and Q is a donor group.

A second embodiment which is a compound of the first embodiment wherein Q has Structure II, Structure III or Structure IV:

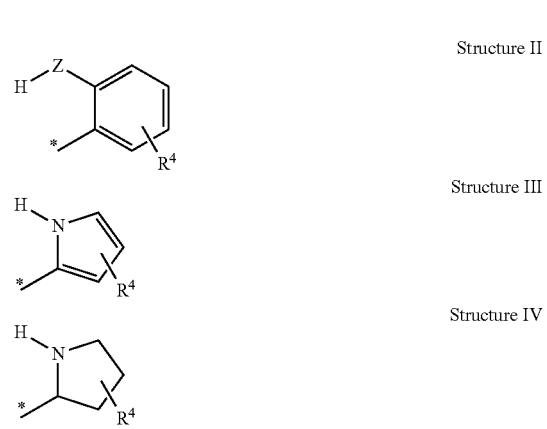

Structure II

Structure III

Structure IV where N represents nitrogen; Z is oxygen or sulfur; and $R^4$ comprises hydrogen, a halogen, a hydrocarbyl group, or a substituted hydrocarbyl group.

A third embodiment which is a compound of any of the first through second embodiments wherein R is a halogen, a $C_1$ to $C_{30}$ alkyl group, a $C_4$ to $C_{30}$ cycloalkyl group, a $C_4$ to $C_{30}$ substituted cycloalkyl group, a $C_3$ to $C_{30}$ aliphatic heterocyclic group, a $C_3$ to $C_{30}$ substituted aliphatic heterocyclic group, a $C_6$ to $C_{30}$ aryl group, a $C_6$ to $C_{30}$ substituted aryl group, a $C_7$ to $C_{30}$ aralkyl group, a $C_7$ to $C_{30}$ substituted aralkyl group, a $C_3$ to $C_{30}$ heteroaryl group, or a $C_3$ to $C_{30}$ substituted heteroaryl group.

A fourth embodiment which is the compound of any of the first through third embodiments wherein $R^2$ and $R^3$ can each independently be a hydrogen, a halogen, a $C_1$ to $C_{30}$ alkyl group, a $C_4$ to $C_{30}$ cycloalkyl group, a $C_4$ to $C_{30}$ substituted cycloalkyl group, a $C_3$ to $C_{30}$ aliphatic heterocyclic group, a $C_3$ to $C_{30}$ substituted aliphatic heterocyclic group, a $C_6$ to $C_{30}$ aryl group, a $C_6$ to $C_{30}$ substituted aryl group, a $C_7$ to $C_{30}$ aralkyl group, a $C_7$ to $C_{30}$ substituted aralkyl group, a $C_3$ to $C_{30}$ heteroaryl group, or a $C_3$ to $C_{30}$ substituted heteroaryl group A fifth embodiment which is the compound of any of the first through fourth embodiments wherein R is a methyl group, an ethyl group, a propyl group, a butyl group, a tert-butyl group, an adamantyl group, a chloride, a bromide, a trifluoro methyl group, a phenyl group, an aryl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, or a nonadecyl group; or alternatively, a methyl group, an ethyl group, a propyl group, a butyl group, a pentyl group, a hexyl group, a heptyl group, an octyl group, a nonyl group, or a decyl group.

A sixth embodiment which is the compound of any of the first through fifth embodiments wherein $R^2$ and $R^3$ can each independently be a hydrogen, methyl group, an ethyl group, a propyl group, a butyl group, a tert-butyl group, an adamantyl group, a tert-amyl, a chloride, a bromide, a trifluoro methyl group, a phenyl group, a aryl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, or a nonadecyl group; or alternatively, a methyl group, an ethyl group, a propyl group, a butyl group, a pentyl group, a hexyl group, a heptyl group, an octyl group, a nonyl group, or a decyl group.

A seventh embodiment which is a metal salt complex of an imine (bis)phenolate compound having Structure V:

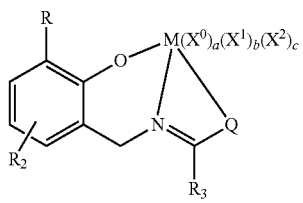

Structure V wherein O and N represent oxygen and nitrogen respectively; R comprises a halogen, a hydrocarbyl group, or a substituted hydrocarbyl group; $R^2$ and $R^3$ can each independently be hydrogen, a halogen, a hydrocarbyl group, or a substituted hydrocarbyl group; Q is a donor group; M is a group III to group 12 transition metal or lanthanide metal having an oxidation state equal to $b+2c+2$; $X^0$ is a neutral ligand; a is 0, 1, or 2; $X^1$ is a monoanionic ligand; b is 0, 1, 2, 3, or 4; $X^2$ is a dianionic ligand; and c is 0, 1, or 2.

An eight embodiment which is the metal salt complex of the seventh embodiment where Q has Structure VI, Structure VII, or Structure VIII:

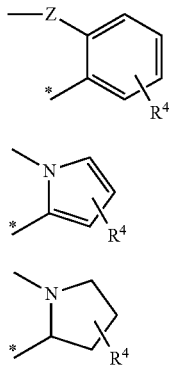

Structure VI

Structure VII

Structure VIII where Z is oxygen or sulfur and Z and N are both bound to M; and $R^4$ comprises hydrogen, a halogen, a hydrocarbyl group, or a substituted hydrocarbyl group.

A ninth embodiment which is the metal salt complex of any of the seventh through eight embodiments wherein $X^0$ comprises an ether, a thioether, an amine, a nitrile, or a phosphine; $X^1$ comprises hydrogen, a halide, a $C_1$ to $C_{18}$ hydrocarbyl group, a hydrocarbyloxide group, a hydrocarbylamino group, a hydrocarbylsilyl group, or hydrocarbylaminosilyl group; and $X^2$ comprises an oxygen atom, $=NR^{2A}$, or $=CR^{2B}R^{2C}$ wherein $R^{2A}$, $R^{2B}$, and $R^{2C}$ are each independently hydrogen or a $C_1$ to $C_{18}$ hydrocarbyl group.

A tenth embodiment which is the compound of any of the seventh through ninth embodiments where Q is Structure II;Z is oxygen; and $R_3$ is hydrogen.

An eleventh embodiment which is the metal salt complex of any of the seventh through tenth embodiments wherein M is titanium, zirconium, or hafnium.

A twelfth embodiment which is the metal salt complex of any of the seventh through eleventh embodiments wherein b is 2 and c is 0.

A thirteenth embodiment which is the metal salt complex of any of the seventh through twelfth embodiments wherein the metal salt complex of an imine (bis)phenolate compound comprises a compound having Structure XIV

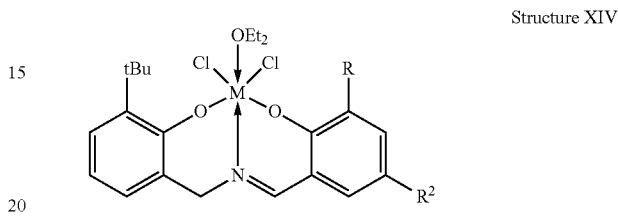

Structure XIV where M is zirconium, or hafnium; and $R^2$ and $R^3$ can each independently be hydrogen, a halogen, a hydrocarbyl group, or a substituted hydrocarbyl group;

A fourteenth embodiment which is the metal salt complex of any of the seventh through thirteenth embodiments wherein the metal salt complex of an imine (bis)phenolate compound comprises a compound having structure X:

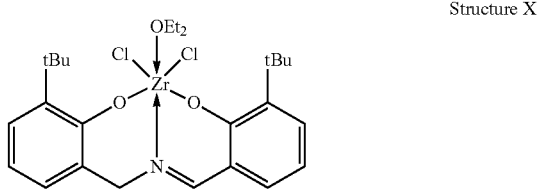

Structure X

A fifteenth embodiment which is a catalyst composition comprising the metal salt complex of an imine (bis)phenolate compound of any of the seventh through fourteenth embodiments and a metal alkyl compound.

A sixteenth embodiment which is the composition of the fifteenth embodiment wherein the metal alkyl compound comprises an organoaluminum compound, an aluminoxane compound, and organoboron or organoborate compound, an ionizing ionic compound, or combinations thereof.

A seventeenth embodiment which is the composition of any of the fifteenth or sixteenth embodiments further comprising an activator-support comprising a solid oxide treated with an electron-withdrawing anion.

An eighteenth embodiment which is the composition of the seventeenth embodiment wherein the solid oxide comprises silica, alumina, silica-alumina, silica-coated alumina, aluminum phosphate, aluminophosphate, heteropolytungstate, titania, zirconia, magnesia, boria, zinc oxide, a mixed oxide thereof, or combinations thereof; and the electron-withdrawing anion comprises sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, or combinations thereof.

A nineteenth embodiment which is the composition of any of the fifteenth through eighteenth embodiments wherein the metal alkyl comprises trialkylaluminum, an alkylaluminum halide, an alkylaluminum alkoxide, an aluminoxane, or combinations thereof.

A twentieth embodiment which is the composition of any of the fifteenth through eighteenth embodiments wherein the metal alkyl comprises methyl lithium, n-butyl lithium, sec-butyl lithium, tert-butyl lithium, diethyl magnesium, di-n-butylmagnesium, ethylmagnesium chloride, n-butylmagnesium chloride, diethyl zinc, trimethylaluminum, triethylaluminum, tripropylaluminum, tributylaluminum, trihexylaluminum, trioctylaluminum, diethylaluminum chloride, diethylaluminum bromide, ethylaluminum dichloride, ethylaluminum sesquichloride, methylaluminoxane (MAO), ethylaluminoxane, modified methylaluminoxane (MMAO), n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neo-pentylaluminoxane, or combinations thereof.

A twenty-first embodiment which is an olefin polymerization process comprising contacting the catalyst composition of any of the fifteenth through eighteenth embodiments with an olefin monomer and optionally an olefin comonomer under conditions suitable for the formation of a polymer; and recovering the polymer.

A twenty-second embodiment which is a method comprising contacting a catalyst composition with a monomer under conditions suitable for the formation of a polymer wherein the catalyst composition comprises a metal salt complex of an imine (bis)phenolate compound, a solid oxide, and an optional metal alkyl and wherein the metal salt complex of an imine (bis)phenolate compound has Structure XIV:

Structure XIV

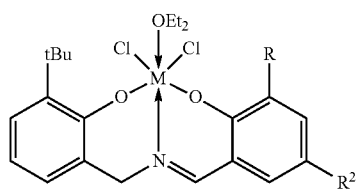

where M is titanium, zirconium, or hafnium; $OEt_2$ is ethoxide; R comprises a halogen, a hydrocarbyl group, or a substituted hydrocarbyl group; and $R^2$ comprises hydrogen, a halogen, a hydrocarbyl group, or a substituted hydrocarbyl group.

A twenty-third embodiment which is the method of the method of any of the twenty-first through twenty-second embodiments wherein the monomer comprises ethylene and the polymer comprises polyethylene.

EXAMPLES

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can suggest themselves to one of ordinary skill in the art without departing from the spirit of the present invention or the scope of the appended claims.

The data and descriptions provided in the following examples are given to show particular aspects and embodiments of the compounds, catalyst systems, and olefin oligomerization and/or olefin polymerization methods disclosed, and to demonstrate a number of the practices and advantages thereof. The examples are given as a more detailed demonstration of some of the aspects and embodiments described herein and are not intended to limit the disclosure or claims in any manner.

Melt index (MI, g/10 min) was determined in accordance with ASTM D 1238 condition E at 190° C. with a 2160 gram weight.

High load melt index (HLMI, g/10 min) was determined in accordance with ASTM D 1238 condition E at 190° C. with a 21,600 gram weight.

Polymer density was determined in grams per cubic centimeter (g/cc) on a compression molded sample, cooled at about 15° C. per hour, and conditioned for about 40 hours at room temperature in accordance with ASTM D 1505 and ASTM D 1928, procedure C.

Molecular weight and molecular weight distributions were obtained using a PL-GPC 220 (Polymer Labs, an Agilent Company) system equipped with a IR4 detector (Polymer Char, Spain) and three Styragel HMW-6E GPC columns (Waters, Mass.) running at 145° C. The flow rate of the mobile phase 1,2,4-trichlorobenzene (TCB) that contains 0.5 g/L 2,6-di-t-butyl-4-methylphenol (BHT) was set at 1 mL/min and the concentration of polymer solutions was generally kept in the range of 1.0-1.5 mg/mL, depending on the molecular weight. Sample preparation was conducted at 150° C. for nominally 4 h with occasional and gentle agitation before the solutions being transferred to sample vials for injection. The integral calibration method was used to deduce molecular weights and molecular weight distributions using a Chevron Phillips Chemicals Company's HDPE polyethylene resin, MARLEX BHB5003, as the broad standard. The integral table of the broad standard was pre-determined in a separate experiment with SEC-MALS.

Rheology measurements were made as follows: Strains were generally maintained at a single value throughout a frequency sweep, but larger strain values were used for low viscosity samples to maintain a measurable torque. Smaller strain values were used for high viscosity samples to avoid overloading the torque transducer and to keep within the linear viscoelastic limits of the sample. The instrument automatically reduces the strain at high frequencies if necessary to keep from overloading the torque transducer. These data were fit to the Carreau-Yasuda equation to determine zero shear viscosity ($\eta_0$), relaxation time ($\tau$), and a measure of the breadth of the relaxation time distribution (CY-a).

MVTR was measured in accordance with ASTM F 1249.

Synthesis of Imine Phenol Ligands

Two separate classes of imine phenol ligands incorporating a donor arm were prepared. The first class utilized a second phenol as the donor arm giving formally an imine (bis)phenolate ligand scaffold. The ligands were prepared via the reaction of benzyl amine phenols and aldehydes, as shown in Scheme I. Typically, one equivalent of 3-tert-butyl-2-hydroxybenzylamine was added to one equivalent of 3-tert-butyl-2-hydrozybenzaldehyde to yield ($^t$Bu)LH$_2$ as confirmed by NMR spectroscopy.

Scheme I.

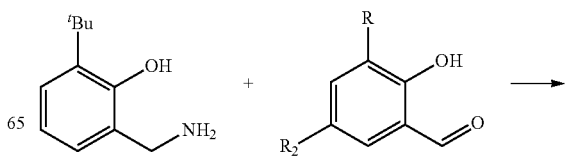

-continued

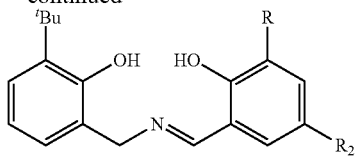

(tBu)LH₂; R = tBu, R₂ = H
(tBu)₂LH₂; R = tBu, R₂ = tBu
(Me)LH₂; R = Me, R₂ = H
(Cl)₂LH₂; R = Cl, R₂ = Cl
(H)LH₂; R = H, R₂ = H
(OMe)LH₂; R = OMe, R₂ = H
(Ad)(Me)LH₂; R = Ad, R₂ = Me

The synthesis of three imine bis(phenolate) ligands was carried out as follows: (tBu)LH₂: To 3-tert-butyl-2-hydroxybenzylamine (0.816 g, 4.55 mmol) and 3-tert-butyl-2-hydroxybenzaldehyde (0.788 g, 4.42 mmol) was added 30 mL EtOH forming a yellow solution. The mixture was heated to 85° C. for 3 h. The volatiles were evacuated leaving (tBu)LH₂. $^1$H NMR (CDCl₃): δ 8.47 (1H), δ 7.36 (1H), δ 7.29 (1H), δ 7.13 (1H), δ 7.09 (1H), δ 6.89 (1H), δ 6.85 (1H), δ 5.72 (1H), δ 4.84 (2H), δ 1.46 (9H), δ 1.44 (9H). (tBu)₂LH₂. To 3-tert-butyl-2-hydroxybenzylamine (0.456 g, 2.54 mmol) and 3,5-di-tert-butyl-2-hydroxybenzaldehyde (0.567 g, 2.42 mmol) was added 15 mL EtOH forming a yellow solution. The mixture was heated to 85° C. for 5 h. The volatiles were evacuated leaving (tBu)₂LH₂ in quantitative yield which was used without further purification. $^1$H NMR (CDCl₃): δ 8.49 (1H), δ 7.43 (1H), δ 7.28 (1H), δ 7.13 (1H), δ 7.08 (1H), δ 6.88 (1H), δ 5.84 (1H), δ 4.83 (2H), δ 1.44 (18H), δ 1.31 (9H).

(Me)LH₂. To 3-tert-butyl-2-hydroxybenzylamine (0.315 g, 1.76 mmol) and 2-hydroxy-3-methylbenzaldehyde (0.222 g, 1.63 mmol) was added 10 mL EtOH forming a yellow solution. The mixture was heated to 85° C. for 2 h. The volatiles were evacuated leaving (Me)LH₂ in quantitative yield which was used without further purification. $^1$H NMR (CDCl₃): δ 12.70 (1H), δ 8.46 (1H), δ 7.27 (1H), δ 7.24 (1H), δ 7.08 (1H), δ 6.87 (1H), δ 6.82 (1H), δ 5.72 (1H), δ 4.84 (2H), δ 2.29 (3H), δ 1.44 (9H).

The second class utilized pyrrole donor groups and were prepared from the condensation of hydrozybenzylamine and a pyrrole aldehyde as shown in Scheme II. This synthetic route was use for the preparation of PyLH₂ and $^{Me}$PyLH₂.

Scheme II

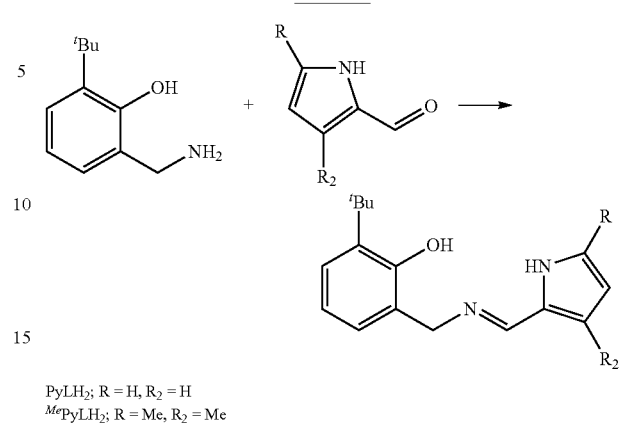

PyLH₂; R = H, R₂ = H
$^{Me}$PyLH₂; R = Me, R₂ = Me

PyLH₂: To 3-tert-butyl-2-hydroxybenzylamine (0.30 g, 1.67 mmol) and pyrrole-2-carboxaldehyde (0.158 g, 1.67 mmol) was added 10 mL EtOH forming a yellow solution. The mixture was heated to 85° C. for 2 h. The volatiles were evacuated leaving PyLH₂. $^1$H NMR (CDCl₃): δ 9.1 (1H), δ 8.12 (1H), δ 7.22 (1H), δ 6.97 (1H), δ 6.93 (1H), δ 6.80 (1H), δ 6.60 (1H), δ 6.28 (1H), δ 4.83 (s, 2H), δ 1.46 (9H).

Metal Complexation of the Imine Bis(Phenol) Ligands

A transition metal complex of the type disclosed herein can be formed in two ways. Treatment of (tBu)LH₂ to 1 equivalent of ZrBn₄ gives a 50:50 mixture of ((tBu)L)₂Zr and ZrBn₄ failing to give the desired monoligated (tBu)LZrBn₂. Treatment of (tBu)LH₂ with Zr(NEt₂)₄ also yields the undesired diligated ((tBu)L)₂Zr. However the desired monoligated complex was ((tBu)LZrCl₂(Et₂O)) by the disproportionation of ((tBu)L)₂Zr with ZrCl₄(THF)₂ (Method A). Conversely, (tBu)LLZrCl₂(Et₂O) was prepared by the addition of (tBu)LH₂ to a mixture of ZrCl₄/2BzMgCl in the presence of Et₂O (Method B). The product formed, (tBu)LZrCl₂(Et₂O) was confirmed by NMR spectroscopy. The reactions are summarized in Scheme III.

Scheme III

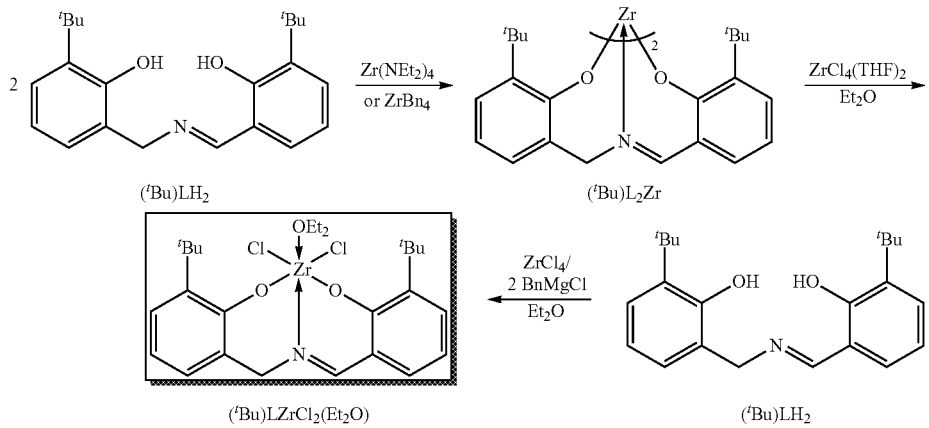

(tBu)LZrCl₂(OEt₂). Method A: (tBu)LH₂ (0.11 g, 0.324 mmol) and Zr(NEt₂)₄ (0.062 g, 0.162 mmol) were combined in 3 mL PhMe forming a yellow solution. The mixture was stirred overnight at ambient temperature. The volatiles were evacuated leaving an orange-yellow solid which was dissolved in $Et_2O$ (7 mL), and cooled to −30° C. The cold solution was added to $ZrCl_4 \cdot 2THF$ (0.055 g, 0.147 mmol) suspended in 5 mL $Et_2O$. The suspension was allowed to warm with stirring to ambient temperature overnight. The volatiles were evacuated and the resulting solid was washed with pentane leaving (tBu)LZrCl$_2$(OEt$_2$) as an off-white solid (0.87 g).

Method B:

ZrCl$_4$ (1.47 g, 6.31 mmol) was suspended in Et$_2$O (35 mL) and cooled to −30° C. In the dark, 1 M BnMgCl in Et$_2$O (12.6 mL, 12.6 mmol) was added. The resulting suspension was allowed to warm to ambient temperature with stirring overnight. The volatiles were evacuated and the residue was extracted with 35 mL PhMe. The PhMe extract was added to (tBu)LH$_2$ (2.04 g, 6.01 mmol) which causes a precipitate to form. The mixture was allowed to stand at ambient temperature for three days. The pale yellow precipitate was filtered and washed with 4×5 mL pentane leaving (tBu)LZrCl$_2$(OEt$_2$) (1.45 g). $^1$H NMR (CD$_2$Cl$_2$): δ 8.49 (s, 1H), δ 7.61 (d, 1H), δ 7.34 (d, 2H), δ 7.09 (d, 1H), δ 6.98 (t, 1H), δ 6.83 (t, 1H), δ 4.79 (s, 2H), δ 4.07 (q, 4H), δ 1.51 (s, 9H), δ 1.50 (s, 9H), δ 1.23 (t, 6H). An NMR spectra of the product is presented in FIG. 1.

A series of zirconium and hafnium complexes were prepared as described in Scheme IV using method B.

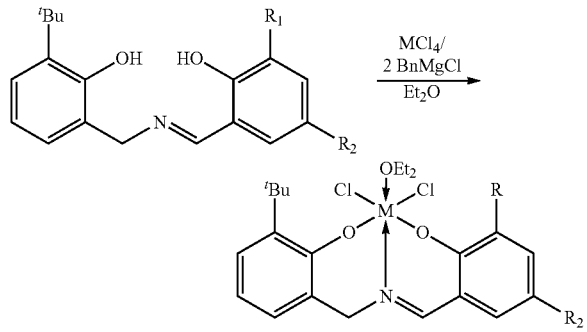

Scheme IV (tBu)LHfCl$_2$(Et$_2$O); R = tBu, R$_2$ = Me
(tBu)$_2$LZrCl$_2$(Et$_2$O); R = tBu, R$_2$ = tBu
(Me)LZrCl$_2$(Et$_2$O); R = Me, R$_2$ = Me
(Cl)$_2$LZrCl$_2$(Et$_2$O); R = Cl, R$_2$ = Cl
(Ad)(Me)LZrCl$_2$(Et$_2$O); R = Ad, R$_2$ = Me (tBu)LHfCl$_2$(OEt$_2$). Method B: HfCl$_4$ (0.233 g, 0.728 mmol) was suspended in Et$_2$O (6 mL) and cooled to −30° C. In the dark, 1 M BnMgCl in Et$_2$O (1.46 mL, 1.46 mmol) was added. The resulting suspension was allowed to warm to ambient temperature with stirring overnight. The volatiles were evacuated and the residue was extracted with 8 mL PhMe. The PhMe extract was added to (tBu)LH$_2$ (0.235 g, 0.693 mmol) which causes a precipitate to form. The mixture was allowed to stand at ambient temperature for three days. The suspension was evacuated to have volume and 10 mL heptane was added. The solution was decanted and the solid washed with heptane (10 mL) leaving pale yellow (tBu)LHfCl$_2$(OEt$_2$) (0.22 g). $^1$H NMR (CD$_2$Cl$_2$): δ 8.48 (1H), δ 7.63 (1H), δ 7.34 (2H), δ 7.08 (1H), δ 6.94 (1H), δ 6.80 (1H), δ 4.81 (2H), δ 4.0 (4H), δ 1.50 (9H), δ 1.49 (9H), δ 1.23 (6H).

(tBu)$_2$LZrCl$_2$(OEt$_2$). Method B: ZrCl$_4$ (0.775 g, 3.33 mmol) was suspended in Et$_2$O (20 mL) and cooled to −30° C. In the dark, 1 M BnMgCl in Et$_2$O (6.66 mL, 6.66 mmol) was added. The resulting suspension was allowed to warm to ambient temperature with stirring overnight. The volatiles were evacuated and the residue was extracted with 20 mL PhMe. The PhMe extract was added to (tBu)$_2$LH$_2$ (1.25 g, 3.17 mmol) which caused a orange-yellow solution to form. The mixture was allowed to stand at ambient temperature for three days. The solution was evacuated to ¼ volume, 25 mL heptanes was added, and the solution was cooled to −30° C. causing a solid to form. The solution was decanted and the solid washed with 3×5 mL heptane leaving a pale yellow solid (tBu)$_2$LZrCl$_2$(OEt$_2$) (0.5 g). $^1$H NMR (CD$_2$Cl$_2$): δ 8.53 (1H), δ 7.63 (1H), δ 7.36 (1H), δ 7.23 (1H), δ 7.03 (1H), δ 6.84 (1H), δ 5.04 (2H), δ 4.14 (4H), δ 1.44 (18H), δ 1.30 (9H), 1.2 (6H).

(Me)LZrCl$_2$(OEt$_2$). Method B: ZrCl$_4$ (0.242 g, 1.04 mmol) was suspended in Et$_2$O (9 mL) and cooled to −30° C. In the dark, 1 M BnMgCl in Et$_2$O (2.1 mL, 2.1 mmol) was added. The resulting suspension was allowed to warm to ambient temperature with stirring overnight. The volatiles were evacuated and the residue was extracted with 10 mL PhMe. The PhMe extract was added to (Me)LH$_2$ (0.294 g, 0.99 mmol) which caused a precipitate to form. The mixture was allowed to stand at ambient temperature for three days. The solution was decanted and the solid washed with 2×5 mL heptane leaving a pale yellow solid (Me)LZrCl$_2$(OEt$_2$) (0.23 g). $^1$H NMR (CD$_2$Cl$_2$): δ 8.48 (1H), δ 7.45 (1H), δ 7.31 (2H), δ 7.08 (1H), δ 6.93 (1H), δ 6.83 (1H), δ 4.82 (2H), δ 3.84 (4H), δ 2.32 (3H), δ 1.50 (9H), δ 1.15 (6H).

Olefin Polymerizations

The ability of catalyst compositions of the type disclosed herein to catalyze olefin polymerization reactions were investigated. Specifically, (tBu)LZrCl$_2$(Et$_2$O) was used to catalyze ethylene polymerization in the presence of S-SSA. The reaction conditions are presented in Table 1. The reactions utilized 3 milligrams of (tBu)LZrCl$_2$(Et$_2$O) designated catalyst A, (tBu)LHfCl$_2$(Et$_2$O) designated catalyst B, (Me)LZrCl$_2$(Et$_2$O), designated catalyst C, (tBu)$_2$LZrCl$_2$(Et$_2$O) designated catalyst D, Cl$_2$LZrCl$_2$(Et$_2$O) designated Catalyst E, or (Ad)(Me)LZrCl$_2$(Et$_2$O) designated Catalyst F. Each reaction contained 0.6 ml of TIBA, and 1 gram of S-SSA and was run at a temperature of 90° C. under a pressure of 420 psig for 45 minutes.

TABLE I

| Sample No. | Catalyst | Co-catalyst | Temperature (° C.) | Pressure (psig) | 1-hexene (mL) | H$_2$ (PPM feed) [mole] | Time (min) | Solid PE (g) | Catalyst Activity (kg PE/g cat · h) | M$_w$ (kg/mol) |
|---|---|---|---|---|---|---|---|---|---|---|
| 1 | A | 0.6 mL 1M TIBA/1 g S-SSA | 90 | 420 | 0 | 0 | 45 | 282 | 125.3 | 366.9 |
| 2 | A | 0.6 mL 1M TIBA/1 g S-SSA | 90 | 420 | 0 | 200 | 45 | 273 | 121.3 | 298.1 |
| 3 | A | 0.6 mL 1M TIBA/1 g S-SSA | 90 | 420 | 0 | 325 | 45 | 277 | 123.1 | 266.5 |
| 4 | A | 0.6 mL 1M TIBA/1 g S-SSA | 90 | 420 | 0 | 1000 | 45 | 255 | 113.3 | 201.1 |

TABLE I-continued

| Sample No. | Catalyst | Co-catalyst | Temperature (°C.) | Pressure (psig) | 1-hexene (mL) | H₂ (PPM feed) [mole] | Time (min) | Solid PE (g) | Catalyst Activity (kg PE/g cat · h) | $M_w$ (kg/mol) |
|---|---|---|---|---|---|---|---|---|---|---|
| 5 | A | 0.6 mL 1M TIBA/1 g S-SSA | 90 | 420 | 0 | 2000 | 45 | 252 | 112 | 175.7 |
| 6 | A | 0.6 mL 1M TIBA/1 g S-SSA | 90 | 420 | 0 | [0.21] | 45 | 152 | 67.6 | 155.0 |
| 7 | A | 0.6 mL 1M TIBA/1 g S-SSA | 90 | 420 | 0 | [0.28] | 45 | 121 | 53.8 | 117.7 |
| 8 | A | 0.6 mL 1M TIBA/1 g S-SSA | 90 | 420 | 10 | 325 | 45 | 242 | 107.6 | 300.0 |
| 9 | B | 0.6 mL 1M TIBA/1 g S-SSA | 90 | 420 | 0 | 0 | 45 | 41 | 18.2 | 850.0 |
| 10 | C | 0.6 mL 1M TIBA/1 g S-SSA | 90 | 420 | 0 | 0 | 45 | 36 | 16 | 564.0 |
| 11 | D | 0.6 mL 1M TIBA/1 g S-SSA | 90 | 420 | 0 | 0 | 45 | 199 | 88.4 | 532.0 |
| 12 | E | 0.6 mL 1M TIBA/1 g S-SSA | 90 | 420 | 0 | 0 | 45 | 75 | 33.3 | 439.0 |
| 13 | F | 0.6 mL 1M TIBA/1 g S-SSA | 90 | 420 | 0 | 0 | 45 | 326 | 144.9 | 458 |

The results demonstrate the ligand substitution influences the catalyst's activity as replacement of one of the tert-butyl groups with a methyl groups resulted in a dramatic decrease in the catalytic activity. Furthermore, the inclusion of additional ancillary bulk via an adamantyl group (catalyst F) caused the activity to increase. Additionally, catalyst A which contained zirconium gave higher catalytic activities when compared to the corresponding complex with hafnium, catalyst B.

Various properties of the polymer samples obtained are presented in Table II. The polymer samples are designated Sample numbers 1, 2, 3, 4, 5, 6, 7, and 8 corresponding to reaction numbers 1, 2, 3, 4, 5, 6, 7, and 8 of Table 1.

TABLE II

| Sample No. | HLMI | $M_n$ (×1000 g/mol) | $M_w$ (×1000 g/mol) | $M_z$ (×1000 g/mol) | $M_w/M_n$ | Density (g/cc) |
|---|---|---|---|---|---|---|
| 1 | 1.1 | 9.7 | 366.9 | 2296.1 | 37.8 | 0.964 |
| 2 | 3.7 | 8.3 | 298.1 | 1894.2 | 35.8 | 0.965 |
| 3 | 7.2 | 8.5 | 266.5 | 1767.0 | 31.2 | 0.966 |
| 4 | 17.2 | 7.5 | 201.1 | 1255.0 | 27.0 | 0.967 |
| 5 | 30.2 | 7.4 | 175.7 | 1288.1 | 23.6 | 0.968 |
| 6 | 66.2 | 8.5 | 155.0 | 1647.2 | 18.3 | 0.971 |
| 7 | 153.9 | 6.6 | 117.7 | 1279.8 | 18.0 | 0.973 |
| 8 | 4.8 | 8.2 | 300.6 | 2002 | 36.6 | 0.965 |

The results demonstrate the molecular weight distributions of the polyethylene resins produced using catalyst compositions of the type disclosed herein are broad. Further the introduction of hydrogen resulted in an increase in the high load melt index (HLMI), a decrease in the molecular weight and a narrowing of the molecular weight distribution. The introduction of 1-hexene did not appear to cause a significant effect on the resin distribution or density.

Example 2

As can be seen in Table I, the polymer samples were prepared at 90° C. at a pressure of 420 psig in the presence of hydrogen. The concentration of hydrogen in samples 2-5 and 8 was supplied in a feed. The hydrogen addition for samples 6 and 7 was provided at the onset of polymer preparation, which is indicated as a value in brackets in Table III. Samples 1-5 indicate a decrease with $M_w$ as the concentration of hydrogen in the feed increased. As can be seen, the $M_w$ for samples 9-13 is greater than the $M_w$ for samples 1-8.

Various polymer properties were assessed for Samples 1-8, and the results are presented in Table III. Of note are the densities of samples 1-8, which are greater than about 0.964 g/cc and as high as about 0.973 g/cc for an HLMI range of about 1.1 dg/min. to about 153.85 dg/min.

TABLE III

| Sample No. | 1 | 2 | 3 | 4 | 5 | 6 | 7 | 8 |
|---|---|---|---|---|---|---|---|---|
| Density (g/cc) | 0.964 | 0.965 | 0.966 | 0.967 | 0.968 | 0.971 | 0.973 | 0.965 |
| Melt Index | n/a | n/a | n/a | n/a | 0.33 | 0.95 | 2.84 | n/a |
| HLMI | 1.1 | 3.7 | 7.2 | 17.2 | 30.9 | 66.2 | 153.9 | 4.8 |
| $M_n$ (kg/mol) | 9.7 | 8.3 | 8.5 | 7.5 | 7.4 | 8.5 | 6.6 | 8.2 |
| $M_w$ (kg/mol) | 366.9 | 298.1 | 266.5 | 201.1 | 175.7 | 155.0 | 117.7 | 300.6 |
| $M_z$ (kg/mol) | 2296.1 | 1894.2 | 1767.0 | 1255.0 | 1288.1 | 1647.2 | 1280.0 | 2002.0 |
| $M_w/M_n$ | 37.8 | 35.8 | 31.2 | 27.0 | 23.6 | 18.3 | 18.0 | 36.6 |
| $\eta_0$ (Pa-s) | 5.7E+07 | 2.7E+07 | 5.3E+06 | 7.1E+05 | 2.4E+05 | 6.1E+04 | 1.5E+04 | 2.1E+07 |
| CY-a | 0.220 | 0.187 | 0.188 | 0.195 | 0.199 | 0.210 | 0.211 | 0.179 |

Comparative Example 1

The properties of commercial polymers were compared to polymers of the type disclosed herein. Nine comparative polymer samples, designated C1-C9 were investigated. C1-C4 and C5 are prepared from Cr/SiO2 and Ziegler-Natta catalysts, respectively. The metallocene polymers used as comparisons in film applications (C6-C9) were prepared as described in Table V using metallocene catalysts MTE-A or MTE-B which are depicted below. The metallocene polymers designated MTE1-MTE11 are as described in U.S. Patent Publication No. 20110035193 which is incorporated by reference herein in its entirety.

TABLE IV

| Comparative Sample No. | Resin Type |
|---|---|
| C1 | MARLEX K605 |
| C2 | MARLEX EHM 6004 |
| C3 | MARLEX EHM 6007 |
| C4 | MARFLEX 9659 |
| C5 | LBI M6210 |
| C6 | Metallocene (MTE-A) |
| C7 | Metallocene (MTE-A) |
| C8 | Metallocene (MTE-B) |
| C9 | Metallocene (MTE-B) |
| MTE1 | Metallocene |
| MTE2 | Metallocene |
| MTE3 | Metallocene |
| MTE4 | Metallocene |
| MTE5 | Metallocene |
| MTE6 | Metallocene |
| MTE7 | Metallocene |
| MTE8 | Metallocene |
| MTE9 | Metallocene |
| MTE10 | Metallocene |
| MTE11 | Metallocene |

TABLE V

| Sample No. | Catalyst | Co-catalyst | Temperature (°C.) | Pressure (psig) | $H_2$ (PPM feed) | Time (min) | Solid PE (g) |
|---|---|---|---|---|---|---|---|
| C6 | 3 mg MTE-A | 0.6 mL 1M TIBA/0.2 g S-SSA | 90 | 390 | 125 | 41 | 306 |
| C7 | 3 mg MTE-A | 0.6 mL 1M TIBA/0.2 g S-SSA | 90 | 390 | 115 | 42 | 305 |
| C8 | 1 mg MTE-B | 0.5 mL 1M TIBA/0.1 g S-SSA | 95 | 420 | 200 | 30 | 259 |
| C9 | 0.3 mg MTE-B | 0.5 mL 1M TIBA/0.1 g M-SSA | 95 | 420 | 0 | 30 | 313 |

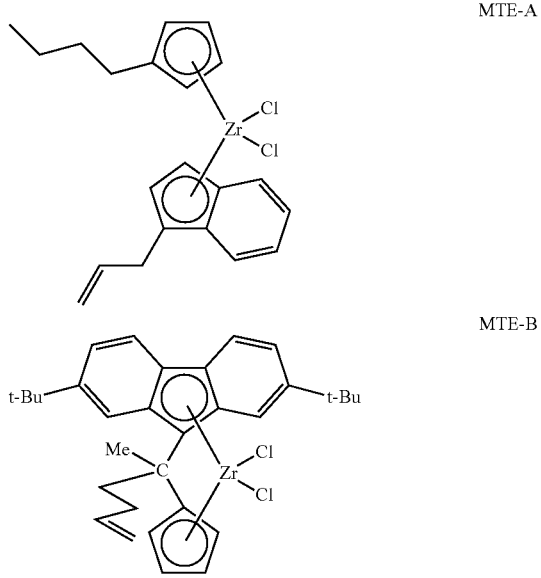

The density, MI and HLMI of the comparative samples are presented in Tables VI and VII.

TABLE VI

| | Comparative Sample No. | | | | | | | | |
|---|---|---|---|---|---|---|---|---|---|
| | C1 | C2 | C3 | C4 | C5 | C6 | C7 | C8 | C9 |
| Density (g/cc) | 0.961 | 0.963 | 0.964 | 0.962 | 0.958 | 0.962 | 0.963 | 0.949 | 0.942 |
| Melt Index | n/a | 0.37 | 0.7 | 1 | 1 | 1.9 | 1.2 | 0.2 | n/a |
| HLMI | 11 | n/a | n/a | n/a | n/a | n/a | n/a | 6.9 | 1.4 |

TABLE VII

| | Comparative Sample No. | | | | | | | | | | |
|---|---|---|---|---|---|---|---|---|---|---|---|
| | MTE1 | MTE2 | MTE3 | MTE4 | MTE5 | MTE6 | MTE7 | MTE8 | MTE9 | MTE10 | MTE11 |
| Density (g/cc) | 0.938 | 0.944 | 0.947 | 0.951 | 0.950 | 0.955 | 0.964 | 0.969 | 0.973 | 0.975 | 0.976 |
| $M_w$ (kg/mol) | 750 | 368 | 283 | 201 | 193 | 135 | 70 | 51 | 35 | 25 | 20 |

Figure 2:
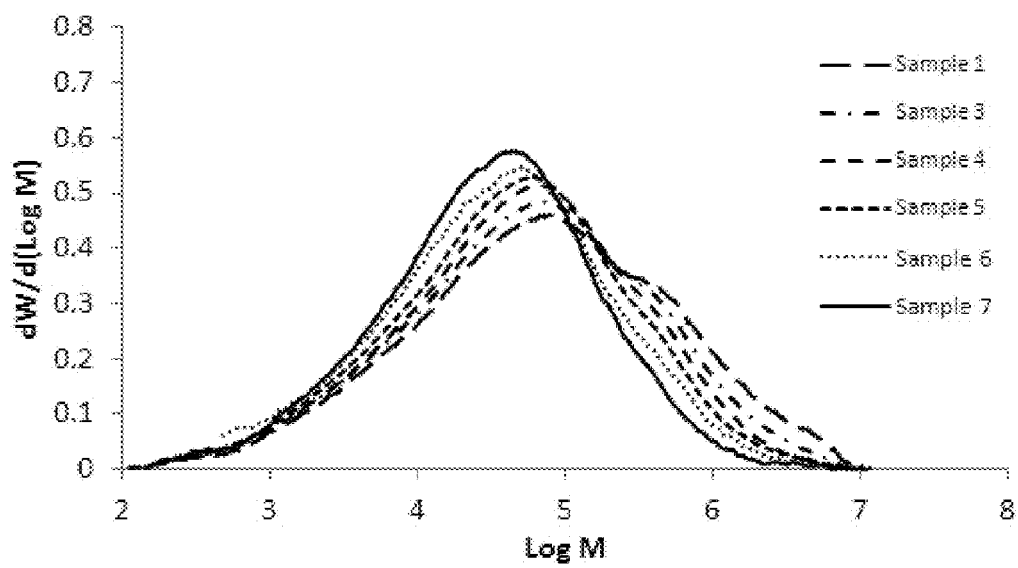
FIGS. 2-4 are molecular weight distribution profiles for samples from Example 2.
Figure 3:
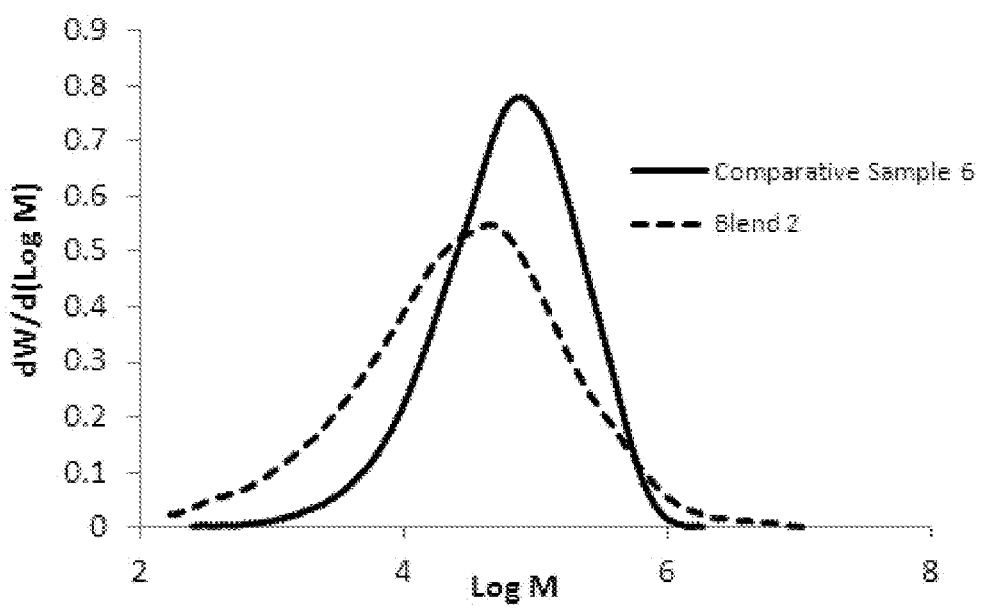
Figure 4:
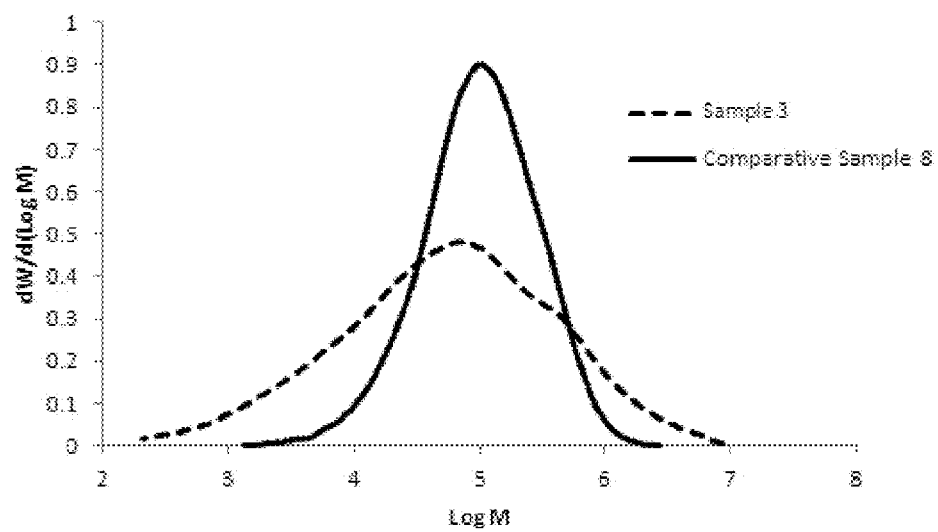

A comparison of the MI, HLMI and density for the polymers from example 2 and the comparative polymers is presented in Table VIII. FIGS. 2-4 are plots of the MWD for various polymer samples and comparative polymer samples. The comparisons show that the polymer compositions of this disclosure are greater in density than resins commercially prepared from heterogenous chromium, Ziegler-Natta, and/or metallocene catalysts. This is true across a wide range of melt and high load melt indices.

TABLE VIII

| Sample No. | MI | HLMI | Density (g/cc) |
|---|---|---|---|
| 3 | | 7.2 | 0.966 |
| C1 | | 11 | 0.961 |
| 4 | | 17.2 | 0.967 |
| 5 | 0.33 | 30.2 | 0.968 |
| C2 | 0.37 | | 0.963 |
| C3 | 0.7 | | 0.964 |
| 6 | 0.95 | 66.18 | 0.971 |
| C4 | 1 | | 0.962 |
| C5 | 1 | | 0.958 |
| C7 | 1.2 | | 0.963 |

The results also demonstrate the polymers of the present disclosure have a higher density for a given melt index (MI). Table VIII shows four groups of polymers for comparison of density for a given MI. The first group compares samples 8 and 9 with C1. The polymer of sample 3 has a HLMI of about 7.2 dg/min. and a density of about 0.966 g/cc, and the polymer of sample 4 has a HLMI of about 17.2 dg/min. and a density of about 0.967 g/cc. In contrast, the polymer of C1 has a HLMI of 11 dg/min. and a density of 0.961 g/cc. The data in Table VIII shows polymers prepared in accordance with the present disclosure, when having the same HLMI value (e.g., 11) as C1, have a higher density, e.g., between about 0.966 g/cc and about 0.967 g/cc. The second group compares sample 5 with samples C2 and C3. Comparing sample 5 with comparative sample 2 shows the polymer of sample 10 has a MI of 0.33 dg/min. and a density of 0.968 g/cc, while the comparative polymer of sample C2 has a similar MI of 0.37 dg/min. and a density of 0.963 g/cc. Comparing sample 5 with comparative sample C3 shows the polymer of sample 10 has a higher density even than that of comparative sample C3 having a higher MI of 0.7 dg/min. Finally, the fourth group compares sample 6 with comparative samples C4, C5, and C7. Comparing sample 6 with comparative polymers C4, C5, and C7 having similar MI values shows the polymer of sample 6 has a higher density than any of the polymers prepared with metallocene, Ziegler (LBI M6210), and Cr/SiO$_2$ catalysts (MARFLEX 9659.

Figure 5:
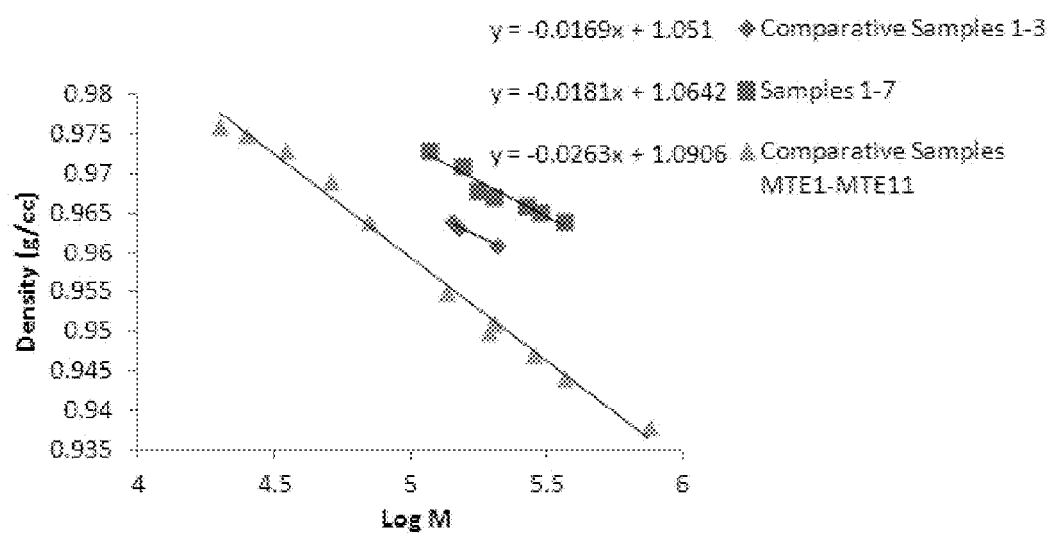
FIG. 5 is a plot of the density as a function of molecular weight for the samples from Example 2.

These results are depicted in FIG. 5 which is a graph of three groups of polymer samples as a function of the log of the molecular weight. Referring to FIG. 5, comparative polymer samples 1-3 formed a first group, comparative samples MTE1-MTE11 formed a second group while the polymers of this disclosure, Samples 1-7, formed a third group. Notably for a given molecular weight, the polymers of this disclosure displayed a higher density than any of the comparative samples investigated. The results also demonstrate the polymers of the present disclosure have a broad molecular weight distribution. In Table IX, it can be seen that samples 1, 3, 5, and 7 have broader molecular weight distributions than the polymers of comparative samples prepared with metallocene catalysts, namely samples C6, C8, and C9.

TABLE IX

| Sample No. | HLMI [MI] | $M_n$ (kg/mol) | $M_w$ (kg/mol) | $M_z$ (kg/mol) | $M_w/M_n$ | $M_z/M_n$ | $\eta_0$ (Pa-s) | CY-a |
|---|---|---|---|---|---|---|---|---|
| 1 | 1.1 | 9.7 | 366.9 | 2296.1 | 37.8 | 6.3 | 5.7E+07 | 0.220 |
| C9 | 1.4 | 95.3 | 237.6 | 440.5 | 2.5 | 1.9 | 7.6E+04 | 0.453 |
| 3 | 7.2 | 8.5 | 266.5 | 1767.0 | 31.2 | 6.6 | 5.3E+06 | 0.188 |
| C8 | 6.9 | 53.1 | 165.6 | 383.8 | 3.1 | 2.3 | 2.8E+04 | 0.356 |
| 5 | 30.9 | 7.4 | 175.7 | 1288.1 | 23.6 | 7.3 | 2.4E+05 | 0.199 |
| 6 | [0.95] | 8.5 | 155.0 | 1647.2 | 18.3 | 10.6 | 6.1E+04 | 0.210 |
| C7 | [1.2] | 19.5 | 124.6 | 296.6 | 6.4 | 2.4 | 7.2E+03 | 0.503 |
| 7 | [2.84] | 6.6 | 117.7 | 1280.0 | 18.0 | 10.9 | 1.5E+04 | 0.211 |
| C6 | [1.9] | 20.8 | 112.9 | 286.0 | 5.4 | 2.5 | 4.5E+03 | 0.498 |

Table IX additionally highlights the improvements of the samples of the polymer of the present disclosure over comparative samples regarding molecular weight distribution and $\eta_0$ for given HLMI values. Particularly, for HLMI values of 1.1 dg/min, for sample 1 and 1.4 dg/min, for comparative sample C9, the $M_z$ value is much greater for sample 1 compared to comparative sample C9. Likewise is true for samples 3 and 5 compared to comparative sample C8. For sample 1, the $\eta_0$ is 5.7E+07 compared to the much lower value of 7.7E+04 for comparative sample C9. For samples 3 and 5, the $\eta_0$ values are 5.3E+06 and 2.4E+05 compared to a value of 2.8E+04 for comparative sample C8. Samples 1, 3, 5, and 7 in Table XII show as HLMI increases, the $M_z$ and $\eta_0$ values decrease.

Figure 6:
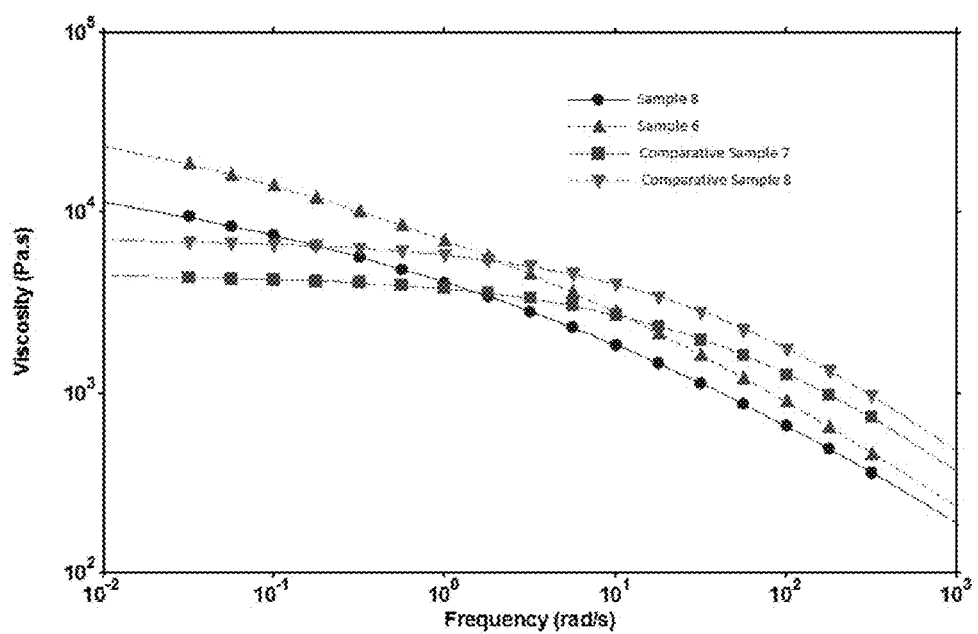
FIGS. 6-7 are plots of the dynamic viscosity as a function of frequency for samples from Example 2.
Figure 7:
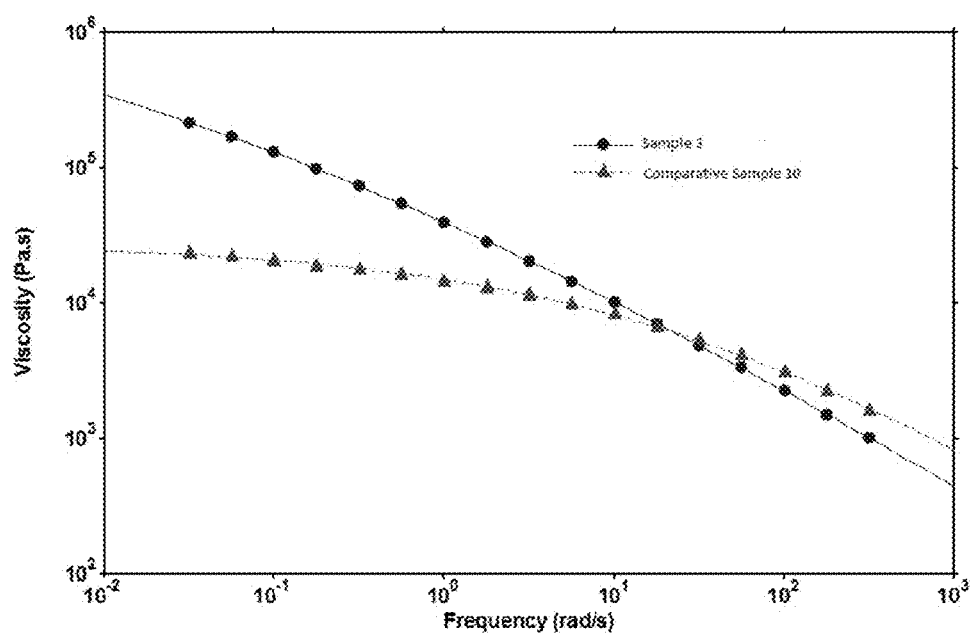

The rheological behavior of polymers of the present disclosure were investigated and the results are presented in Table IX and FIGS. 6 and 7. FIGS. 6 and 7 demonstrate that these resins are more highly shear thinning the corresponding metallocene resins which should provide greater melt strength, while processing more easily allowing for high output. Referring to Table IX, samples 1, 3, 5 and 7 generally displayed higher 10 values than comparative samples C6, C8, and C9. This greater level of processability is also suggested by the a-eta (CY-a) parameters for 1, 3, 5 and 7 which denote a high level of processabiltiy. The higher $\eta_0$ values of the polymer of the present disclosure correspond to increased bubble stability, and the values are closer to commercial benchmarks than the comparative samples. Without intending to be limited by theory, it is believed the improved η0 values are attributable to the broad molecular weight distribution of the polymer of the present disclosure.

For larger scale film testing purposes, catalyst A in described herein was used to prepare multiple batches of homopolymer resins according to the procedures for samples 6 and 7. Three blends, a 0.9 MI, 2.0 MI, and a 2.9 MI, were prepared designated as B1, B2, and B3 respectively as described in Table X.

TABLE X

| Blend No. | MI | $M_n$ (kg/mol) | $M_w$ (kg/mol) | $M_z$ (kg/mol) | $M_w/M_n$ | $M_z/M_n$ | $\eta_0$ (Pa-s) | CY-a |
|---|---|---|---|---|---|---|---|---|
| B1 | 0.9 | 6.2 | 146.0 | 1391 | 23.4 | 9.5 | 6.1E+04 | 0.210 |
| B2 | 2.0 | 5.6 | 124.2 | 1392 | 22.1 | 11.2 | 2.5E+04 | 0.209 |
| B3 | 2.9 | 6.1 | 113.0 | 1107 | 18.6 | 9.8 | 1.8E+04 | 0.207 |

The barrier properties of polymers of the type disclosed herein were also investigated and the results are presented in Table XI. In Table XI, it can be seen the polymers of samples B1, B2, and B3 have MVTR values similar to the values for comparative samples C6, and C7. As discussed previously, the densities for samples B1, B2, and B3 are higher than for comparative samples C6 and C7; while maintaining MVTR values similar to comparative samples C6 and C7.

TABLE XI

| Sample No. | Density (g/cc) | MVTR (90%) (g/100 in² · d) |
|---|---|---|
| B1 | 0.971 | 0.45 |
| B2 | 0.972 | 0.31 |
| B3 | 0.973 | 0.25 |
| C6 | 0.962 | 0.26 |
| C7 | 0.963 | 0.30 |

Also, as Tables X and XI demonstrate, the polymers of the present disclosure exhibit higher $\eta_0$ values while exhibiting similar, if not improved, MVTR performance. These results suggest that the polymers of this disclosure could be blown into films more easily and at higher rates than C6 and C7.

TABLE XI

| Sample No. | Gauge (mil) | $\eta_0$ (Pa-s) | Extrusion Pressure (psi) |
|---|---|---|---|
| B1 | 1.2 | 6.1E+04 | 500 |
| B2 | 1.25 | 2.5E+04 | 440 |
| B3 | 1.23 | 1.8E+04 | 340 |
| C6 | 1.1 | 4.5E+03 | 640 |
| C7 | 1.15 | 7.2E+03 | 700 |

The processability of the polymers of the present disclosure were investigated and are presented in Table XII. Referring to Table XII, it can be seen blends B1, B2, and B3 exhibited extrusion pressures in a range of about 340 psi to about 500 psi, while the comparative samples exhibited extrusion pressures in a range of about 640 psi to about 700 psi. These lower extrusion pressures may be beneficial to increasing blown film production rates. Without intending to be limited by theory, it is believe the improved extrusion pressures are attributable at least in part to the broad molecular weight distribution of the polymer of the present disclosure.

While embodiments of the disclosure have been shown and described, modifications thereof can be made by one skilled in the art without departing from the spirit and teachings of the disclosure. The embodiments described herein are exemplary only, and are not intended to be limiting. Many variations and modifications of the disclosure disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, Rl, and an upper limit, Ru, is disclosed, any number falling within the range is specifically disclosed. In particular, the following numbers within the range are specifically disclosed: R=Rl+k*(Ru−Rl), wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference herein is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

What is claimed:

1. An imine phenol compound having Structure I:

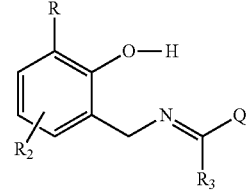

Structure I wherein:

O and N represent oxygen and nitrogen, respectively;

R comprises a halogen, a hydrocarbyl group, or a substituted hydrocarbyl group wherein the hydrocarbyl group or substituted hydrocarbyl group comprises a $C_1$ to $C_{30}$ alkyl group, a $C_4$ to $C_{30}$ cycloalkyl group, a $C_4$ to $C_{30}$ substituted cycloalkyl group, a $C_3$ to $C_{30}$ aliphatic heterocyclic group, a $C_3$ to $C_{30}$ substituted aliphatic heterocyclic group, a $C_6$ to $C_{30}$ aryl group, a $C_6$ to $C_{30}$ substituted aryl group, a $C_7$ to $C_{30}$ aralkyl group, a $C_7$ to $C_{30}$ substituted aralkyl group, a $C_3$ to $C_{30}$ heteroaryl group, or a $C_3$ to $C_{30}$ substituted heteroaryl group;

$R^2$ and $R^3$ are each independently be hydrogen, a halogen, a hydrocarbyl group, or a substituted hydrocarbyl group; and Q is a donor group having Structure II, Structure III or Structure IV:

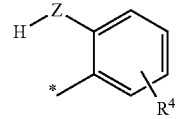

Structure II

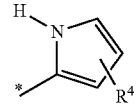

Structure III

-continued

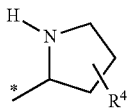

Structure IV where N represents nitrogen;

Z is oxygen or sulfur; and

R$^4$ comprises hydrogen, a halogen, a hydrocarbyl group, or a substituted hydrocarbyl group.

2. The compound of claim 1 wherein R$^2$ and R$^3$ are each independently a hydrogen, a halogen, a C$_1$ to C$_{30}$ alkyl group, a C$_4$ to C$_{30}$ cycloalkyl group, a C$_4$ to C$_{30}$ substituted cycloalkyl group, a C$_3$ to C$_{30}$ aliphatic heterocyclic group, a C$_3$ to C$_{30}$ substituted aliphatic heterocyclic group, a C$_6$ to C$_{30}$ aryl group, a C$_6$ to C$_{30}$ substituted aryl group, a C$_7$ to C$_{30}$ aralkyl group, a C$_7$ to C$_{30}$ substituted aralkyl group, a C$_3$ to C$_{30}$ heteroaryl group, or a C$_3$ to C$_{30}$ substituted heteroaryl group.

3. The compound of claim 1 wherein R is a methyl group, an ethyl group, a propyl group, a butyl group, a tert-butyl group, an adamantyl group, a chloride, a bromide, a trifluoro methyl group, a phenyl group, an aryl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group or combinations thereof.

4. The compound of claim 1 wherein R$^2$ and R$^3$ are each independently a hydrogen, methyl group, an ethyl group, a propyl group, a butyl group, a tert-butyl group, an adamantyl group, a tert-amyl, a chloride, a bromide, a trifluoro methyl group, a phenyl group, a aryl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, or combinations thereof.

5. The compound of claim 1 wherein R, R$^2$, and R$^3$ each independently have Structure A

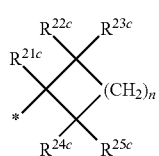

Structure A wherein R$^{21c}$, R$^{23c}$, R$^{24c}$, and R$^{25c}$ independently can be hydrogen or a non-hydrogen substituent, and n is an integer from 1 to 5.

6. A metal salt complex of an imine phenolate compound having Structure V:

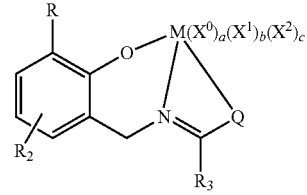

Structure V wherein:
O and N represent oxygen and nitrogen, respectively;
R comprises a halogen, a hydrocarbyl group, or a substituted hydrocarbyl group, wherein the hydrocarbyl group or substituted hydrocarbyl group comprises a C$_1$ to C$_{30}$ alkyl group, a C$_4$ to C$_{30}$ cycloalkyl group, a C$_4$ to C$_{30}$ substituted cycloalkyl group, a C$_3$ to C$_{30}$ aliphatic heterocyclic group, a C$_3$ to C$_{30}$ substituted aliphatic heterocyclic group, a C$_6$ to C$_{30}$ aryl group, a C$_6$ to C$_{30}$ substituted aryl group, a C$_7$ to C$_{30}$ aralkyl group, a C$_7$ to C$_{30}$ substituted aralkyl group, a C$_3$ to C$_{30}$ heteroaryl group, or a C$_3$ to C$_{30}$ substituted heteroaryl group;
R$^2$ and R$^3$ are each independently be hydrogen, a halogen, a hydrocarbyl group, or a substituted hydrocarbyl group;
Q is a donor group having Structure VI, Structure VII, or Structure VIII:

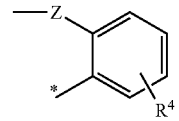

Structure VI

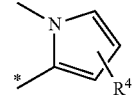

Structure VII

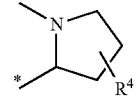

Structure VIII where Z is oxygen or sulfur and Z and N are both bound to M; and

R$^4$ comprises hydrogen, a halogen, a hydrocarbyl group, or a substituted hydrocarbyl group;

M is a group III to group 12 transition metal or lanthanide metal having an oxidation state equal to b+2c+2;

X$^0$ is a neutral ligand;

a is 0, 1, or 2;

X$^1$ is a monoanionic ligand;

b is 0, 1, 2, 3, or 4;

X$^2$ is a dianionic ligand; and c is 0, 1, or 2.

7. The metal salt complex of claim 6 wherein X$^0$ comprises an ether, a thioether, an amine, a nitrile, or a phosphine; X$^1$ comprises hydrogen, a halide, a C$_1$ to C$_{18}$ hydrocarbyl group, a hydrocarbyloxide group, a hydrocarbylamino group, a hydrocarbylsilyl group, or hydrocarbylaminosilyl group; and X$^2$ comprises an oxygen atom, =NR$^{2A}$, or =CR$^{2B}$R$^{2C}$ wherein R$^{2A}$, R$^{2B}$, and R$^{2C}$ are each independently hydrogen or a C$_1$ to C$_{18}$ hydrocarbyl group.

8. The metal salt of claim 6 where:
Q is Structure VI;
Z is oxygen; and
$R_3$ is hydrogen.

9. The metal salt complex of claim 6 wherein M is titanium, zirconium, or hafnium.

10. The metal salt complex of claim 6 wherein b is 2 and c is 0.

11. The metal salt complex of claim 6 having Structure XIV:

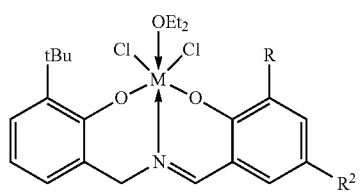

Structure XIV where M is zirconium, or hafnium;
R is hydrogen, a halogen, a hydrocarbyl group, or a substituted hydrocarbyl group; and
$R^2$ is hydrogen.

12. The metal salt complex of claim 6 having structure X:

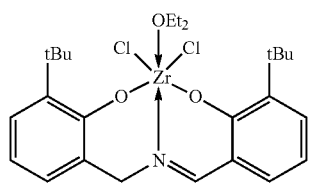

Structure X

13. The metal complex of claim 6 wherein $X^o$ is tetrahydrofuran, acetonitrile, pyridine, ammonia, dimethyl amine, diethyl amine, trimethyl amine, trimethylphosphine, or triphenylphosphine.

14. The metal complex of claim 6 wherein $R^2$ and $R^3$ are each independently a hydrogen, methyl group, an ethyl group, a propyl group, a butyl group, a tert-butyl group, an adamantyl group, a tert-amyl, a chloride, a bromide, a trifluoro methyl group, a phenyl group, an aryl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, or combinations thereof.

15. A catalyst composition comprising the metal salt complex of an imine phenolate compound of claim 6 and a metal alkyl compound.

16. The composition of claim 15 wherein the metal alkyl compound comprises an organoaluminum compound, an aluminoxane compound, and organoboron or organoborate compound, an ionizing ionic compound, or combinations thereof.

17. The composition of claim 15 further comprising an activator-support comprising a solid oxide treated with an electron-withdrawing anion.

18. The composition of claim 17 wherein the solid oxide comprises silica, alumina, silica-alumina, silica-coated alumina, aluminum phosphate, aluminophosphate, heteropolytungstate, titania, zirconia, magnesia, boria, zinc oxide, a mixed oxide thereof, or combinations thereof; and
wherein the electron-withdrawing anion comprises sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, or combinations thereof.

19. The composition of claim 15 wherein the metal alkyl compound comprises trialkylaluminum, an alkylaluminum halide, an alkylaluminum alkoxide, an aluminoxane, or combinations thereof.

20. The composition of claim 15 wherein the metal alkyl compound comprises methyl lithium, n-butyl lithium, sec-butyl lithium, tert-butyl lithium, diethyl magnesium, di-n-butylmagnesium, ethylmagnesium chloride, n-butylmagnesium chloride, diethyl zinc, trimethylaluminum, triethylaluminum, tripropylaluminum, tributylaluminum, trihexylaluminum, trioctylaluminum, diethyl aluminum chloride, diethylaluminum bromide, ethylaluminum dichloride, ethylaluminum sesquichloride, methylaluminoxane (MAO), ethylaluminoxane, modified methylaluminoxane (MMAO), n-propylaluminoxane, iso-propylaluminoxane, n-butylaluminoxane, sec-butyl aluminoxane, iso-butylaluminoxane, t-butyl aluminoxane, 1-pentylaluminoxane, 2-pentylaluminoxane, 3-pentylaluminoxane, iso-pentylaluminoxane, neo-pentylaluminoxane, or combinations thereof.

21. An olefin polymerization process comprising:
contacting the catalyst composition of claim 15 with an olefin monomer and optionally an olefin comonomer under conditions suitable for the formation of a polymer; and
recovering the polymer.

22. The process of claim 21 wherein the olefin monomer comprises ethylene and the polymer comprises polyethylene.

23. A process comprising contacting a catalyst composition with a monomer under conditions suitable for the formation of a polymer wherein the catalyst composition comprises a metal salt complex of an imine phenolate compound, a solid oxide, and an optional metal alkyl and wherein the metal salt complex of an imine phenolate compound has Structure XIV:

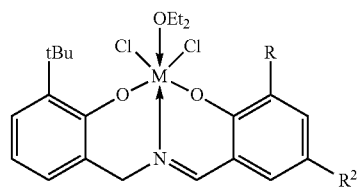

Structure XIV where M is titanium, zirconium, or hafnium;
$OEt_2$ is diethyl ether;
R comprises a halogen, a hydrocarbyl group, or a substituted hydrocarbyl group; and
$R^2$ comprises hydrogen, a halogen, a hydrocarbyl group, or a substituted hydrocarbyl group.

* * * * *